US009121840B2

(12) United States Patent
Minvielle

(10) Patent No.: US 9,121,840 B2
(45) Date of Patent: Sep. 1, 2015

(54) LOGISTIC TRANSPORT SYSTEM FOR NUTRITIONAL SUBSTANCES

(71) Applicant: Eugenio Minvielle, Rye, NY (US)

(72) Inventor: Eugenio Minvielle, Rye, NY (US)

( * ) Notice: Subject to any disclaimer, the term of this patent is extended or adjusted under 35 U.S.C. 154(b) by 0 days.

(21) Appl. No.: 14/059,441

(22) Filed: Oct. 21, 2013

(65) Prior Publication Data

US 2014/0041532 A1 Feb. 13, 2014

Related U.S. Application Data

(63) Continuation-in-part of application No. 14/051,379, filed on Oct. 10, 2013, which is a continuation-in-part of application No. 13/485,854, filed on May 31, 2012.

(60) Provisional application No. 61/624,948, filed on Apr. 16, 2012, provisional application No. 61/624,972, filed on Apr. 16, 2012, provisional application No. 61/624,985, filed on Apr. 16, 2012.

(51) Int. Cl.
*B02C 25/00* (2006.01)
*A01J 11/00* (2006.01)
(Continued)

(52) U.S. Cl.
CPC .............. *G01N 33/02* (2013.01); *A23B 7/148* (2013.01); *A23B 7/152* (2013.01); *A23L 3/001* (2013.01); *A23L 3/003* (2013.01)

(58) Field of Classification Search
CPC .............. G06Q 30/02; G06Q 10/087; G06K 2017/0067
USPC .................. 99/486, 353, 455, 646; 702/1, 22, 702/31–32; 705/1.1, 15; 426/72, 648; 434/127; 700/266, 9, 28; 73/865.8; 235/383, 375, 492, 380, 382.5
See application file for complete search history.

(56) References Cited

U.S. PATENT DOCUMENTS 4,225,410 A * 9/1980 Pace ............................. 204/412
4,555,930 A * 12/1985 Leach et al. .................. 73/23.2
(Continued)

FOREIGN PATENT DOCUMENTS

DE 10 2005 040206 A1 2/2007
EP 1117055 7/2001
(Continued)

OTHER PUBLICATIONS

M. Ghasemi-Varnamkhasti, et al: "Biomimetic-based odor and taste sensing systems to food quality and safety characterization: An overview on basic principles and recent acheivements", May 2010, J. of Food Engineering, 100 (2010), pp. 377-387.*
(Continued)

*Primary Examiner* — Dana Ross
*Assistant Examiner* — Gyounghyun Bae
(74) *Attorney, Agent, or Firm* — Nixon Peabody LLP

(57) ABSTRACT

Disclosed herein is a preservation system for storage and logistic transport of nutritional substances. The preservation system obtains information about the nutritional substance to be preserved, senses and measures the external environment to the preservation system, senses and measures the internal environment to the preservation system, senses and measures the state of the nutritional substance, and stores such information throughout the period of preservation. Using this accumulated information, the preservation system can measure, or estimate, changes in nutritional content (usually degradation) during the period of preservation. Additionally, the preservation system can use this information to dynamically modify the preservation system to minimize detrimental changes to the nutritional content of the nutritional substance, and in some cases actually improve the nutritional substance attributes.

8 Claims, 15 Drawing Sheets

(51) Int. Cl.
  *A47J 27/04*    (2006.01)
  *G01N 31/00*    (2006.01)
  *A23L 1/30*     (2006.01)
  *G09B 19/00*    (2006.01)
  *G01N 33/02*    (2006.01)
  *A23L 3/00*     (2006.01)
  *A23B 7/148*    (2006.01)
  *A23B 7/152*    (2006.01)

(56) References Cited

U.S. PATENT DOCUMENTS

| | | | |
|---|---|---|---|
| 4,644,154 A * | 2/1987 | Brogårdh et al. | 250/227.23 |
| 4,650,766 A | 3/1987 | Harm et al. | |
| 4,674,320 A * | 6/1987 | Hirschfeld | 73/31.06 |
| D333,782 S | 3/1993 | van Berlo | |
| 5,250,789 A | 10/1993 | Johnsen | |
| 5,412,560 A | 5/1995 | Dennison | |
| 5,442,669 A | 8/1995 | Medin | |
| 5,478,900 A | 12/1995 | Amano et al. | |
| 5,478,989 A | 12/1995 | Shepley | |
| 5,673,691 A | 10/1997 | Abrams et al. | |
| 5,697,177 A | 12/1997 | Ludlow et al. | |
| 5,804,803 A | 9/1998 | Cragun et al. | |
| 5,853,790 A | 12/1998 | Glancy | |
| 5,872,721 A * | 2/1999 | Huston et al. | 702/24 |
| 5,954,640 A | 9/1999 | Szabo | |
| 6,012,415 A | 1/2000 | Linseth | |
| 6,182,725 B1 | 2/2001 | Sorvik | |
| 6,211,789 B1 | 4/2001 | Oldham et al. | |
| 6,276,264 B1 * | 8/2001 | Dumm | 99/455 |
| 6,325,878 B1 | 12/2001 | Borgstrom | |
| 6,356,940 B1 | 3/2002 | Short | |
| 6,444,233 B1 | 9/2002 | Arntzen et al. | |
| 6,483,434 B1 | 11/2002 | UmiKer | |
| 6,491,217 B2 | 12/2002 | Catan | |
| 6,502,411 B2 | 1/2003 | Okamoto | |
| 6,512,919 B2 | 1/2003 | Ogasawara | |
| 6,513,532 B2 | 2/2003 | Mault et al. | |
| 6,549,818 B1 | 4/2003 | Ali | |
| 6,554,182 B1 | 4/2003 | Magnusson et al. | |
| 6,556,963 B1 | 4/2003 | Tetzlaff | |
| 6,571,603 B1 * | 6/2003 | Doleman et al. | 73/23.34 |
| D478,773 S | 8/2003 | Palen | |
| 6,616,047 B2 | 9/2003 | Catan | |
| 6,631,333 B1 * | 10/2003 | Lewis et al. | 702/24 |
| 6,671,698 B2 | 12/2003 | Pickett et al. | |
| 6,676,014 B2 | 1/2004 | Catan | |
| 6,689,398 B2 | 2/2004 | Haridas et al. | |
| 6,691,135 B2 | 2/2004 | Pickett et al. | |
| 6,716,462 B2 * | 4/2004 | Prosise et al. | 426/72 |
| 6,773,926 B1 * | 8/2004 | Freund et al. | 436/149 |
| 6,789,021 B2 * | 9/2004 | Rendahl et al. | 702/22 |
| 6,844,197 B1 * | 1/2005 | Doleman et al. | 436/151 |
| 6,888,458 B2 | 5/2005 | Carlson | |
| 6,953,342 B2 | 10/2005 | Bisogno | |
| 6,975,910 B1 | 12/2005 | Brown et al. | |
| 7,024,369 B1 | 4/2006 | Brown et al. | |
| 7,076,438 B1 | 7/2006 | Tobelmann et al. | |
| 7,085,777 B2 | 8/2006 | Beck et al. | |
| 7,090,638 B2 | 8/2006 | Vidgen | |
| 7,103,481 B2 * | 9/2006 | Negri | 702/22 |
| 7,151,447 B1 | 12/2006 | Willms et al. | |
| 7,152,040 B1 | 12/2006 | Hawthorne et al. | |
| D534,758 S | 1/2007 | Lee et al. | |
| D539,072 S | 3/2007 | Kawata et al. | |
| D539,595 S | 4/2007 | Okuda et al. | |
| D540,613 S | 4/2007 | Jeon | |
| D541,578 S | 5/2007 | Jeon | |
| 7,212,955 B2 | 5/2007 | Kirshenbau et al. | |
| 7,213,743 B2 | 5/2007 | Carlson et al. | |
| 7,256,699 B2 | 8/2007 | Tethrake et al. | |
| 7,275,863 B1 | 10/2007 | Akers et al. | |
| D560,960 S | 2/2008 | Hillmann et al. | |
| 7,357,316 B2 | 4/2008 | Heckel et al. | |
| 7,359,802 B1 * | 4/2008 | Lewis et al. | 702/24 |
| 7,372,003 B2 * | 5/2008 | Kates | 219/494 |
| 7,403,855 B2 | 7/2008 | Fuessley et al. | |
| 7,440,901 B1 | 10/2008 | Dlott et al. | |
| 7,474,965 B2 * | 1/2009 | Johnson et al. | 702/22 |
| 7,571,676 B2 * | 8/2009 | Nelson et al. | 99/477 |
| 7,620,531 B1 | 11/2009 | Johnson | |
| D607,264 S | 1/2010 | Lee | |
| D618,488 S | 6/2010 | Knochner | |
| 7,797,204 B2 | 9/2010 | Balent | |
| 7,836,876 B2 * | 11/2010 | Schellenberg | 126/268 |
| 7,840,359 B2 * | 11/2010 | Hsiung et al. | 702/22 |
| D633,326 S | 3/2011 | Shin et al. | |
| 8,009,048 B2 | 8/2011 | Hyde et al. | |
| 8,033,237 B2 | 10/2011 | Havens et al. | |
| D654,299 S | 2/2012 | Benold | |
| 8,112,303 B2 | 2/2012 | Eglen et al. | |
| D657,607 S | 4/2012 | Ohmae et al. | |
| D665,220 S | 8/2012 | Ohmae et al. | |
| 8,314,701 B2 | 11/2012 | Grieco et al. | |
| D673,001 S | 12/2012 | Becze et al. | |
| 8,403,215 B2 | 3/2013 | Aihara et al. | |
| 8,490,862 B1 | 7/2013 | Minvielle | |
| 8,550,365 B1 | 10/2013 | Minvielle | |
| 8,626,796 B2 | 1/2014 | McBride et al. | |
| 8,631,050 B1 | 1/2014 | Gayle | |
| 8,668,140 B2 | 3/2014 | Minvielle | |
| D702,482 S | 4/2014 | Davis et al. | |
| 2002/0004749 A1 | 1/2002 | Froseth et al. | |
| 2002/0011567 A1 | 1/2002 | Ozanich | |
| 2002/0040564 A1 | 4/2002 | Killingbeck et al. | |
| 2002/0059175 A1 | 5/2002 | Nakano | |
| 2002/0091593 A1 | 7/2002 | Fowler | |
| 2002/0106432 A1 | 8/2002 | Yamagata et al. | |
| 2002/0125313 A1 | 9/2002 | Broff | |
| 2003/0027161 A1 | 2/2003 | Bejanin et al. | |
| 2003/0136960 A1 * | 7/2003 | Goodman et al. | 257/40 |
| 2003/0163354 A1 | 8/2003 | Shamoun | |
| 2003/0165602 A1 | 9/2003 | Garwood | |
| 2003/0185937 A1 | 10/2003 | Garwood | |
| 2003/0185948 A1 | 10/2003 | Garwood | |
| 2004/0045202 A1 | 3/2004 | Arrendale, III et al. | |
| 2004/0083201 A1 | 4/2004 | Sholl et al. | |
| 2004/0100380 A1 | 5/2004 | Lindsay et al. | |
| 2004/0147038 A1 * | 7/2004 | Lewis et al. | 436/149 |
| 2004/0152131 A1 | 8/2004 | Hsieh | |
| 2004/0167724 A1 * | 8/2004 | Federer et al. | 702/32 |
| 2004/0201454 A1 | 10/2004 | Waterhouse et al. | |
| 2004/0215402 A1 * | 10/2004 | Hsiung et al. | 702/22 |
| 2005/0001728 A1 | 1/2005 | Appelt et al. | |
| 2005/0027726 A1 | 2/2005 | Guivarch et al. | |
| 2005/0049920 A1 | 3/2005 | Day et al. | |
| 2005/0075900 A1 | 4/2005 | Arguimbau, III | |
| 2005/0079491 A1 | 4/2005 | Donne-Gousse et al. | |
| 2005/0168325 A1 | 8/2005 | Lievre et al. | |
| 2005/0171738 A1 | 8/2005 | Kadaba | |
| 2005/0247213 A1 | 11/2005 | Slilaty | |
| 2005/0248455 A1 | 11/2005 | Pope et al. | |
| 2005/0251449 A1 | 11/2005 | Pape et al. | |
| 2006/0015371 A1 | 1/2006 | Knauf et al. | |
| 2006/0061454 A1 | 3/2006 | Debord et al. | |
| 2006/0062835 A1 | 3/2006 | Weil | |
| 2006/0073483 A1 * | 4/2006 | White et al. | 435/6 |
| 2006/0078658 A1 | 4/2006 | Owens et al. | |
| 2006/0099310 A1 | 5/2006 | Koekkoek | |
| 2006/0130498 A1 | 6/2006 | Joshi et al. | |
| 2006/0172048 A1 | 8/2006 | Etchells et al. | |
| 2006/0200480 A1 | 9/2006 | Harris et al. | |
| 2006/0256132 A1 | 11/2006 | Shin et al. | |
| 2006/0277064 A1 | 12/2006 | Cannata | |
| 2007/0016852 A1 | 1/2007 | Kim et al. | |
| 2007/0055551 A1 | 3/2007 | Szabo | |
| 2007/0055573 A1 | 3/2007 | Grell | |
| 2007/0118394 A1 | 5/2007 | Cahoon | |
| 2007/0191689 A1 | 8/2007 | Elitok | |
| 2007/0258048 A1 | 11/2007 | Pitchers | |
| 2007/0269557 A1 | 11/2007 | Culver et al. | |
| 2007/0294129 A1 | 12/2007 | Froseth et al. | |
| 2008/0058783 A1 | 3/2008 | Altshuler et al. | |

(56) References Cited

U.S. PATENT DOCUMENTS

| | | |
|---|---|---|
| 2008/0059342 A1 | 3/2008 | Culver et al. |
| 2008/0077455 A1 | 3/2008 | Gilboa |
| 2008/0083825 A1 | 4/2008 | Yang et al. |
| 2008/0091705 A1 | 4/2008 | McBride et al. |
| 2008/0158543 A1 | 7/2008 | Puskas et al. |
| 2008/0171120 A1* | 7/2008 | Willett .......................... 426/496 |
| 2008/0183588 A1 | 7/2008 | Agrawal et al. |
| 2008/0186175 A1 | 8/2008 | Stern |
| 2008/0195456 A1 | 8/2008 | Fitzpatrick et al. |
| 2008/0254449 A1 | 10/2008 | Plante |
| 2009/0029014 A1 | 1/2009 | Walter et al. |
| 2009/0065570 A1 | 3/2009 | Peters et al. |
| 2009/0070040 A1 | 3/2009 | Rabinovitch et al. |
| 2009/0099873 A1 | 4/2009 | Kurple |
| 2009/0157460 A1* | 6/2009 | Narayanaswamy .............. 705/8 |
| 2009/0202700 A1 | 8/2009 | Bunke et al. |
| 2009/0208607 A1 | 8/2009 | Bunke et al. |
| 2009/0275002 A1 | 11/2009 | Hoggle |
| 2009/0278685 A1 | 11/2009 | Potyrailo et al. |
| 2009/0282004 A1 | 11/2009 | Williams |
| 2009/0283517 A1 | 11/2009 | Mackay et al. |
| 2009/0286212 A1 | 11/2009 | Gordon |
| 2009/0288606 A1 | 11/2009 | Zimmerman |
| 2010/0076585 A1 | 3/2010 | Mayer et al. |
| 2010/0097193 A1 | 4/2010 | Tang |
| 2010/0106625 A1* | 4/2010 | McCoy .......................... 705/28 |
| 2010/0106626 A1* | 4/2010 | Ashrafzadeh et al. .......... 705/29 |
| 2010/0117819 A1 | 5/2010 | Murray |
| 2010/0119659 A1 | 5/2010 | Ovadia et al. |
| 2010/0135211 A1 | 6/2010 | Park et al. |
| 2010/0152687 A1 | 6/2010 | Carlozzi |
| 2010/0198605 A1 | 8/2010 | Saulet |
| 2010/0216098 A1 | 8/2010 | Montgomery |
| 2010/0216136 A1 | 8/2010 | B.Che Man et al. |
| 2010/0228160 A1 | 9/2010 | Schweizer |
| 2010/0268658 A1 | 10/2010 | Medo et al. |
| 2010/0280895 A1 | 11/2010 | Mottola |
| 2010/0287101 A1 | 11/2010 | Ishikawa et al. |
| 2011/0029364 A1 | 2/2011 | Roeding et al. |
| 2011/0082711 A1 | 4/2011 | Poeze et al. |
| 2011/0124096 A1 | 5/2011 | Philipak et al. |
| 2011/0204137 A1 | 8/2011 | Scharfenort et al. |
| 2011/0217205 A1 | 9/2011 | Peeters |
| 2011/0236862 A1 | 9/2011 | Culver et al. |
| 2011/0258130 A1 | 10/2011 | Grabiner et al. |
| 2011/0259960 A1 | 10/2011 | Baarman et al. |
| 2011/0301441 A1 | 12/2011 | Bandic et al. |
| 2011/0302050 A1 | 12/2011 | Kildevaeld |
| 2012/0004935 A1 | 1/2012 | Winkler |
| 2012/0005105 A1 | 1/2012 | Beier et al. |
| 2012/0016814 A1 | 1/2012 | Evans |
| 2012/0027897 A1 | 2/2012 | Innocenzi |
| 2012/0052162 A1 | 3/2012 | Goulart |
| 2012/0055718 A1 | 3/2012 | Chen |
| 2012/0083669 A1 | 4/2012 | Abujbara |
| 2012/0085828 A1 | 4/2012 | Ziegler |
| 2012/0085829 A1 | 4/2012 | Ziegler |
| 2012/0105424 A1 | 5/2012 | Lee et al. |
| 2012/0169469 A1 | 7/2012 | Butler et al. |
| 2012/0179665 A1 | 7/2012 | Baarman et al. |
| 2012/0203572 A1 | 8/2012 | Christensen |
| 2012/0216911 A1 | 8/2012 | Bartholomew et al. |
| 2012/0251663 A1 | 10/2012 | Prins et al. |
| 2012/0274470 A1 | 11/2012 | Sandvick |
| 2012/0315609 A1 | 12/2012 | Miller-Kovach et al. |
| 2013/0048736 A1 | 2/2013 | Wien |
| 2013/0048737 A1 | 2/2013 | Baym et al. |
| 2013/0052616 A1 | 2/2013 | Silverstein et al. |
| 2013/0080784 A1 | 3/2013 | Oertli |
| 2013/0105565 A1 | 5/2013 | Kamprath |
| 2013/0117310 A1 | 5/2013 | Chai et al. |
| 2013/0269297 A1 | 10/2013 | Minvielle |
| 2013/0269454 A1 | 10/2013 | Minvielle |
| 2013/0269537 A1 | 10/2013 | Minvielle |
| 2013/0269538 A1 | 10/2013 | Minvielle |
| 2013/0269542 A1 | 10/2013 | Minvielle |
| 2013/0269543 A1 | 10/2013 | Minvielle |
| 2013/0269544 A1 | 10/2013 | Minvielle |
| 2013/0270337 A1 | 10/2013 | Minvielle |
| 2013/0273217 A1 | 10/2013 | Minvielle |
| 2013/0273222 A1 | 10/2013 | Minvielle |
| 2013/0273507 A1 | 10/2013 | Minvielle |
| 2013/0275037 A1 | 10/2013 | Minvielle |
| 2013/0275318 A1 | 10/2013 | Minvielle |
| 2013/0275342 A1 | 10/2013 | Minvielle |
| 2013/0275343 A1 | 10/2013 | Minvielle |
| 2013/0275370 A1 | 10/2013 | Minvielle |
| 2013/0275426 A1 | 10/2013 | Minvielle |
| 2013/0275439 A1 | 10/2013 | Minvielle |
| 2013/0275460 A1 | 10/2013 | Minvielle |
| 2013/0275477 A1 | 10/2013 | Minvielle |
| 2013/0276644 A1 | 10/2013 | Minvielle |
| 2013/0290364 A1 | 10/2013 | Minvielle |
| 2013/0295532 A1 | 11/2013 | Minvielle |
| 2013/0297642 A1 | 11/2013 | Minvielle |
| 2013/0309138 A1 | 11/2013 | Minvielle |
| 2013/0309636 A1 | 11/2013 | Minvielle |
| 2013/0309637 A1 | 11/2013 | Minvielle |
| 2013/0310955 A1 | 11/2013 | Minvielle |
| 2013/0337516 A1 | 12/2013 | Herrema |
| 2014/0037805 A1 | 2/2014 | Minvielle |
| 2014/0038140 A1 | 2/2014 | Minvielle |
| 2014/0041533 A1 | 2/2014 | Minvielle |
| 2014/0061296 A1 | 3/2014 | Minvielle |
| 2014/0069838 A1 | 3/2014 | Minvielle |

FOREIGN PATENT DOCUMENTS

| | | |
|---|---|---|
| EP | 1 253 203 A1 | 10/2002 |
| FR | 2813683 | 3/2002 |
| GB | 2312054 | 10/1997 |
| WO | 91/13304 | 9/1991 |
| WO | 02/06984 | 1/2002 |
| WO | 02/37375 | 5/2002 |
| WO | 2007/108906 A2 | 9/2007 |
| WO | 2008/054231 | 5/2008 |

OTHER PUBLICATIONS

Thakur, M. et al., "Food Traceability, R&D in Norway", Food Technology, Apr. 2012, p. 42-46.

Hoffman, B., "IBM Announces Food Traceability Technology", Food+Tech Connect, Oct. 19, 2011, 2 pages.

"SIRA Technologies Food Sentinal System Thermal Barcode for Packaging", Sustainable is Good: Lifestyle and Design Blog, Mar. 4, 2009, 2 pages.

Montesinos, E., "Plant-associated Microorganisms: a View from the Scope of Microbiology", International Microbiology, (2003), vol. 6, Issue 4, pp. 221-223.

Sinclair, D.A. et al., "Unlocking the Secrets of Longevity Genes", Scientific American, Mar. 2006, vol. 294, Issue 3, pp. 48-57.

Diller, K.R., "Stress Protein Expression Kinetics", Annual Review of Biomedical Engineering, 2006, vol. 8, pp. 403-424.

Zerebecki, R.A. et al., "Temperature Tolerance and Stress Proteins as Mechanisms of Invasive Species Success", PLoS One, Apr. 2011, vol. 6, Issue 4, e14806, pp. 1-7.

Ni, Fu-Tai et al., "Gene Expression and Regulation of Higher Plants Under Soil Water Stress", Current Genomics, Jun. 2009, vol. 10, pp. 269-280.

Hayano-Kanashiro, C. et al., "Analysis of Gene Expression and Physiological Responses in Three Mexican Maize Landraces Under Drought Stress and Recovery Irrigation", PLoS One, Oct. 2009, vol. 4, Issue 10, e7531, pp. 1-19.

Kingsmore, S F., "Multiplexed Protein Measurement: Technologies and Applications of Protein and Antibody Arrays", Nature Reviews Drug Discovery, Apr. 2006, vol. 5, pp. 310-321.

Kaume, L. et al., "The Blackberry Fruit: A Review on Its Composition and Chemistry, Metabolism and Bioavailability, and Health Benefits", Journal of Agricultural and Food Chemistry, 2012, vol. 60 (23), pp. 5716-5727.

(56) References Cited

OTHER PUBLICATIONS

Perks, B., "Fighting Food Fraud with Science", Text Reproduced from Chemistry World, 2007, vol. 4 (9), pp. 48-52.
Montealegre, C. et al., "Traceability Markers to the Botanical Origin in Olive Oils", Journal of Agricultural and Food Chemistry, 2010, vol. 58 (1), pp. 28-38.
Martins-Lopes, P. et al., "DNA Markers for Portuguese Olive Oil Fingerprinting", Journal of Agricultural and Food Chemistry, 2008, vol. 56 (24), pp. 11786-11791.
Garcia-Gonzalez, D.L. et al., "Research in Olive Oil: Challenges for the Near Future", Journal of Agricultural and Food Chemistry, 2010, vol. 58 (24), pp. 12569-12577.
Zou, Ming-Qiang et al., "Rapid Authentication of Olive Oil Adulteration by Raman Spectrometry", Journal of Agricultural and Food Chemistry, 2009, vol. 57 (14), pp. 6001-6006.
Frankel, E.N., "Chemistry of Extra Virgin Olive Oil: Adulteration, Oxidative Stability, and Antioxidants", Journal of Agricultural and Food Chemistry, 2010, vol. 58 (10), pp. 5991-6006.
Lago, Fatima C. et al., "FINS Methodology to Identification of Sardines and Related Species in Canned Products and Detection of Mixture by Means of SNP Analysis Systems", European Food Research and Technology, Jun. 2011, vol. 232(6), pp. 1077-1086.
Lago, Fatima C. et al., "Genetic Identification of Horse Mackerel and Related Species in Seafood Products by Means of Forensically Informative Nucleotide Sequencing Methodology", Journal of Agricultural and Food Chemistry, 2011, vol. 59 (6), pp. 2223-2228.
Suslick, B.A. et al., "Discrimination of Complex Mixtures by a Colorimetric Sensor Array: Coffee Aromas", Analytical Chemistry, Mar. 1, 2010, vol. 82, No. 5, pp. 2067-2073.
Rashidi, L. et al., "The Applications of Nanotechnology in Food Industry", Critical Reviews in Food Science and Nutrition, 2011, vol. 51, Issue 8, pp. 723-730.
Staggers, N. et al., "Nanotechnology: The Coming Revolution and its Implications for Consumers, Clinicians, and Informatics", Nursing Outlook, Sep.-Oct. 2008, vol. 56, No. 5, pp. 268-274.
Chaudhry, Q. et al., "Applications and Implications of Nanotechnologies for the Food Sector", Food Additives and Contaminants: Part A, Mar. 2008, vol. 25, Issue 3, pp. 241-258.
Srinivas, P.R. et al., "Nanotechnology Research: Applications in Nutritional Sciences", The Journal of Nutrition, Symposium-Nanotechnology Research: Applications in Nutritional Sciences, Jan. 2010, vol. 140, No. 1, pp. 119-124.
Walt, D.R., "Electronic Noses: Wake Up and Smell the Coffee", Analytical Chemistry, Feb. 1, 2005, vol. 77 (3), p. A-45.
Aernecke, M.J. et al., "Optical-fiber Arrays for Vapor Sensing", Sensors and Actuators B. Chemical, Nov. 2009, vol. 142, Issue 2, pp. 464-469.
Anslyn, E.V., "Supramolecular Analytical Chemistry", The Journal of Organic Chemistry, Feb. 2, 2007, vol. 72, No. 3, pp. 687-699.
Lewis, N.S., "Comparisons Between Mammalian and Artificial Olfaction Based on Arrays of Carbon Black-Polymer Composite Vapor Detectors", Accounts of Chemical Research, 2004, vol. 37, No. 9, pp. 663-672.
Röck, F. et al., "Electronic Nose: Current Status and Future Trends", Chemical Reviews, 2008, vol. 108, No. 2, pp. 705-725.
Hierlemann, A. et al., "Higher-Order Chemical Sensing", Chemical Reviews, 2008, vol. 108, No. 2, pp. 563-613.
Hsieh, Meng-Da et al., "Limits of Recognition for Simple Vapor Mixtures Determined with a Microsensor Array", Analytical Chemistry, Apr. 1, 2004, vol. 76, No. 7, pp. 1885-1895.
Grate, J.W., "Acoustic Wave Microsensor Arrays for Vapor Sensing", Chemical Reviews, 2000, vol. 100, No. 7, pp. 2627-2647.
Janata, J. et al., "Conducting Polymers in Electronic Chemical Sensors", Nature Materials, Jan. 2003, vol. 2, pp. 19-24.
Wolfbeis, O.S., "Materials for Fluorescence-based Optical Chemical Sensors", Journal of Materials Chemistry, 2005, vol. 15, pp. 2657-2669.
James, D. et al., "Chemical Sensors for Electronic Nose Systems", Microchimica Acta, Feb. 2005, vol. 149, pp. 1-17.

Primrose, S. et al., "Food Forensics: Methods for Determining the Authenticity of Foodstuffs", Trends in Food Science & Technology, Dec. 2010, vol. 21 (12), pp. 582-590.
Kharif, Olga, "Janne Haverinen: Mapping the Great Indoors", Bloomberg BusinessWeek, May 9, 2012, retrieved from URL: <http://www.businessweek.com/articles/2012-08-09/janne-haverinen-mapping-the-great-indoors on Apr. 12, 2013>.
Cheftel, J. Claude, "Food and Nutrition Labelling in the European Union", Food Chemistry 93.3, Dec. 2005, pp. 531-550, retrieved on Mar. 10, 2013 from URL: <http://www.sciencedirect.com/science/article/pii/S0308814604008581>.
Etherington, Darrell, "iCarte Turns the iPhone Into an RFID Reader," Gigaom, Nov. 18, 2009 (downloaded Oct. 3, 2013, from URL http://gigaom.com/2009/11/18/icarte-turns-the-iphone-into-an-rfid-reader/).
Greenfield, H. et al., "Food composition data," FAO, 2003 ("FAO").
Office Action in U.S. Appl. No. 13/485,850, mailed May 9, 2013.
Office Action in U.S Appl. No. 13/485,850, mailed Sep. 30, 2013.
Office Action in U.S. Appl. No. 13/485,850, mailed Mar. 20, 2014.
Office Action in U.S. Appl. No. 13/485,878, mailed Oct. 24, 2013.
Office Action in U.S. Appl. No. 13/560,965, mailed Feb. 1, 2013.
Office Action in U.S. Appl. No. 13/602,040, mailed Jan. 11, 2013.
Office Action in U.S. Appl. No. 13/602,040, mailed Oct. 23, 2013.
Office Action in U.S. Appl. No. 13/685,575, mailed May 6, 2013.
Office Action in U.S. Appl. No. 13/685,575, mailed Oct. 24, 2013.
Office Action in U.S. Appl. No. 13/732,050, mailed Oct. 24, 2013.
Office Action in U.S. Appl. No. 13/732,050, mailed Apr. 10, 2014.
Office Action in U.S. Appl. No. 13/750,804, mailed Mar. 12, 2013.
Office Action in U.S. Appl. No. 13/771,004, mailed May 15, 2013.
Office Action in U.S. Appl. No. 13/771,004, mailed Jul. 8, 2013.
Office Action in U.S. Appl. No. 13/771,004, mailed Apr. 4, 2014.
Office Action in U.S. Appl. No. 13/888,353, mailed Jul. 25, 2013.
Office Action in U.S. Appl. No. 13/888,353, mailed Dec. 4, 2013.
Office Action in U.S. Appl. No. 13/900,426, mailed Aug. 8, 2013.
Office Action in U.S. Appl. No. 13/931,744, mailed Aug. 20, 2013.
Office Action in U.S. Appl. No. 13/937,167, mailed Oct. 28, 2013.
Office Action in U.S. Appl. No. 13/937,167, mailed Apr. 14, 2014.
Office Action in U.S. Appl. No. 13/948,004, mailed Oct. 24, 2013.
Office Action in U.S. Appl. No. 14/047,817, mailed Nov. 29, 2013.
Office Action in U.S. Appl. No. 14/074,664, mailed Jan. 8, 2014.
Notice of Allowance in U.S. Appl. No. 13/560,965, mailed Mar. 22, 2013.
Notice of Allowance in U.S. Appl. No. 13/750,804, mailed May 31, 2013.
Notice of Allowance in U.S. Appl. No. 13/900,426, mailed Dec. 16, 2013.
Notice of Allowance in U.S. Appl. No. 14/047,817, mailed Apr. 14, 2014.
Notice of Allowance in U.S. Appl. No. 13/931,744, mailed Feb. 28, 2014.
PCT International Search Report and Written Opinion in International Application No. PCT/US2013/029686, mailed May 13, 2013.
PCT International Search Report and Written Opinion in International Application No. PCT/US2013/031106, mailed May 31, 2013.
PCT International Search Report and Written Opinion in International Application No. PCT/US2013/27148, mailed Jun. 18, 2013.
PCT International Search Report and Written Opinion in International Application No. PCT/US2013/29219, mailed Jun. 20, 2013.
PCT International Search Report and Written Opinion in International Application No. PCT/US2013/36666, mailed Oct. 4, 2013.
PCT International Search Report and Written Opinion in International Application No. PCT/US2013/036668, mailed Dec. 6, 2013.
PCT International Search Report and Written Opinion in International Application No. PCT/US2013/036670, mailed Aug. 19, 2013.
PCT International Search Report and Written Opinion in International Application No. PCT/US2013/036673, mailed Aug. 20, 2013.
PCT International Search Report and Written Opinion in International Application No. PCT/US2013/040445, mailed Oct. 25, 2013.
Extended European Search Report in European Application No. 13757669.0, dated Jan. 31, 2014.
Extended European Search Report in European Application No. 13731655.0, dated Feb. 24, 2014.

(56) References Cited

OTHER PUBLICATIONS

Statement in accordance with the Notice from the European Patent Office, dated Oct. 1, 2007, concerning business methods.
Notice from the European Patent Office, dated Oct. 1, 2007, concerning business methods, Official Journal EPO, pp. 592-593.
Office Action in U.S. Appl. No. 13/602,040, mailed Jul. 17, 2014.
Office Action in U.S. Appl. No. 13/888,353, mailed May 1, 2014.
Office Action in U.S. Appl. No. 14/137,963, mailed May 7, 2014.
Notice of Allowance in U.S. Appl. No. 14/074,664, mailed Jun. 2, 2014.
Office Action in U.S. Appl. No. 13/485,878, mailed Jun. 5, 2014.
Office Action in U.S. Appl. No. 13/948,004, mailed Jun. 11, 2014.
Preechaburana, Pakorn et al., "Surface Plasmon Resonance Chemical Sensing on Cell Phones", Angewandte Chemie International Edition, vol. 51, Issue 46, pp. 11585-11588, first published online Oct. 16, 2012.
Office Action in U.S. Appl. No. 13/485,863, mailed Feb. 9, 2015.
Office Action in U.S. Appl. No. 13/861,300 mailed Feb. 24, 2015.
Office Action in U.S. Appl. No. 13/931,733, mailed Mar. 10, 2015.
Office Action in U.S. Appl. No. 13/771,004, mailed Mar. 10, 2015.
Notice of Allowance in U.S. Appl. No. 14/305,111, mailed Mar. 17, 2015.
Office Action in U.S. Appl. No. 13/485,850, mailed Mar. 19, 2015.
Office Action in U.S. Appl. No. 13/646,632, mailed Mar. 26, 2015.
Office Action in U.S. Appl. No. 13/888,353, mailed Mar. 26, 2015.
Office Action in U.S. Appl. No. 13/485,918, mailed Mar. 27, 2015.
Office Action in U.S. Appl. No. 14/203,353, mailed Mar. 31, 2015.
Notice of Allowance in U.S. Appl. No. 14/044,851, mailed Mar. 31, 2015.
Notice of Allowance in U.S. Appl. No. 13/921,078, mailed Apr. 1, 2015.
Office Action in U.S. Appl. No. 14/306,111, mailed Nov. 13, 2014.
Office Action in U.S. Appl. No. 29/497,888, mailed Nov. 19, 2014.
Office Action in U.S. Appl. No. 13/729,548, mailed Dec. 2, 2014.
Office Action in U.S. Appl. No. 13/684,113, mailed Dec. 15, 2014.
Office Action in U.S. Appl. No. 14/044,851, mailed Jan. 5, 2015.
Office Action in U.S. Appl. No. 13/485,900, mailed Feb. 3, 2015.
Office Action in U.S. Appl. No. 13/485,883, mailed Feb. 3, 2015.
Office Action in U.S. Appl. No. 14/304,671, mailed Feb. 4, 2015.
Notice of Allowance in U.S. Appl. No. 14/137,963, mailed Jan. 28, 2015.
Bell, S. et al., "Report on nutrient losses and gains factors used in European food composition databases", Technical Report, Apr. 2006, pp. 1-66.
Hugh, J. "Recipe Calculations: Where Do We Stand?", Proceedings of the 12th National Nutrient Databank Conference, Houston, Texas, Apr. 12, 1987, pp. 135-140 (Retrieved from the Internet on Feb. 13, 2015 at http://www.nutrientdataconf.org/PastConf/NDBC12/5-2_Joseph.pdf).
Valero, C., et al., "Design Guidelines for a Quality Assessment System of Fresh Fruits in Fruit Centers and Hypermarkets", Agricultural Engineering International: the CIGR Journal of Scientific Research and Development, vol. II, Aug. 2000, pp. 1-20.
PCT International Search Report and Written Opinion in International Application No. PCT/US2014/059186, mailed Dec. 22, 2014.
PCT International Search Report and Written Opinion in International Application No. PCT/US2014/045807, mailed Jan. 22, 2015.
Communication Pursuant to Article 94(3) in European Application No. 13731655.0, dated Jan. 22, 2015.
PCT International Search Report and Written Opinion in International Application No. PCT/US2014/064434, mailed Feb. 20, 2015.
Extended European Search Report in European Application No. 13751912.0, dated Feb. 25, 2015.
PCT International Search Report and Written Opinion in International Application No. PCT/US2014/033084, mailed Mar. 6, 2015.
PCT International Search Report and Written Opinion in International Application No. PCT/US2014/036570, mailed Mar. 10, 2015.
PCT International Search Report and Written Opinion in International Application No. PCT/US2014/065281, mailed Mar. 13, 2015.

* cited by examiner

ΔN Meter (represented through color change)

ΔN Meter (represented through percentage change)

LOGISTIC TRANSPORT SYSTEM FOR NUTRITIONAL SUBSTANCES

RELATED PATENT APPLICATIONS

This application is a continuation-in-part of U.S. patent application Ser. No. 14/051,379, filed Oct. 10, 2013, which is a continuation-in-part of U.S. patent application Ser. No. 13/485,854, filed May 31, 2012, which claims benefit under 35 U.S.C. 119(e) of U.S. Provisional Patent Application Ser. No. 61/624,948 filed Apr. 16, 2012; U.S. Provisional Patent Application Ser. No. 61/624,972, filed Apr. 16, 2012; and U.S. Provisional Patent Application, 61/624,985, filed Apr. 16, 2012, the contents of which are incorporated herein by reference in their entirety.

FIELD OF THE INVENTION

The present inventions relate to collection, transmission, creation and use of information regarding preservation of nutritional substances during logistic transport.

BACKGROUND OF THE INVENTION

Nutritional substances are traditionally grown (plants), raised (animals) or synthesized (synthetic compounds). Additionally, nutritional substances can be found in a wild, non-cultivated form, which can be caught or collected. While the collectors and creators of nutritional substances generally obtain and/or generate information about the source, history, caloric content and/or nutritional content of their products, they generally do not pass such information along to the users of their products. Further, there is no information available to the consumer regarding changes in nutritional, organoleptic, or aesthetic values of nutritional substances or regarding residual nutritional, organoleptic, or aesthetic values of the nutritional substance after they have been conditioned, and no way for the consumer to know what conditioning protocol will achieve the nutritional, organoleptic, or aesthetic values he desires. It would be desirable for such information be available to the consumers of nutritional substances at any desired moment, as well as all participants in the food and beverage industry—the nutritional substance supply system. An interactive system and data base, including user-friendly dynamic nutritional substance labeling allowing consumers, and any other member of the nutritional substance supply system, to access information regarding changes in nutritional, organoleptic, or aesthetic values of a nutritional substance as well as creation and origin information for the nutritional substance, at any moment during the life-cycle of the nutritional substance up to the moment of consumption, would offer great value to the nutritional substance supply system.

The nutritional content, also referred to herein as nutritional value, of foods and beverages, as used herein, refers to the non-caloric content of these nutritional substances which are beneficial to the organisms which consume these nutritional substances. For example, the nutritional content of a nutritional substance could include vitamins, minerals, proteins, and other non-caloric components which are necessary, or at least beneficial, to the organism consuming the nutritional substances. Caloric content refers to the energy in nutritional substances, commonly measured in calories. The caloric content could be represented as sugars and/or carbohydrates in the nutritional substances.

Consumers are starting to demand that the food and beverage industry offer products which include higher nutritional content, and/or at least information regarding the actual current nutritional content of such products, also referred to herein as the residual nutritional content. In fact, consumers are already willing to pay higher prices for higher nutritional content. This can be seen at high-end grocery stores which offer organic, minimally processed, fresh, non-adulterated nutritional substances. Further, as societies and governments seek to improve their constituents' health and lower healthcare costs, incentives and/or mandates will be given to the food and beverage industry to track, maintain, and/or increase the nutritional content of nutritional substances they handle. There will be a need for an industry-wide solution to allow the management of nutritional content across the entire cycle from creation to consumption. In order to manage the nutritional content of nutritional substances across the entire cycle from creation to consumption, the nutritional substance industry will need tools to identify, track, measure, estimate, preserve, transform, condition, record and communicate nutritional content information for nutritional substances. Providing nutritional substances with user friendly dynamic nutritional substance labeling facilitating this type of information connectivity and access will be a key in a system capable of such functionality. Of particular importance is the measurement, estimation, and tracking of changes in nutritional value, as well as changes in organoleptic and aesthetic values of a nutritional substance from creation to consumption. The changes in nutritional, organoleptic, and aesthetic values are individually and collectively referred to herein as $\Delta N$. This $\Delta N$ information could be used, not only by the consumer in selecting particular nutritional substances to consume, but could be used by the other food and beverage industry participants and modules, including creation, preservation, transformation, and conditioning, to make decisions on how to create, handle and process nutritional substances. Additionally, those who sell nutritional substances to consumers, such as restaurants and grocery stores, could communicate perceived qualitative values of the nutritional substance in their efforts to market and position their nutritional substance products. Further, a determinant of price of the nutritional substance could be particular nutritional, organoleptic, or aesthetic values, and if changes to those values, also referred to herein as $\Delta N$, are perceived as desirable. For example, if a desirable value has been maintained, improved, or minimally degraded, it could be marketed as a premium product. Still further, a system allowing creators, preservers and logistic transporters, transformers, conditioners, and consumers of nutritional substances to update labeling content to reflect the most current information about the nutritional substance would provide consumers with the information they need to make informed decisions regarding the nutritional substances they purchase and consume. Such information updates may include nutritional, organoleptic, or aesthetic values of the nutritional substance, may further include information regarding the source, creation and other origin information for the nutritional substance, and may further include information regarding adulteration of the nutritional substance.

For example, the grower of sweet corn generally only provides basic information as the variety and grade of its corn to the packager. Information regarding actual baseline nutritional, organoleptic, or aesthetic values of the corn is not likely to be provided, and no information is provided regarding $\Delta N$ values resulting from logistic transport (i.e. changes in nutritional, organoleptic, or aesthetic values resulting from preservation during bulk shipping to the packager). The packager, who preserves the corn and ships it to a transformer for use in a ready-to-eat dinner, may only tell the transformer that the corn has been frozen as loose kernels of sweet corn. No information is provided regarding baseline nutritional, organoleptic, or aesthetic values, ΔN values occurring prior to receipt by the packager, resulting from preservation and packaging by the packager, or resulting from logistic transport to the transformer. The transformer uses the corn as an ingredient in creating a ready-to-eat frozen dinner, and ships it to a supermarket. However, no information is provided to the supermarket regarding baseline nutritional, organoleptic, or aesthetic of the corn, ΔN values occurring prior to receipt by the transformer, resulting from transformation, or resulting from logistic transport to the supermarket (i.e. distribution via truck to the supermarket). The supermarket places the ready-to-eat dinner in a freezer located in the freezer isle of the supermarket, where it is selected by a consumer for purchase. However, no information on baseline nutritional, organoleptic, or aesthetic values, ΔN of such values, or corresponding residual nutritional, organoleptic, or aesthetic values of the ready-to-eat dinner is passed along to the consumer. The consumer knows essentially nothing about baseline nutritional, organoleptic, or aesthetic values of the corn, nor does the consumer know what changes occurred (generally a degradation, but could be a maintenance or even an improvement) to the nutritional, organoleptic, or aesthetic values, ΔN, of the sweet corn from creation, logistic transport to the packager, preservation and packaging by the packager, logistic transport to the transformer, transformation, logistic transport to the supermarket, and preservation in the supermarket's freezer isle. Further, the packaging of the ready-to-eat dinner may only provide the consumer with rudimentary instructions regarding how to cook or reheat the ready-to-eat dinner in a microwave oven, toaster oven or conventional oven, and only identify that the dinner contains whole kernel corn among the various items in the dinner, preparation by consumer, and finally consumption by the consumer. The consumer of the dinner will likely not express opinions on the quality of the dinner, unless it was an especially bad experience, where the consumer might contact the producer's customer support program to complain. Unfortunately, today consumers have no way to access information regarding the extent to which nutritional substances have changed, the ΔN (typically a degradation), at any moment during their lifecycle. Accordingly, they cannot determine the actual residual nutritional, organoleptic, or aesthetic values of the nutritional substance. Further, they have no access to information regarding how a nutritional substance's nutritional, organoleptic, or aesthetic values will further change (usually a degradation) during local storage and conditioning, and no way to access information regarding how to condition a nutritional substance in order to achieve desired residual nutritional, organoleptic, or aesthetic values. An interactive system and data base including user friendly dynamic nutritional substance labeling allowing consumers to access such information for nutritional substances would offer great value to the nutritional substance supply system.

Consumers' needs are changing as consumers are demanding healthier foods, such as "organic foods." Customers are also asking for more information about the nutritional substances they consume, such as specific characteristics' relating not only to nutritional content, but to allergens or digestive intolerances. For example, nutritional substances which contain lactose, gluten, nuts, dyes, etc. need to be avoided by certain consumers. However, the producer of the ready-to-eat dinner, in the prior example, has very little information to share other than possibly the source of the elements of the ready-to-eat dinner and its processing steps in preparing the dinner. Generally, the producer of the ready-to-eat dinner does not know the nutritional content and organoleptic state and aesthetic condition of the product after it has been reheated or cooked by the consumer, cannot predict changes to these properties, ΔN, and cannot inform a consumer of this information to enable the consumer to better meet their needs. For example, the consumer may want to know what proportion of desired organoleptic properties or values, desired nutritional content or values, or desired aesthetic properties or values of the corn in the ready-to-eat dinner remain after cooking or reheating, and the change in the desired nutritional content or values, the desired organoleptic properties or values, or the desired aesthetic properties or values, ΔN, (usually a degradation, but could be a maintenance or even improvement). There is a need to preserve, measure, estimate, store and/or transmit information regarding such nutritional, organoleptic, and aesthetic values, including changes to these values, ΔN, throughout the nutritional substance supply system.

The caloric and nutritional content information for a prepared food that is provided to the consumer is often minimal. For example, when sugar is listed in the ingredient list, the consumer may not receive any information about the source of the sugar, which can come from a variety of plants, such as sugarcane, beets, or corn, which will affect its nutritional content. Conversely, some nutritional information that is provided to consumers is so detailed, the consumer can do little with it. For example, this list of ingredients is from a nutritional label on a consumer product: Vitamins—A 355 IU 7%, E 0.8 mg 4%, K 0.5 mcg, 1%, Thiamin 0.6 mg 43%, Riboflavin 0.3 mg 20%, Niacin 6.0 mg 30%, B6 1.0 mg 52%, Foliate 31.5 mcg 8%, Pantothenic 7%; Minerals Calcium 11.6 1%, Iron 4.5 mg 25%, Phosphorus 349 mg 35%, Potassium 476 mg 14%, Sodium 58.1 mg 2%, Zinc 3.7 mg 24%, Copper 0.5 mg 26%, Manganese 0.8 mg 40%, Selenium 25.7 mcg 37%; Carbohydrate 123 g, Dietary fiber 12.1 g, Saturated fat 7.9 g, Monosaturated Fat 2.1 g, Polysaturated Fat 3.6 g, Omega 3 fatty acids 108 g, Omega 6 fatty acids 3481, Ash 2.0 g and Water 17.2 g. (%=Daily Value). There is a need for dynamic labeling of nutritional substances in order to provide information about nutritional substances in a meaningful manner. Such information needs to be presented in a manner that meets the specific needs of a particular consumer. For example, consumers with a medical condition, such as diabetes, would want to track specific information regarding nutritional values associated with sugar and other nutrients in the foods and beverages they consume, and would benefit further from knowing changes in these values or having tools to quickly indicate or estimate these changes in a retrospective, current, or prospective fashion.

In fact, each module in the food and beverage industry already creates and tracks some information, including caloric and nutritional information, about their product internally. For example, the farmer who grew the corn knows the variety of the seed, condition of the soil, the source of the water, the fertilizers and pesticides used, the chosen mode of logistic transport to the packager, and can measure the caloric and nutritional content at creation. The packager of the corn knows when it was picked, how the corn was preserved and packaged before being sent to the ready-to-eat dinner, what resulting change (typically a degradation) to caloric and nutritional content has occurred, the chosen mode of logistic transport to the transformer, and when it was delivered to the ready-to-eat dinner transformer. The ready-to-eat dinner transformer knows the source of the corn and other ingredients of the ready-to-eat dinner, how it was processed during transformation, including the recipe followed, how it was preserved and packaged for the consumer, and the chosen mode of logistic transport to the supermarket. Not only does such a ready-to-eat dinner producer know what changes (typically degradation) to caloric and nutritional content occurred, the ready-to-eat dinner transformer can modify its processing and post-processing preservation to optimize residual nutritional, organoleptic, and aesthetic values (for example to minimize degradation). The supermarket knows when they received the ready-to-eat dinners, when they were put into their freezer in the freezer isle, the temperature and other conditions inside the freezer, and when the consumer purchased the ready-to-eat dinner. Finally, the consumer knows how she locally stored and prepared the ready-to-eat dinner for consumption, which can also change the nutritional, organoleptic, and aesthetic values (typically a degradation), what condiments were added, and whether she did or did not enjoy it.

If there was a mechanism to share this information, the quality of the nutritional substances, including caloric and nutritional, organoleptic, and aesthetic value, could be preserved and improved. Consumers could be better informed about nutritional substances they select and consume, including the state, and changes in the state, $\Delta N$, of the nutritional substance throughout its lifecycle from creation to consumption. The efficiency and cost effectiveness of nutritional substances could also be improved. Feedback within the entire chain from creator to consumer could provide a closed-loop system that could improve quality (taste, appearance, and caloric and nutritional content), efficiency, value and profit. For example, in the milk supply chain, at least 10% of the milk produced is wasted due to safety margins included in product expiration dates. The use of more accurate tracking information, measured quality information, including $\Delta N$ and corresponding residual nutritional, organoleptic, and aesthetic values, and historical environmental information could substantially reduce such waste. An interactive system and data base including dynamic nutritional substance labeling for collecting, preserving, measuring and/or tracking information about a nutritional substance in the nutritional substance supply system, would allow needed accountability. There would be nothing to hide. Unfortunately, today there is no such system or dynamic nutritional substance labeling.

As consumers are demanding more information about what they consume, they are asking for products that have higher nutritional content and more closely match good nutritional requirements, and would like nutritional products to actually meet their specific nutritional substance requirements. While grocery stores, restaurants, and all those who process and sell food and beverages may obtain some information from current nutritional substance tracking systems, such as existing non-dynamic nutritional substance labeling, these current systems can provide only limited information.

Current packaging materials for nutritional substances include plastics, paper, cardboard, glass, and synthetic materials. Generally, the packaging material is chosen by the producer to best preserve the quality of the nutritional substance until used by the customer. In some cases, the packaging may include some information regarding type of nutritional substance, identity of the producer, and the country of origin. Such packaging generally does not transmit source information of the nutritional substance, such as creation information and baseline nutritional, organoleptic, and aesthetic values, current or historic information as to the external conditions of the packaged nutritional substance during storage or logistic transport, current or historic information as to the internal conditions of the packaged nutritional substance during storage or logistic transport, or corresponding $\Delta N$ information and residual nutritional, organoleptic, or aesthetic values.

Nutritional substance collectors and/or producers, such as growers (plants), ranchers (animals) or synthesizer (synthetic compounds), routinely create and collect information about their products, however, that information is generally not accessible by their customers. Even if such producers wished to provide such information to their customers, there is no current method of labeling, encoding or identifying each particular product to provide such information (even though all plants, animals and in general, nutritional substances have a natural fingerprint). While there are limited methods and systems available, they are excessively costly, time consuming, and do not trace, or provide access to, the nutritional, organoleptic, and/or aesthetic state across the product's lifecycle. Current labels for such products include package labels, sticker labels and food color ink labels. These labels generally are applied to all similar products and cannot identify each particular product, only variety of products, such as apple banana, but not a particular banana.

An important issue in the creation, preservation, transformation, conditioning, and consumption of nutritional substances are the changes in nutritional, organoleptic, or aesthetic values, $\Delta N$, that occur in nutritional substances due to a variety of internal and external factors. Because nutritional substances are composed of biological, organic, and/or chemical compounds, they are generally subject to degradation. This degradation generally reduces the nutritional, organoleptic, and/or aesthetic values of nutritional substances. While not always true, nutritional substances are best consumed at their point of creation. However, being able to consume nutritional substances at the farm, at the slaughterhouse, at the fishery, or at the food processing plant is at least inconvenient, if not impossible. Currently, the food and beverage industry attempts to minimize the loss of nutritional value (often through the use of additives or preservatives), and/or attempts to hide this loss of nutritional value from consumers.

It is understood that nutritional substances may experience one, or several, preservation modalities on their journey from creation to consumption. Such preservation modalities include all known forms of storage. Further, such preservation modalities include all known forms of logistic transport. Modes of logistic transport may include, but are in no way limited to: containers for maritime, rail, highway, and airfreight; enclosed tractor-trailers; box trucks; rail and highway tankers; hoppers; pallets; boxes; bags; drums; and so forth. $\Delta N$ resulting during logistic transport of nutritional substances can be significant. Accordingly, the ability to track $\Delta N$ (or corresponding residual nutritional, organoleptic, or aesthetic values) resulting during logistic transport and communicate it to others in the nutritional substance supply system would provide a great benefit to all participants in the nutritional substance supply system.

Overall, the examples herein of some prior or related systems and their associated limitations are intended to be illustrative and not exclusive. Other limitations of existing or prior systems will become apparent to those of skill in the art upon reading the following Detailed Description.

OBJECTS OF THE INVENTION

In an object of the present invention, a nutritional substance is preserved such that its source information and historical preservation information, including information regarding storage, packaging, logistic transport, and any other external influences on the nutritional substance which may have caused changes in nutritional, organoleptic, and/or aesthetic values of the nutritional substance, herein collectively and individually referred to as ΔN, and information regarding such ΔNs or a resulting residual nutritional, organoleptic, and/or aesthetic value, are available to users and/or consumers of the nutritional substance, as well as all entities of the nutritional substance supply system, including those who create, transform, preserve and provide logistic transport, and condition nutritional substances.

In a further object of the present invention, preservation systems, including packaging, storage systems and containers, and logistic transport, can dynamically interact with a nutritional substance being preserved, in order to maintain and/or improve and/or minimize degradation of the nutritional substance in order to maintain, improve, or minimize degradation of a nutritional, organoleptic, and/or aesthetic value, or otherwise favorably influence a ΔN related to the nutritional substance.

In an object of the present invention, a nutritional substance is preserved such that its source information and/or historical preservation information, including information regarding storage, packaging, logistic transport, and any other external influences on the nutritional substance which may have caused changes in nutritional, organoleptic, and/or aesthetic values of the nutritional substance, herein collectively and individually referred to as ΔN, and information regarding such ΔNs or a resulting residual nutritional, organoleptic, and/or aesthetic value, are available to entities outside of the nutritional substance supply system.

In an object of the present invention, the packaging or label of a nutritional substance tracks creation and historical information of nutritional substance, including ΔN information as well as current information about the state of a nutritional, organoleptic, and/or aesthetic value of the nutritional substance.

In an object of the present invention, a unique attribute of a nutritional substance tracks creation and historical information of nutritional substance, including ΔN information as well as current information about the state of a nutritional, organoleptic, and/or aesthetic value of the nutritional substance.

In a further object of the present invention, preservation systems, including storage, packaging and logistic transport, can dynamically interact with a nutritional substance to maintain and/or improve and/or minimize degradation of the nutritional substance being preserved, in order to maintain, improve, or minimize degradation of a nutritional, organoleptic, and/or aesthetic value, or otherwise favorably influence a ΔN related to the nutritional substance, and transmit information regarding such dynamic interaction with the nutritional substance.

In an object of the present invention, a nutritional substance is preserved such that its source information and/or historical preservation information, including information regarding storage, packaging, logistic transport, and any other external influences on the nutritional substance which may have caused changes in nutritional, organoleptic, and/or aesthetic values of the nutritional substance, herein collectively and individually referred to as ΔN, and information regarding such ΔNs or a resulting residual nutritional, organoleptic, and/or aesthetic value, are available by reference to a unique identifier provided with the nutritional substance.

In an object of the present invention, ΔN information of a nutritional substance is referenced to a unique identifier associated with the nutritional substance and the ΔN information is tracked and/or collected and/or stored and/or minimized and/or transmitted.

SUMMARY OF THE INVENTION

In an embodiment of the present invention, a preservation system for a nutritional substance, including, but not limited to, storage, packaging, and logistic transport systems, may allow the tracking of source information, information as to the history of the nutritional substance from the point it was preserved and/or current information on external influences on the preserved nutritional substance which may have caused changes in nutritional, organoleptic, and/or aesthetic values of the nutritional substance, herein collectively and individually referred to as ΔN. In a further embodiment, the current information on the external influences on the preserved nutritional substance is utilized to provide ΔN values or resulting residual nutritional, organoleptic, and/or aesthetic values to users and/or consumers of the nutritional substance as well as all entities of the nutritional substance supply system, including those who create, preserve (including logistic transport), transform, condition, and consume nutritional substances.

In an embodiment of the present invention, packaging or labeling for a nutritional substance can facilitate the provision of information to any entity inside or outside of the nutritional substance supply system, but preferably the consumer, related to a ΔN value or resulting residual nutritional, organoleptic, and/or aesthetic value of the nutritional substance.

In an embodiment of the present invention, a unique attribute of a nutritional substance can facilitate the provision of information to any entity inside or outside of the nutritional substance supply system, but preferably the consumer, related to a ΔN value or resulting residual nutritional, organoleptic, and/or aesthetic value of the nutritional substance.

In an embodiment of the present invention, a preservation system for a nutritional substance, including, but not limited to, storage, packaging and logistic transport systems, may dynamically interact with the nutritional substance to maintain, improve, or minimize degradation of a nutritional, organoleptic, and/or aesthetic value, or otherwise favorably influence a ΔN related to the nutritional substance.

In an embodiment of the present invention, a preservation system for a nutritional substance, including, but not limited to, storage, packaging and logistic transport systems, may allow the tracking of source information, information as to the history of the nutritional substance from the point it was preserved and/or current information on external influences on the preserved nutritional substance which may have caused changes in nutritional, organoleptic, and/or aesthetic values of the nutritional substance, herein collectively and individually referred to as ΔN. In a further embodiment, the current information on the external influences on the preserved nutritional substance is utilized to provide ΔN values or resulting residual nutritional, organoleptic, and/or aesthetic values to entities outside of the nutritional substance supply system.

In an embodiment of the present invention, packaging or labeling for a nutritional substance references information related to a ΔN value or resulting residual nutritional, organoleptic, and/or aesthetic value of the nutritional substance by a unique identifier provided by the packaging or labeling for the nutritional substance. Alternatively, information related to a ΔN value or resulting residual nutritional, organoleptic, and/or aesthetic value of the nutritional substance may be referenced by a unique property of the nutritional substance. Such packaging or labeling may be applicable to nutritional substances that are preserved individually or in bulk.

In an embodiment of the present invention, a preservation system for a nutritional substance, including, but not limited to, storage, packaging, and logistic transport systems, can dynamically interact with the nutritional substance to maintain, improve, or minimize degradation of a nutritional, organoleptic, and/or aesthetic value, or otherwise favorably influence a ΔN related to the nutritional substance, and transmits information related to the interaction, the ΔN, or the corresponding residual nutritional, organoleptic, or aesthetic value.

In an embodiment of the present invention, a preservation system for a nutritional substance, including, but not limited to, storage, packaging, and logistic transport systems, can allow the tracking of source information, information as to the history of the nutritional substance from the point it was preserved and/or current information on external influences on the preserved nutritional substance which may have caused changes in nutritional, organoleptic, and/or aesthetic values of the nutritional substance, herein collectively and individually referred to as ΔN. In a further embodiment of the present invention, the current information on the external influences on the preserved nutritional substance is referenced to a unique identifier provided with the preservation system, or a property unique to the nutritional substance. Such a unique identifier may be applicable to nutritional substances that are preserved individually or in bulk.

In an embodiment of the present invention, a system is provided for the creation, collection, storage, transmission, and/or processing of information regarding a dynamically labeled nutritional substance so as to improve, maintain, or minimize degradation of nutritional, organoleptic, and/or aesthetic value of the nutritional substance. Additionally, such information may be provided for use by creators, preservers (including logistic transporters), transformers, conditioners, and consumers of the nutritional substance. In a preferred embodiment, this information is openly available and openly integrated at any point in time to all constituents in the nutritional substance supply system. It is preferred that dynamic labeling provided with the nutritional substance enables the integration and availability of the information and that this information becomes openly available and openly integrated as soon as it is created. The nutritional information creation, preservation, and transmission system of the present invention may allow the nutritional substance supply system to improve its ability to minimize degradation of nutritional, organoleptic and/or aesthetic value of the nutritional substance, and/or inform the consumer, creator, preserver (including logistic transporter), transformer, conditioner, or consumer about such degradation, or ΔN. While the ultimate goal of the nutritional substance supply system can be to minimize degradation of nutritional, organoleptic and/or aesthetic values, or as it relates to ΔN, minimize the negative magnitude of ΔN, an interim goal may be providing consumers with significant information regarding any change, particularly degradation, of nutritional, organoleptic and/or aesthetic values of nutritional substances, and/or component nutritional substances thereof, consumers select and consumer, the ΔN, such that desired information regarding specific residual nutritional, organoleptic, and/or aesthetic values can be ascertained using the ΔN. Entities within the nutritional substance supply system that provide such ΔN information regarding nutritional substances, particularly regarding degradation, will be able to differentiate their products from those who obscure and/or hide such information. Additionally, such entities should be able to charge a premium for products which either maintain their nutritional, organoleptic, and/or aesthetic value, or supply more complete information about changes in their nutritional, organoleptic, and/or aesthetic value, the ΔN.

In another aspect, embodiments of the present invention further provide a logistic transport system for preservation of nutritional substances comprised of a mobile container for preserving a nutritional substance associated with a unique identifier. The mobile container includes a gas sensor and an optical sensor for dynamically sensing attribute information of the nutritional substance indicating a change in value of a specific nutritional or organoleptic property; and a temperature and humidity sensor for dynamically sensing environmental information of the container indicating a change in value of the specific nutritional or organoleptic property. A device is provided to dynamically provide location, date, and time information, and information storage is provided for storing the dynamically sensed attribute information, the environmental information, the location, date and time information, and the unique identifier.

In some embodiments, a method is provided for determining and communicating an evolution of a particular nutritional or organoleptic property of a nutritional substance, comprising scanning a nutritional substance provided with a unique identifier at a first time to obtain a first scan-response related to a target attribute associated with a particular nutritional or organoleptic property. The first scan-response is analyzed and correlated with a first value of the particular nutritional or organoleptic property and to the unique identifier. The nutritional substance is scanned at a subsequent time to obtain a subsequent scan-response related to the target attribute. The subsequent scan-response is analyzed and correlated with a subsequent value of the particular nutritional or organoleptic property and to the unique identifier. A change is determined in the particular nutritional or organoleptic property_between the first time and the subsequent time, and information related to the change in the particular nutritional or organoleptic property referenced to the unique identifier is communicated.

Other advantages and features will become apparent from the following description and claims. It should be understood that the description and specific examples are intended for purposes of illustration only and not intended to limit the scope of the present disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
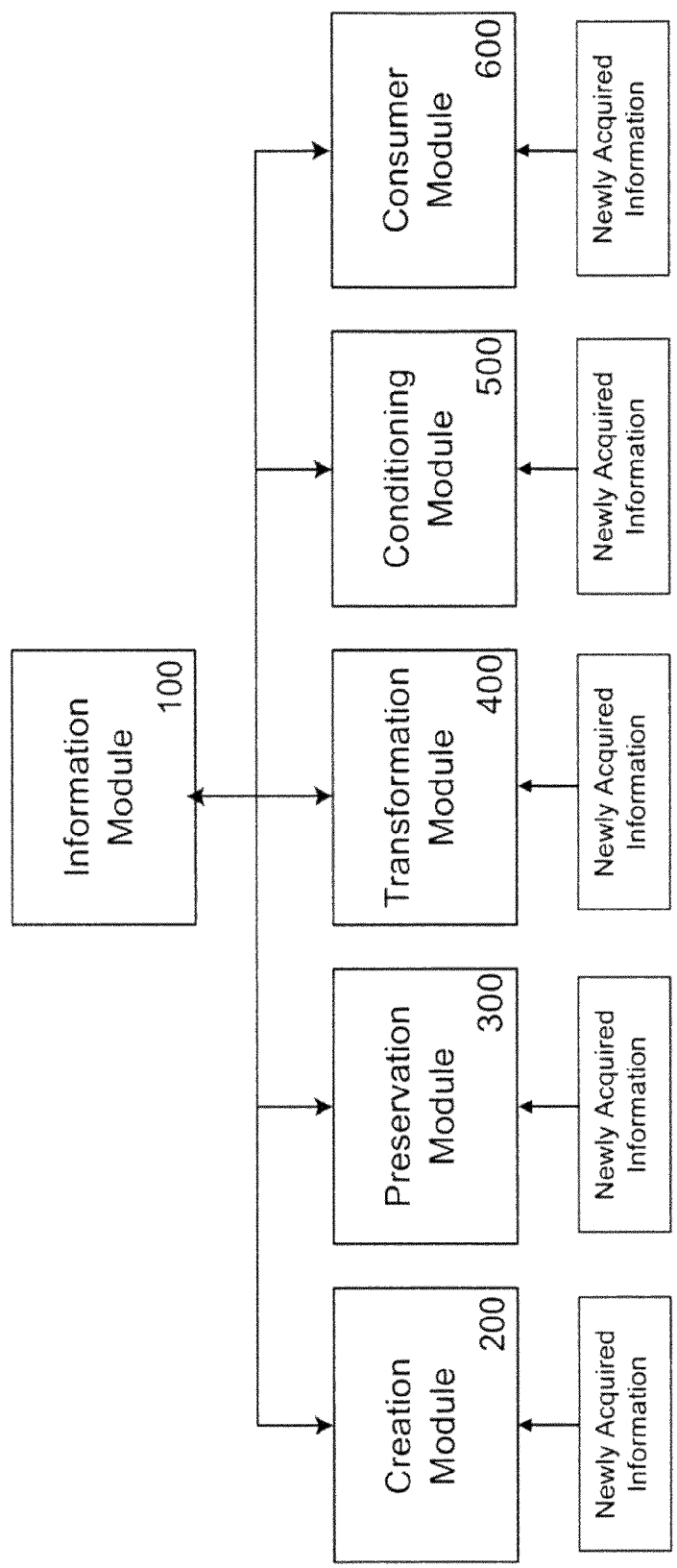
FIG. 1 shows a schematic functional block diagram of a nutritional substance supply relating to the present invention.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION OF THE INVENTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

The following discussion provides a brief, general description of a representative environment in which the invention can be implemented. The present invention enables a nutritional substance to interact and communicate with its preservation system in a dynamic manner through the natural changes $\Delta N$ it experiences, and further enables the preservation system to convey information associated with those changes to the consumer. As used herein, preservation modules, also referred to as preservation systems, may include, but are not limited to, any internal or external portion of a nutritional substance package, container, carton, bottle, bulk storage system, logistic transport system, box, bag, vessel, cup, plate, wrapper, label, or any other apparatus used to preserve, store, transfer, present, or serve a nutritional substance.

An example of the present invention is provided of bottled wine interacting, or communicating, with a portion of its container. As the wine in the container ages it naturally experiences many changes $\Delta N$, including changes in acidity, tannin content, gas emission, sugar content, alcohol content, and others, which occur at various rates depending on factors intrinsic to the wine, for example the variety of grape, and further depending on factors extrinsic to the wine, such as container materials, storage temperature, exposure to light, exposure to oxygen, and any other environmental conditions that may occur in an embodiment, at least a portion of the container contacting the wine, such as a cork, a cap, a submerged coupon or indicator, or any part of the surface of the bottle contacting the wine can monitor one or more $\Delta N$ and convey to a consumer at least one of the $\Delta N$, a corresponding rate of change of the $\Delta N$, or a corresponding current state (corresponding current nutritional, organoleptic, or aesthetic value), of the wine at any moment the consumer wants to know, such as when he is deciding to purchase or open the container.

A container may be provided with the ability to variably adapt its internal environment in response to the monitored $\Delta N$ information, so as to alter the corresponding rate of change of the monitored $\Delta N$. In one embodiment, a means for variably adapting conditions in the container to alter the rate of change of a monitored $\Delta N$ includes at least one of a chemical, photochemical, mechanical, hydraulic, pneumatic, dissolution, absorption, swelling, shrinkage, component addition, component subtraction, component binding, component conversion, electrolytic, ionic, osmotic, reverse osmotic, or thermal means to variably control the gaseous environment in the container in response to monitoring of the gaseous environment in the container.

In another example, a milk carton containing milk could have a small area on its side with encapsulated gel in direct contact with the milk. As the milk ages, its bacteria count naturally increases, also resulting in a reduced ph. The bacteria will be able to penetrate the gel and the gel will gradually change color in response to the increasing bacteria content or concentration, indicating the increase in bacteria within the milk, and therefore a current state of the milk. For example, the gel may change from green, wherein green represents an acceptable bacteria level and associated shelf life, to yellow, wherein yellow represents a higher acceptable bacteria level and associated shorter shelf life, to red, wherein red represents the milk has an unacceptably high bacteria level and is not apt for drinking any more.

Alternatively, the gel may gradually change color in response to a reduction in pH, wherein changes in pH are surrogates for changes in bacteria levels. As the milk ages, its bacteria count naturally increases, reducing its pH. For example, the gel may change from green, wherein green represents a pH level corresponding to an acceptable bacteria level and associated shelf life, to yellow, wherein yellow represents a lower pH level and corresponding higher acceptable bacteria level and associated shorter shelf life, to red, wherein red represents a still lower pH and corresponding unacceptably high bacteria level and is not apt for drinking any more.

It is understood that nutritional substances, as used herein, include, but are not limited to, synthetic compounds such as medicaments, supplements, and other substances intended for consumption or introduction into a consumer. The present invention may include embodiments wherein a portion of the nutritional substance interacting or communicating with its container is segregated from a portion of the nutritional substance to be consumed. This would be of particular benefit for packaged goods including synthetic compounds such as medicaments, in which case it would be desirable to segregate the portion of medicament interacting or communicating with the container from the portion of the medicament for consumption. In this case, the portion of the medicament interacting or communicating with the container would serve as a parallel sample of the medicament provided for consumption. This might be accomplished by providing a separate, permanently sealed cavity on or within the medicament container, its cover, its label, or any permanently sealed cavity structure known in the art, wherein the structure contains the portion of medicament intended to interact or communicate with the container. The permanently sealed cavity can interact with the portion of medicament communicating with it to convey desired $\Delta N$ information regarding the medicament. Such $\Delta N$ information may be associated with a degradation of the medicament, a residual value of the medicament, an expiration date of the medicament, or utilized in any other way to ensure the medicament's safety and efficacy when a consumer uses it.

Other examples of the present invention could include, but are not limited to, containers like jars, glasses, or cups that could detect when there is an unhealthy level of toxins, antibiotics, fungus, bacteria, pesticides, or other undesirable components in tap water intended for consumption, or if the coffee poured into a cup has caffeine or not. The principle at work is that of symbiosis, similar to that which occurs between a banana and its peel. The banana peel has a natural evolution from green to black that conveys the level of maturity of the banana. The peel reacts to the natural $\Delta N$ that occurs during the banana's maturation process, wherein the $\Delta N$s may include changes in acidity, sugar content, and bacteria level. The $\Delta N$s of the banana independently and collectively have an effect on the aesthetic values of the banana peel, which in turn conveys to the consumer when and how the banana may best be consumed. For example, a green peel indicates that the banana is not yet ripe and should not be eaten. Yellow indicates that it may be suitable for consumption, but will not be very sweet. Yellow with a few black spots indicates that it is suitable for consumption, and will be sweat. Mostly black indicates that it is suitable for use in baked goods or to be fried. Very black indicates that it is no longer suitable for consumption. In this same manner when the peel has been punctured or torn and the maturating process is accelerated as more oxygen than normal contacts the banana, the banana peel quickly turns black alerting the consumer. Therefore the consumer does not have to rely on a static expiration date to determine the banana's suitability for consumption.

Although not required, aspects of the invention may be described below in the general context of computer-executable instructions, such as routines executed by a general-purpose data processing device (e.g., a server computer or a personal computer). Those skilled in the relevant art will appreciate that the invention can be practiced with other communications, data processing, or computer system configurations, including: wireless devices, Internet appliances, handheld devices (including personal digital assistants (PDAs)), wearable computers, all manner of cellular or mobile phones, multi-processor systems, microprocessor-based or programmable consumer electronics, set-top boxes, network PCs, mini-computers, mainframe computers, and the like. Indeed, the terms "controller," "computer," "server," and the like are used interchangeably herein, and may refer to any of the above devices and systems.

While aspects of the invention, such as certain functions, are described as being performed exclusively on a single device, the invention can also be practiced in distributed environments where functions or modules are shared among disparate processing devices. The disparate processing devices are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data related to the invention may be distributed over the Internet or over other networks (including wireless networks), on a propagated signal on a propagation medium (e.g., an electromagnetic wave(s), a sound wave, etc.) over a period of time. In some implementations, the data may be provided on any analog or digital network (packet switched, circuit switched, or other scheme).

In some instances, the interconnection between modules is the internet, allowing the modules (with, for example, WiFi capability) to access web content offered through various web servers. The network may be any type of cellular, IP-based or converged telecommunications network, including but not limited to Global System for Mobile Communications (GSM), Time Division Multiple Access (TDMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), Worldwide Interoperability for Microwave Access (WiMAX), Universal Mobile Telecommunications System (UMTS), Evolution-Data Optimized (EVDO), Long Term Evolution (LTE), Ultra Mobile Broadband (UMB), Voice over Internet Protocol (VoIP), Unlicensed Mobile Access (UMA), etc.

The modules in the systems can be understood to be integrated in some instances and in particular embodiments, only particular modules may be interconnected.

FIG. 1 shows the components of a nutritional substance industry 10. It should be understood that this could be the food and beverage ecosystem for human consumption, but could also be the feed industry for animal consumption, such as the pet food industry. A goal of the present invention for nutritional substance industry 10 is to create, preserve, transform and trace change in nutritional, organoleptic and/or aesthetic values of nutritional substances, collectively and individually also referred to herein as $\Delta N$, through their creation, preservation (including logistic transport), transformation, conditioning and consumption. While the nutritional substance industry 10 can be composed of many companies or businesses, it can also be integrated into combinations of business serving many roles, or can be one business or even individual. Since $\Delta N$ is a measure of the change in a value of a nutritional substance, knowledge of a prior value (or state) of a nutritional substance and the $\Delta N$ value will provide knowledge of the changed value (or state) of a nutritional substance, and can further provide the ability to estimate a change in value (or state).

Module 200 is the creation module. This can be a system, organization, or individual which creates and/or originates nutritional substances. Examples of this module include a farm which grows sweet corn; a ranch which raises beef; an aquaculture farm for growing shrimp; a factory that synthesizes nutritional compounds; a collector of wild truffles; or a deep sea crab trawler.

Preservation module 300 is a preservation system (including storage and logistic transport systems) for preserving and protecting the nutritional substances that are created by one module and transferred to another module or entity. Once the nutritional substance has been created, generally, it will need to be packaged in some manner for its transition to other modules in the nutritional substances industry 10. Transition to other modules is commonly accomplished by some form of logistic transport. While preservation module 300 is shown in a particular position in the nutritional substance industry 10, following the creation module 200, it should be understood that the preservation module 300 actually can be placed anywhere nutritional substances need to be preserved during their transition from creation to consumption. For example, the creator of the sweet corn may choose enclosed, bulk non-refrigerated rail cars as a logistic transport modality for shipping his corn to a preserver. The preserver of the sweet corn may choose a package format comprising 50 lb boxes containing 10 ea individually sealed 5 lb plastic bags of frozen corn kernels shipped in refrigerated tractor trailers as a logistic transport modality for shipping his corn to a transformer.

Transformation module 400 is a nutritional substance processing system, such as a manufacturer who processes raw materials such as grains into breakfast cereals. In the example of the sweet corn kernels, the transformation module 400 could be a ready-to-eat frozen dinner manufacturer who receives the components, or ingredients, also referred to herein as component nutritional substances, for a ready-to-eat frozen dinner from preservation module 300 and prepares them into a frozen dinner. In this example, the transformer 400 receives the frozen sweet corn kernels from the preservation module 300 as 50 lb boxes containing 10 individually sealed 5 lb plastic bags of frozen corn kernels shipped in refrigerated tractor trailers. While transformation module 400 is depicted as one module, it will be understood that nutritional substances may be transformed by a number of transformation modules 400 on their path to consumption. In the example of the ready-to-eat dinner, the sweet corn is incorporated as an ingredient in ready-to-eat frozen dinners, and shipped to various supermarkets by the transformer's chosen logistic transport modality, which may be cartons containing 24 ready-to-eat frozen dinners each, delivered by the transformers chosen logistic transport modality, such as a refrigerated box truck. When the refrigerated box truck reaches a supermarket that has ordered the ready-to-eat frozen dinners, the product may be directly placed into the freezers of the frozen food isle, where it can be selected by a consumer.

Conditioning module 500 is a consumer preparation system for preparing the nutritional substance immediately before consumption by the consumer. Conditioning module 500 can be a microwave oven, a blender, a toaster, a convection oven, a cook, etc. It can also be systems used by commercial establishments to prepare nutritional substance for consumers such as a restaurant, an espresso maker, pizza oven, and other devices located at businesses which provide nutritional substances to consumers. Such nutritional substances could be for consumption at the business or for the consumer to take out from the business. Conditioning module 500 can also be a combination of any of these devices used to prepare nutritional substances for consumption by consumers. In the example of the ready-to-eat frozen dinner, the conditioning module typically may be the consumer's microwave oven or his convection oven.

Consumer module 600 collects information from the living entity which consumes the nutritional substance which has passed through the various modules from creation to consumption. The consumer can be a human being, but could also be an animal, such as pets, zoo animals and livestock, which are they themselves nutritional substances for other consumption chains. Consumers could also be plant life which consumes nutritional substances to grow. In the example of the ready-to-eat frozen dinner, the consumer is the individual who purchases, conditions, and consumes the ready-to-eat frozen dinner.

Information module 100 receives and transmits information regarding dynamically labeled nutritional substances between each of the modules in the nutritional substance industry 10 including, the creation module 200, the preservation module 300 (which includes logistic transport modalities), the transformation module 400, the conditioning module 500, and the consumer module 600. The nutritional substance information module 100 can be an interconnecting information transmission system which allows the transmission of information between various modules. It is preferred that the information module 100 collects, tracks, and organizes information regarding the dynamically-labeled nutritional substances from each stage of the production of the nutritional substances from creation to consumption and that the information regarding the dynamically-labeled nutritional substances is openly available and openly integrated at any point in time to all modules of the nutritional substance supply system, preferably as soon as it is created. The integration and availability of the information is enabled by dynamic labeling provided with the nutritional substances, which includes a unique nutritional substance identifier, also referred to herein as a dynamic information identifier. Information module 100 contains a database, also referred to herein as a dynamic nutritional value database, where the information regarding the dynamically labeled nutritional substance resides and can be referenced or located by the corresponding dynamic information identifier. The dynamic nutritional value database may comprise: one database openly accessible to all modules of the nutritional substance supply system, or one database wherein specific types of data are selectively accessible to particular modules of the nutritional substance supply system. For example, information regarding particular logistic transport information may only be available to the preservation module, or alternatively, may be available to the preservation module and at least one of the creation, transformation, conditioning, or consumer modules. Alternatively, the dynamic nutritional value database may comprise: multiple individual databases openly accessible to all modules of the nutritional substance supply system, or multiple individual databases wherein specific individual databases are selectively accessible to one or more particular modules of the nutritional substance supply system. For example, information regarding logistic transport may reside in a preservation database and may only be available to the preservation module, or alternatively, may be available to the preservation module and at least one of the creation, transformation, conditioning, or consumer modules. Information module 100 can be connected to the other modules by a variety of communication systems, such as paper, computer networks, and Internet and telecommunication systems, such as wireless telecommunication systems.

Figure 2:
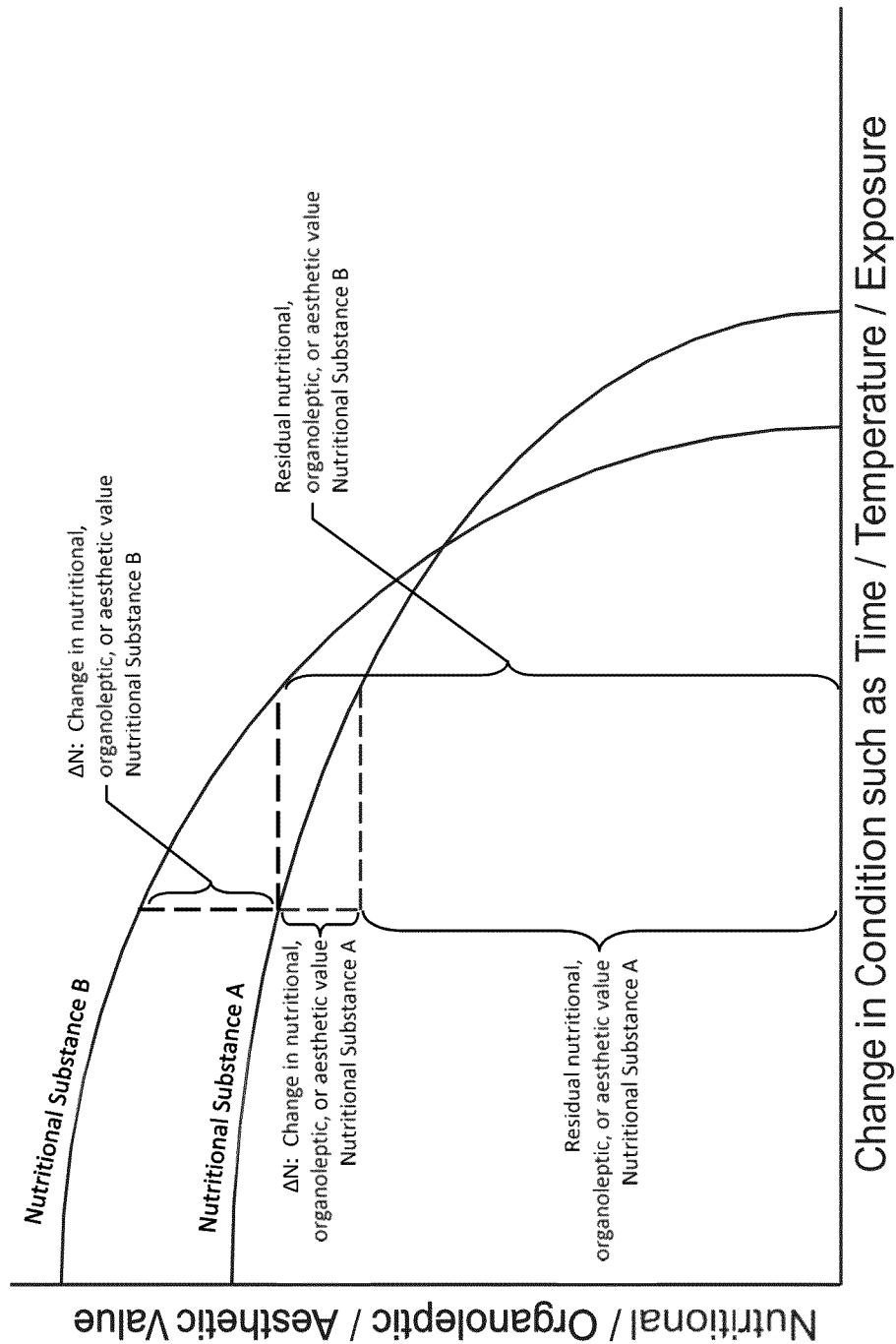
FIG. 2 shows a graph representing a value of a nutritional substance which changes according to a change of condition for the nutritional substance.

FIG. 2 is a graph showing the function of how a nutritional, organoleptic, or aesthetic value of a nutritional substance varies over the change in a condition of the nutritional substance. Plotted on the vertical axis of this graph can be a nutritional value, organoleptic value, or an aesthetic value of a nutritional substance (indicated as "Nutritional/Organoleptic/Aesthetic Value"). Plotted on the horizontal axis can be the change in a condition that the nutritional substance is exposed to, such as time, temperature, location, and/or exposure to environmental conditions (indicated as "Change in Condition such as Time/Temperature/Exposure). This exposure to environmental conditions can include, but is not limited to: exposure to air, including the air pressure and partial pressures of oxygen, carbon dioxide, water, or ozone; airborne chemicals, pollutants, allergens, dust, smoke, carcinogens, radioactive isotopes, or combustion byproducts; exposure to moisture; exposure to energy such as mechanical impact, mechanical vibration, irradiation, heat, or sunlight; elapsed time; or exposure to materials such as packaging. Also shown in FIG. 2 is ΔN for nutritional substance A and B (indicated as "ΔN: Change in nutritional, organoleptic, or aesthetic value") and the corresponding residual nutritional, organoleptic, or aesthetic value for nutritional substance A and B (indicated as "Residual nutritional, organoleptic, or aesthetic value"). The function plotted as nutritional substance A could show a ΔN for milk, such as the degradation of a nutritional value of milk during logistic transport by modality $L_1$. Any point on this curve can be compared to another point to measure and/or describe the change in nutritional value, or the ΔN of nutritional substance A, during logistic transport by modality $L_1$. The plot of the degradation in the same nutritional value of nutritional substance B, also milk, describes the change in nutritional value, or the ΔN of nutritional substance B, during logistic transport by modality $L_2$. As the graph shows, nutritional substance B starts out with a higher nutritional value than nutritional substance A, but degrades during logistic transport by modality $L_2$ more quickly than nutritional substance A during logistic transport by modality $L_1$.

In this example, where nutritional substance A and nutritional substance B are milk, this ΔN information regarding the nutritional substance degradation profile of each milk during logistic transport can be accessed and used by a transformer, such as a commercial homogenizer/bottler of milk, in the selection of the milk they wish to purchase for transformation, because nutritional substance A and nutritional substance B are provided with dynamic labeling, which includes a dynamic information identifier for each nutritional substance. Using the dynamic information identifier obtained from the dynamic labeling provided with each nutritional substance, the transformer could retrieve desired ΔN information, such as the nutritional substance degradation profile during logistic transport referenced to each of the milks, from a dynamic nutritional value database in information module 100. If the transformer has this information at time zero when selecting a milk product for purchase, the transformer could consider when the transformation of the milk will occur and whether that is on one occasion or multiple occasions. For example, if the transformer planned to transform all of the milk prior to the point when the curve represented by nutritional substance B crosses the curve represented by nutritional substance A, then the transformer would be likely to choose the milk represented by nutritional substance B because it has a higher nutritional value until it crosses the curve represented by nutritional substance A. However, if the transformer expects to transform at least some of the milk at a point in time after the time when the curve represented by nutritional substance B crosses the curve represented by nutritional substance A, then the transformer might choose to select the milk represented by the nutritional substance A, even though milk represented by nutritional substance A has a lower nutritional value than the milk represented by nutritional substance B at an earlier time. This change to a desired nutritional value in a nutritional substance, ΔN, over a change in a condition of the nutritional substance described in FIG. 2 can be measured and controlled throughout the nutritional substance supply system 10 in FIG. 1. This example demonstrates how dynamically generated information regarding a ΔN of a dynamically labeled nutritional substance, in this case a change in nutritional value of milk during logistic transport, can be used to understand a rate at which that nutritional value changes or degrades; when that nutritional value expires; and a residual nutritional value of the nutritional substance over a change in a condition of the nutritional substance, in this example a change during logistic transport. This ΔN information could further be used to determine a best-use date for nutritional substance A and B, which could be different from each other depending upon the dynamically generated information for each.

There is also the ΔN as two or more nutritional substances combine. For example, when lemon is added to guacamole it keeps the avocado in the guacamole from turning black. Referring again to FIG. 2, the function plotted as nutritional substance A could show a ΔN for guacamole made by a first transformer, such as the degradation of an aesthetic value of guacamole during logistic transport by modality $L_1$, in this case a degradation of its green color. Any point on this curve can be compared to another point to measure and/or describe the change in aesthetic value, or the ΔN of nutritional substance A during logistic transport by modality $L_1$. The plot of the degradation in the same aesthetic value of nutritional substance B, a guacamole made by a second transformer, describes the change in the same aesthetic value, or the ΔN, of nutritional substance B during logistic transport by the same modality $L_1$. Nutritional substance B starts out with a higher aesthetic value than nutritional substance A, but degrades during logistic transport by modality $L_1$ more quickly than nutritional substance A during logistic transport by modality $L_1$. The more rapid degradation of nutritional substance B during logistic transport by the same logistic transport modality $L_1$ is a consequence of the transformer of nutritional substance B adding less lemon juice to their guacamole in order not to distract from the flavor of the avocado. If nutritional substance A and nutritional substance B are provided with dynamic labeling, which may include a dynamic information identifier for each nutritional substance A and B referencing the information regarding the degradation of aesthetic values of the respective nutritional substances, a retailer making a purchasing decision regarding the nutritional substances A and B could retrieve desired ΔN information, such as the aesthetic degradation profile referenced to each guacamole, from a dynamic nutritional value database in information module 100. For example, if the retailer is purchasing the guacamole to sell at a time before the two curves intersect, and the decision is based on superior aesthetic value, the retailer is likely to choose nutritional substance B. If the retailer is purchasing the guacamole to sell after the time the two curves intersect, and the decision is based on superior aesthetic value, the retailer is likely to choose nutritional substance A, even though it has lower aesthetic value at the time of purchase.

In another example, lemon juice is added to sliced apples during processing to keep the sliced apples from turning black. The function plotted as nutritional substance A could show a ΔN for sliced apples processed by a particular transformer, such as the degradation of the aesthetic value of the sliced apples during logistic transport by modality $L_1$, in this case a degradation of its pale color. Any point on this curve can be compared to another point to measure and/or describe the change in aesthetic value, or the ΔN of nutritional substance A during logistic transport by modality $L_1$. The plot of the degradation in the same aesthetic value of nutritional substance B, a different lot of sliced apples processed by the same transformer using the same process, describes the same change in the aesthetic value, or the $\Delta N$, of nutritional substance B during logistic transport by modality $L_2$. Nutritional substance B starts out with a higher aesthetic value than nutritional substance A, but degrades during logistic transport more quickly than nutritional substance A, for instance because preservation conditions of logistic transport by modality $L_2$ result in more rapid degradation of similarly processed sliced apple's aesthetic value than the preservation conditions of logistic transport by modality $L_1$. The information available is related to the interaction of the apples and lemon juice during the respective logistic transport by modalities. If nutritional substance A and nutritional substance B are provided with dynamic labeling, which would include a dynamic information identifier for each nutritional substance, a retailer, such as a natural food market, can make purchasing decisions related to the aesthetic value of the sliced apples at a given point in time. Using the dynamic information identifier obtained from the dynamic labeling provided with each nutritional substance, the retailer could retrieve desired $\Delta N$ information, such as the aesthetic degradation profile referenced to the different lots of sliced apples shipped by logistic transport by modality $L_1$ and $L_2$, from a dynamic nutritional value database. For example, if the retailer is purchasing the sliced apples to sell before the time the two curves intersect, and the decision is based on superior aesthetic value, the retailer will likely choose nutritional substance B. If the retailer is purchasing the sliced apples and plans to sell at least some of them after the time the two curves intersect, and the decision is based on superior aesthetic value, the retailer may choose nutritional substance A, even though it has lower aesthetic value at the time of purchase.

In FIG. 1, Creation module 200 can dynamically encode nutritional substances, as part of the nutritional substance dynamic labeling, to enable the tracking of changes in nutritional, organoleptic, and/or aesthetic value of the nutritional substance, or $\Delta N$. This dynamic encoding, also referred to herein as a dynamic information identifier, can replace and/or complement existing nutritional substance marking systems such as barcodes, labels, and/or ink markings. This dynamic encoding, or dynamic information identifier, can be used to make nutritional substance information from creation module 200 available to information module 100 for use by preservation module 300 (which includes storage and logistic transport), transformation module 400, conditioning module 500, and/or consumption module 600, which includes the ultimate consumer of the nutritional substance. A key resource also available through module 100 is recipe information regarding meals that may utilize the nutritional substances as components. The $\Delta N$ information combined with recipe information from module 100 will not only be of great benefit to the consumer in understanding and accomplishing the nutritional, organoleptic, and aesthetic values desired, it will even help dispel misunderstandings that consumers may have about particular nutritional, organoleptic, and aesthetic values of nutritional substances or the combination or nutritional substances. One method of providing dynamically labeled nutritional substances with a dynamic information identifier by creation module 200, or any other module in nutritional supply system 10, could include an electronic tagging system, such as the tagging system manufactured by Kovio of San Jose, Calif., USA. Such thin film chips can be used not only for tracking nutritional substances, but can include components to measure attributes of nutritional substances, and record and transmit such information. Such information may be readable by a reader including a satellite-based system. Such a satellite-based nutritional substance information tracking system could comprise a network of satellites with coverage of some or all the surface of the earth, so as to allow the dynamic nutritional value database of information module 100 real time, or near real time updates about a $\Delta N$ of a particular nutritional substance. In turn, this information is openly available and openly integrated at any point in time to all constituents in the nutritional substance supply system. It is also preferred that this information becomes openly available and openly integrated as soon as it becomes available.

Preservation module 300 includes packers and shippers (also referred to herein as logistic transporters) of nutritional substances. The tracking of changes in nutritional, organoleptic, and/or aesthetic values, or a $\Delta N$, during the preservation period within preservation module 300 allows for dynamic expiration dates for nutritional substances. For example, expiration dates for dairy products are currently based generally only on time using assumptions regarding minimal conditions at which dairy products are maintained. This extrapolated expiration date is based on a worst-case scenario for when the product becomes unsafe to consume during the preservation period. In reality, the degradation of dairy products may be significantly less than this worst-case. If preservation module 300 could measure or derive the actual degradation information such as $\Delta N$, an actual expiration date, referred to herein as a dynamic expiration date, can be determined dynamically, and could be significantly later in time than an extrapolated expiration date. This would allow the nutritional substance supply system to dispose of fewer products due to expiration dates. This ability to dynamically generate expiration dates for nutritional substances is of particular significance when nutritional substances contain few or no preservatives. Such products are highly valued throughout nutritional substance supply system 10, including consumers who are willing to pay a premium for nutritional substances with few or no preservatives. Consumers of nutritional substances provided with dynamic labeling comprising dynamic information identifiers can readily access information regarding dynamic expiration dates for the nutritional substances, and such dynamic expiration dates could take into consideration changes in nutritional, organoleptic, and aesthetic values occurring during logistic transport.

It should be noted that a dynamic expiration date need not be indicated numerically (i.e., as a numerical date) but could be indicated symbolically as by the use of colors—such as green, yellow and red employed on semaphores—or other designations. In those instances, the dynamic expiration date would not be interpreted literally but, rather, as a dynamically-determined advisory date. In practice a dynamic expiration date will be provided for at least one component of a single or multi-component nutritional substance. For multi-component nutritional substances, the dynamic expiration date could be interpreted as a "best" date for consumption or "best-use" date for particular components. Consumers of nutritional substances provided with dynamic labeling comprising dynamic information identifiers could readily access this type of information regarding dynamic expiration dates for the nutritional substances, even taking into consideration changes in nutritional, organoleptic, and aesthetic values occurring during logistic transport. It is understood that all entities in the nutritional substance supply system can access such information.

By law, in many localities, food processors such as those in transformation module 400 are required to provide nutritional substance information regarding their products. Often, this information takes the form of a nutritional table applied to the packaging of the nutritional substance. Currently, the information in this nutritional table is based on averages or minimums for their typical product. Using the nutritional substance information from information module 100 provided by creation module 200, preservation module 300, and/or information from the transformation of the nutritional substance by transformation module 400, the food processor could include a dynamically generated nutritional value table, also referred to herein as a dynamic nutritional value table, for the actual dynamically-labeled nutritional substance being supplied. The information in such a dynamic nutritional value table could be used by conditioning module 500 in the preparation of the dynamically-labeled nutritional substance, and/or used by consumption module 600, so as to allow the ultimate consumer the ability to select the most desirable dynamically-labeled nutritional substance which meets their needs, and/or to track information regarding dynamically-labeled nutritional substances consumed. It is understood that nutritional substances may experience more than one preservation or more than one transformation on their journey from creation to consumption, and it is further understood that the nutritional substance information from information module 100 may be openly available to all modules including creation module 200, preservation module 300 (including logistic transport), transformation module 400, conditioning module 500, and consumer module 600.

Information about changes in nutritional, organoleptic, and/or aesthetic values of nutritional substances, or $\Delta N$, is particularly useful in the conditioning module 500 of the present invention, as it allows knowing, or estimating, the pre-conditioning state of the nutritional, organoleptic, and/or aesthetic values of the dynamically labeled nutritional substance, and allows for estimation of a $\Delta N$ associated with proposed conditioning parameters. The conditioning module 500 can therefore create conditioning parameters, such as by modifying existing or baseline conditioning parameters, which can exist as recipes and conditioning protocols available through the information module 100 or may be available locally available through the conditioning module 500, to deliver desired nutritional, organoleptic, and/or aesthetic values after conditioning. The pre-conditioning state of the nutritional, organoleptic, and/or aesthetic value of a nutritional substance is not tracked or provided to the consumer by existing information systems or conditioners, nor is the $\Delta N$ expected from a proposed conditioning tracked or provided to the consumer either before or after conditioning. However, using information provided by information module 100 from creation module 200, preservation module 300 (including logistic transport), transformation module 400, and/or information measured or generated by conditioning module 500 and/or consumer information from the consumer module 600, conditioning module 500 could provide the consumer with the actual, and/or estimated change in nutritional, organoleptic, and/or aesthetic values of a dynamically-labeled nutritional substance, or $\Delta N$. Such information regarding the change to nutritional, organoleptic and/or aesthetic value of the dynamically-labeled nutritional substance, or $\Delta N$, could be provided not only to the consumer, but could also be provided to information module 100 for use by creation module 200, preservation module 300 (including logistic transport), transformation module 400, so as to track, and possibly improve nutritional substances throughout the entire nutritional substance supply system 10.

The information regarding nutritional substances provided by information module 100 to consumption module 600 can replace or complement existing information sources such as recipe books, food databases like www.epicurious.com, and Epicurious apps. Through the use of specific information regarding a dynamically-labeled nutritional substance from information module 100, consumers can use consumption module 600 to select nutritional substances according to their residual nutritional, organoleptic, and/or aesthetic values. This will further allow consumers to make informed decisions regarding nutritional substance additives, preservatives, genetic modifications, origins, traceability, adulteration, and other nutritional substance attributes that may also be tracked through the information module 100. This information can be provided by consumption module 600 through personal computers, laptop computers, tablet computers, and/or smartphones. Software running on these devices can include dedicated computer programs, modules within general programs, and/or smartphone apps. An example of such a smartphone app regarding nutritional substances is the iOS ShopNoGMO from the Institute for Responsible Technology. This iPhone app allows consumers access to information regarding non-genetically modified organisms they may select. Additionally, consumption module 600 may provide information for the consumer to operate conditioning module 500 in such a manner as to optimize residual nutritional, organoleptic, and/or aesthetic values of a dynamically-labeled nutritional substance and/or component nutritional substances thereof according to the consumer's needs or preference, and/or minimize degradation of, preserve, or improve residual nutritional, organoleptic, and/or aesthetic value of a dynamically-labeled nutritional substance and/or component nutritional substances thereof.

Through the use of nutritional substance information available from information module 100 nutritional substance supply system 10 can track nutritional, organoleptic, and/or aesthetic value of dynamically-labeled nutritional substances. Using this information, dynamically-labeled nutritional substances travelling through nutritional substance supply system 10 can be dynamically valued and priced according to residual nutritional, organoleptic, and/or aesthetic values. For example, nutritional substances with longer dynamic expiration dates (longer shelf life) may be more highly valued than nutritional substances with shorter expiration dates. Additionally, nutritional substances with higher nutritional, organoleptic, and/or aesthetic values may be more highly valued, not just by the consumer, but also by each entity within nutritional substance supply system 10. This is because each entity will want to start with a nutritional substance with higher nutritional, organoleptic, and/or aesthetic value before it performs its function and passes the nutritional substance along to the next entity. Therefore, both the starting nutritional, organoleptic, and/or aesthetic value and the $\Delta N$ associated with those values are important factors in determining or estimating an actual, or residual, nutritional, organoleptic, and/or aesthetic value of a nutritional substance, and accordingly are important factors in establishing dynamically valued and priced nutritional substances.

During the period of implementation of the present inventions, there will be nutritional substances being marketed including those benefiting from dynamic labeling and the tracking of dynamic nutritional information such as $\Delta N$, also referred to herein as information-enabled nutritional substances, and nutritional substances which do not benefit from dynamic labeling or the tracking of dynamic nutritional information such as $\Delta N$, which are not information enabled and are referred to herein as dumb nutritional substances. Information-enabled nutritional substances would be available in virtual internet marketplaces, as well as traditional marketplaces. Because of information provided by information-enabled nutritional substances, entities within the nutritional substance supply system 10, including consumers, would be able to review and select information-enabled nutritional substances for purchase. It should be expected that, initially, the information-enabled nutritional substances would enjoy a higher market value and price than dumb nutritional substances. However, as information-enabled nutritional substances become more the norm, the cost savings from less waste due to degradation of information-enabled nutritional substances could lead to their price actually becoming less than dumb nutritional substances. Ultimately, an information system will evolve wherein information module 100 has the ability for creating traffic and signing on the address of users to not only facilitate the rapid adoption and utilization of better nutritional substance information, but also be a key source of business and revenue growth.

In the example of the ready-to-eat frozen dinner, the transformer of the ready-to-eat frozen dinner would prefer to use corn of a high nutritional, organoleptic, and/or aesthetic value in the production of its product, the ready-to-eat frozen dinner, so as to produce a premium product of high residual nutritional, organoleptic, and/or aesthetic value. Depending upon the post transformation levels of the nutritional, organoleptic, and/or aesthetic values, the ready-to-eat frozen dinner producer may be able to charge a premium price and/or differentiate its product from that of other transformers. When selecting the corn to be used in the ready-to-eat frozen dinner, the transformer will seek corn of high nutritional, organoleptic, and/or aesthetic value from preservation module 300 that meets its requirements for nutritional, organoleptic, and/or aesthetic value. The packager/shipper of preservation module 300 would also be able to charge a premium for corn which has high nutritional, organoleptic, and/or aesthetic values. Accordingly, the packager/shipper of preservation module 300 will select corn that is received from the grower of creation module 200 with high nutritional, organoleptic, and/or aesthetic value and transfer the corn to the transformer by logistic transport that best maintains those values. In turn, the grower of creation module 200 will also be able to charge a premium for corn of high nutritional, organoleptic, and/or aesthetic values, and will endeavor to grow corn with high initial nutritional, organoleptic, and aesthetic values and transfer the corn to the packager/shipper by logistic transport that best maintains those values.

The change to nutritional, organoleptic, and/or aesthetic value for an information-enabled nutritional substance, or $\Delta N$, tracked through nutritional substance supply system 10 through nutritional substance information from information module 100 can be preferably determined from measured information. However, some or all such nutritional substance $\Delta N$ information may be derived through measurements of environmental conditions of the nutritional substance as it travels through nutritional substance supply system 10. Additionally, some or all of the information-enabled nutritional substance $\Delta N$ information can be derived from $\Delta N$ data of other information-enabled nutritional substances which have traveled through nutritional substance supply system 10. Information-enabled nutritional substance $\Delta N$ information can also be derived from laboratory experiments performed on other nutritional substances, which may approximate conditions and/or processes to which the actual information-enabled nutritional substance has been exposed. Further, consumer feedback and updates regarding observed or measured changes in the nutritional, organoleptic, and/or aesthetic value of information-enabled nutritional substances can play a role in updating $\Delta N$ information. Also, a creator, preserver (including logistic transporters), transformer, or conditioner may revise $\Delta N$ information, or information regarding other attributes of information-enabled nutritional substances they have previously created or processed, based upon newly acquired information affecting the $\Delta N$ or the other attributes.

For example, laboratory experiments can be performed on bananas to determine effect on or change in nutritional, organoleptic, and/or aesthetic value, or $\Delta N$, for a variety of environmental conditions bananas may be exposed to during packaging and shipment in preservation module 300. Using this experimental data, tables and/or algorithms could be developed which would predict the level of change of nutritional, organoleptic, and/or aesthetic values, or $\Delta N$, for a particular information-enabled banana based upon information collected regarding the environmental conditions to which the information-enabled banana was exposed during its time in preservation module 300. While the ultimate goal for nutritional substance supply system 10 would be the actual measurement of nutritional, organoleptic, and/or aesthetic values to determine $\Delta N$, use of derived nutritional, organoleptic, and/or aesthetic values from experimental data to determine $\Delta N$ would allow improved logistics planning because it provides the ability to prospectively estimate changes to nutritional, organoleptic, and/or aesthetic values, or $\Delta N$, and because it allows more accurate tracking of changes to nutritional, organoleptic, and/or aesthetic values, or $\Delta N$, while technology and systems are put in place to allow actual measurement.

Figure 3:
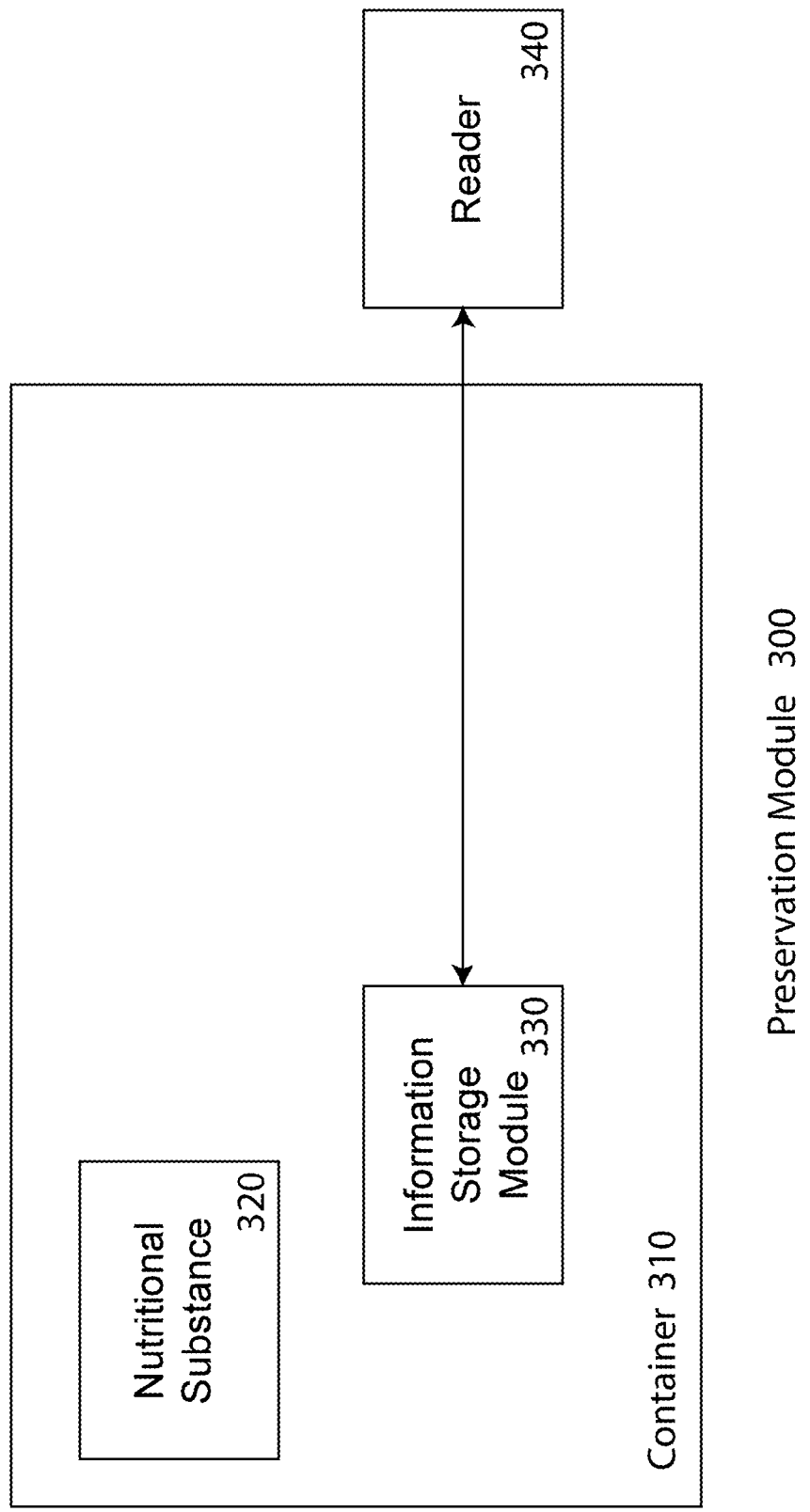
FIG. 3 shows a schematic functional block diagram of the preservation module 300 according to the present invention.

FIG. 3 shows an embodiment of the preservation module of the present invention. Preservation system 300 includes a container 310 which contains nutritional substance 320. Also included in container 310 is information storage module 330 which can be connected to an external reader 340. In this embodiment, information storage module 330 contains information regarding the nutritional substance 320. This information can include creation information from the creation of the nutritional substance 320. Additionally, information in the information storage module 330 might include unique nutritional substance identification information, including but not limited to a dynamic information identifier, information regarding prior transformation or preservation of the nutritional substance 320, information related to $\Delta N$, and other historic information. A shipper, or user, of container 310 can operatively connect to information storage module 330 using reader 340 to retrieve information stored therein. It is understood that reader 340 can additionally transmit information retrieved from information storage module 330 to information module 100, wherein such information is referenced to the unique nutritional substance identification information.

In another embodiment, reader 340 can also write to information storage module 330. In this embodiment, information regarding the container 310 and/or nutritional substance 320 can be modified or added to information storage module 330 by the user or shipper, such as a storage facility or logistic transporter. In a further embodiment, such information is sensed or detected by the reader 340.

Figure 4:
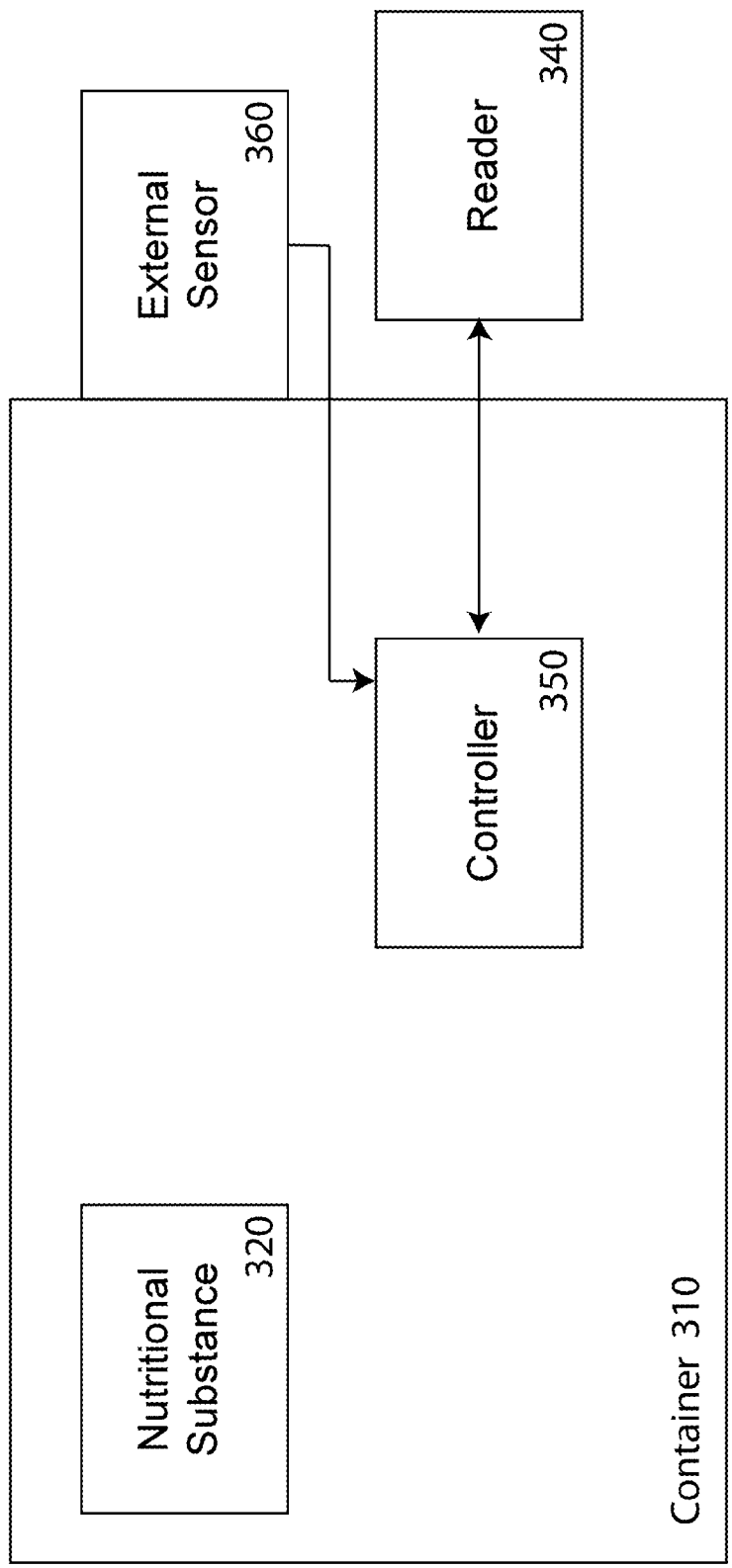
FIG. 4 shows a schematic functional block diagram of the preservation module 300 according to an alternate embodiment of the present invention.

FIG. 4 shows another embodiment of preservation system 300 wherein container 310 contains nutritional substance 320 as well as controller 350. Controller 350 is connected to external sensor 360 located either inside, on the surface of, or external to container 310 such that external sensor 360 can obtain information regarding the environment external to container 310. Controller 350 and exterior sensor 360 can take the form of electronic components such as a microcontroller and an electronic sensor. However, the controller-sensor combination may also be chemical or organic materials which perform the same function, such as a liquid crystal sensor/display.

When the shipper or user (such as a storage facility or logistic transporter) of container 310 desires information from external sensor 360 the shipper or user can use reader 340 to query the controller 350 as to the state of external sensor 360. A unique nutritional substance identifier, such as a dynamic information identifier referenced to the nutritional substance 320, may be associated with at least one of the external sensor 360, the controller 350, or the container 310, such that when reader 340 queries controller 350 as to the state of external sensor 360, the information received is associated with the unique nutritional substance identifier. The external sensor, controller, and reader may take any known forms, including but not limited to, an electronic component embodiment where reader 340 could be a user interface device such as a computer which can be electronically connected to controller 350, or a liquid crystal sensor/display embodiment, where the reader could be a human looking at the display.

In one embodiment, reader 340 can be directly connected to external sensor 360 to obtain the information from external sensor 360 without need of a controller 350. In another embodiment, external sensor 360 provides information to controller 350 which is presented as a visual display to the shipper or user. Alternatively, external sensor 360 could provide information directly to the user or shipper by visual means such as a temperature sensitive liquid crystal thermometer. It is understood that reader 340 may additionally transmit information retrieved from controller 350 or external sensor 360, along with the associated unique nutritional substance identifier, to information module 100, wherein such information is referenced to the unique nutritional substance identifier.

In an additional embodiment, controller 350 can modify the operation of container 310 so as modify the preservation capabilities of container 310, so as to favorably influence a $\Delta N$ of the nutritional substance. For example, if the exterior environment of container 310 would adversely affect the nutritional substance 320, controller 350 could adjust the internal environment of container 310 to better preserve the nutritional substance. If nutritional substance needs to be kept within a desired temperature range to preserve its nutritional, organoleptic, and/or aesthetic properties, and the external sensor 360 provides exterior temperature information to controller 350 that it is currently outside the desired range or may potentially fall outside the desired range, controller 350 could modify container 310 so as to maintain nutritional substance 320 within the desired temperature range.

Figure 5:
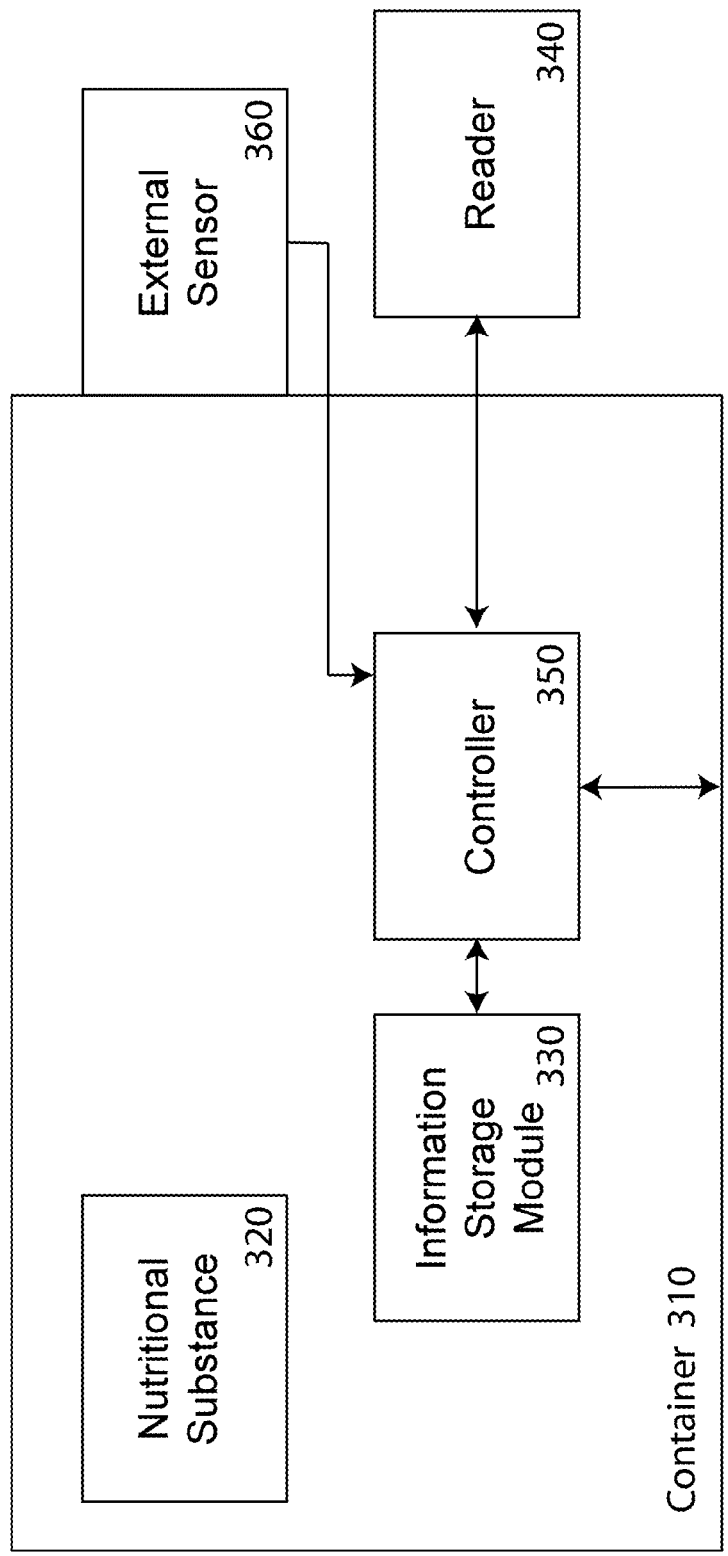
FIG. 5 shows a schematic functional block diagram of the preservation module 300 according to an alternate embodiment of the present invention.

In FIG. 5, preservation system 300 includes container 310 which contains nutritional substance 320, controller 350, and information storage module 330. External sensor 360 is positioned such that it can provide information on the exterior environment to container 310. Information from the external sensor 360 and information storage module 330 can be retrieved by connecting reader 340 to container 310, so as to obtain the information via the controller 350. It is understood that connecting reader 340 to container 310 includes any known contact or non-contact formats that facilitate data transfer.

In this embodiment, information regarding the external environment sensed by external sensor 360 and provided to controller 350 can be stored in information storage module 330. This storage of external environment can be used to record a history the external environment container 310 has been subjected to. This would allow the shipper or user of container 310 to understand the external environment the container has been subjected to during the time it has preserved the nutritional substance. Such information can be used to determine any number of $\Delta N$ values for the nutritional substance and if the nutritional substance has been degraded such that it is no longer in an optimal state or if it is no longer safe for consumption. Additionally, the user of the nutritional substance could modify its transformation, conditioning, or consumption according to any changes, or $\Delta N$s, that may have occurred because of the external conditions of the container.

Additionally, in this embodiment, information storage module 330 could contain other information regarding the nutritional substance 320, including, but not limited to, creation information, and prior transformation or preservation information. Additionally, information in the information storage module 330 might include unique nutritional substance identification information, including but not limited to a dynamic information identifier. In this way, the information obtained by reader 340 is associated with the unique nutritional substance identifier. It is understood that reader 340 may additionally transmit information retrieved from information storage module 330, including the associated unique nutritional substance identifier, to information module 100, wherein such information is referenced to the unique nutritional substance identifier.

In an additional embodiment, controller 350 can modify the operation of container 310 so as modify the preservation capabilities of container 310, so as to favorably influence a $\Delta N$ of the nutritional substance. For example, if the exterior environment of container 310 would adversely affect the nutritional substance 320, controller 350 could adjust the internal environment of container 310 to better preserve the nutritional substance. Controller 350 can analyze the historic information from external sensor 360, stored in information storage module 330 to determine any long-term exterior conditions environmental. If nutritional substance needs to be kept within a desired temperature range to preserve its nutritional, organoleptic and/or aesthetic properties, and the external sensor 360 provides exterior temperature information to controller 350 indicating that it is outside the desired range or at risk of going outside the desired range, controller 350 could modify container 310 so as to maintain nutritional substance 320 within the desired temperature range.

In another embodiment, reader 340 can also write to information storage module 330 via controller 350. In this embodiment, information regarding the container 310 and/or nutritional substance 320 can be modified or added to information storage module 330 by the user or shipper, such as a storage facility or logistic transporter. In a further embodiment, such information is sensed or detected by the reader 340.

Figure 6:
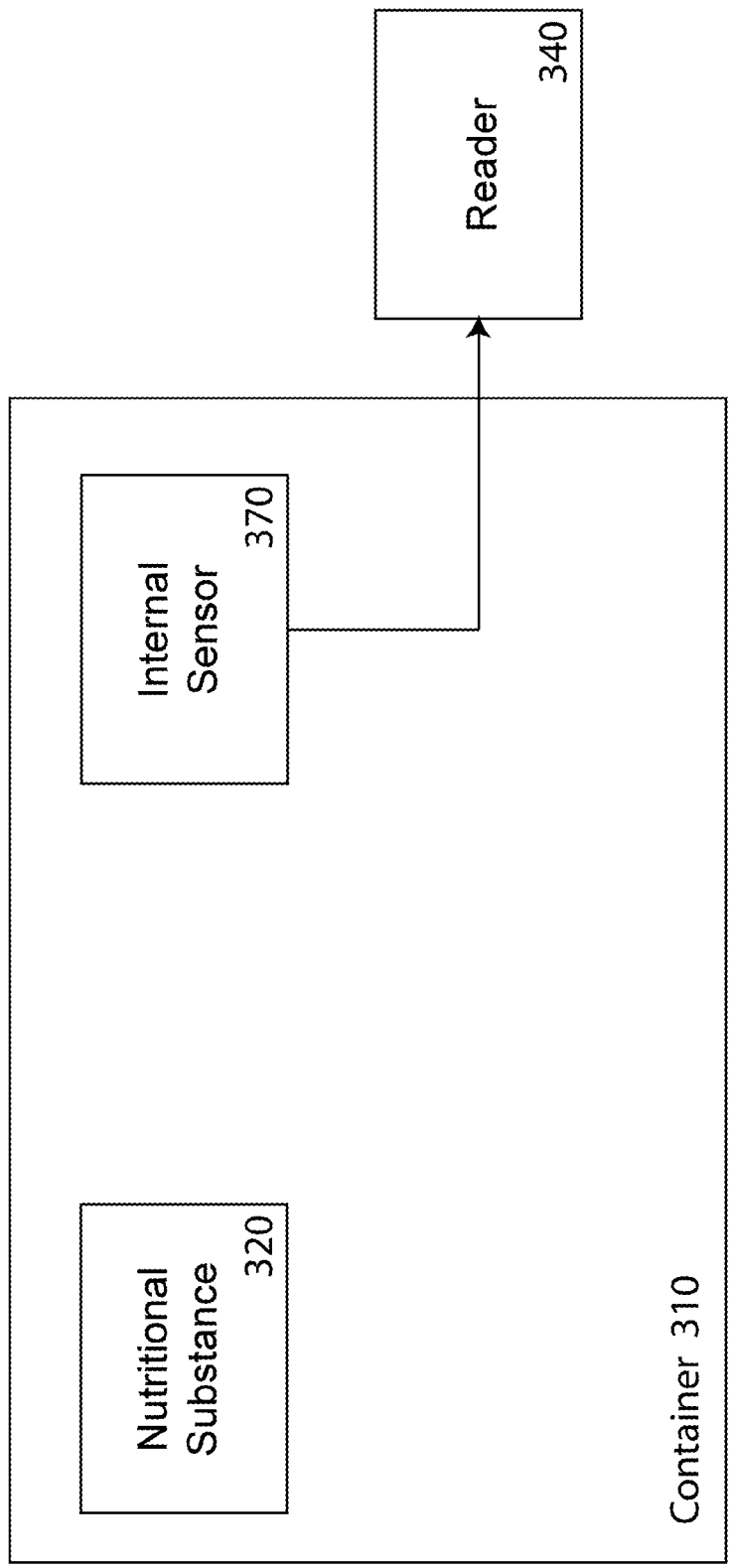
FIG. 6 shows a schematic functional block diagram of the preservation module 300 according to an alternate embodiment of the present invention.

FIG. 6 shows an embodiment of preservation system 300 wherein container 310 contains nutritional substance 320 as well as internal sensor 370 located either inside, or on an inner surface of, container 310, such that internal sensor 370 can obtain information regarding the environment internal to container 310. Reader 340 can obtain information regarding the interior conditions of container 310 from internal sensor 370. Internal sensor 370 and reader 340 can take many known forms, including but not limited to electronic components such as an electronic sensor and electronic display, or chemical or organic materials which perform the same function, such as a liquid crystal sensor/display.

When the shipper or user of container 310 desires information from internal sensor 370, it can be retrieved by connecting reader 340 to container 310, so as to obtain the information from the internal sensor 370 as to the state of internal sensor 370. It is understood that connecting reader 340 to container 310 includes any known contact or non-contact formats that facilitate data transfer. A unique nutritional substance identifier, such as a dynamic information identifier referenced to the nutritional substance 320, may be associated with at least one of the internal sensor 370 or the container 310, such that when reader 340 queries as to the state of internal sensor 370, the information obtained is associated with the unique nutritional substance identifier. It is understood that reader 340 may additionally transmit information retrieved from internal sensor 370, including the associated unique nutritional substance identifier, to information module 100, wherein such information is referenced to the unique nutritional substance identifier.

Figure 7:
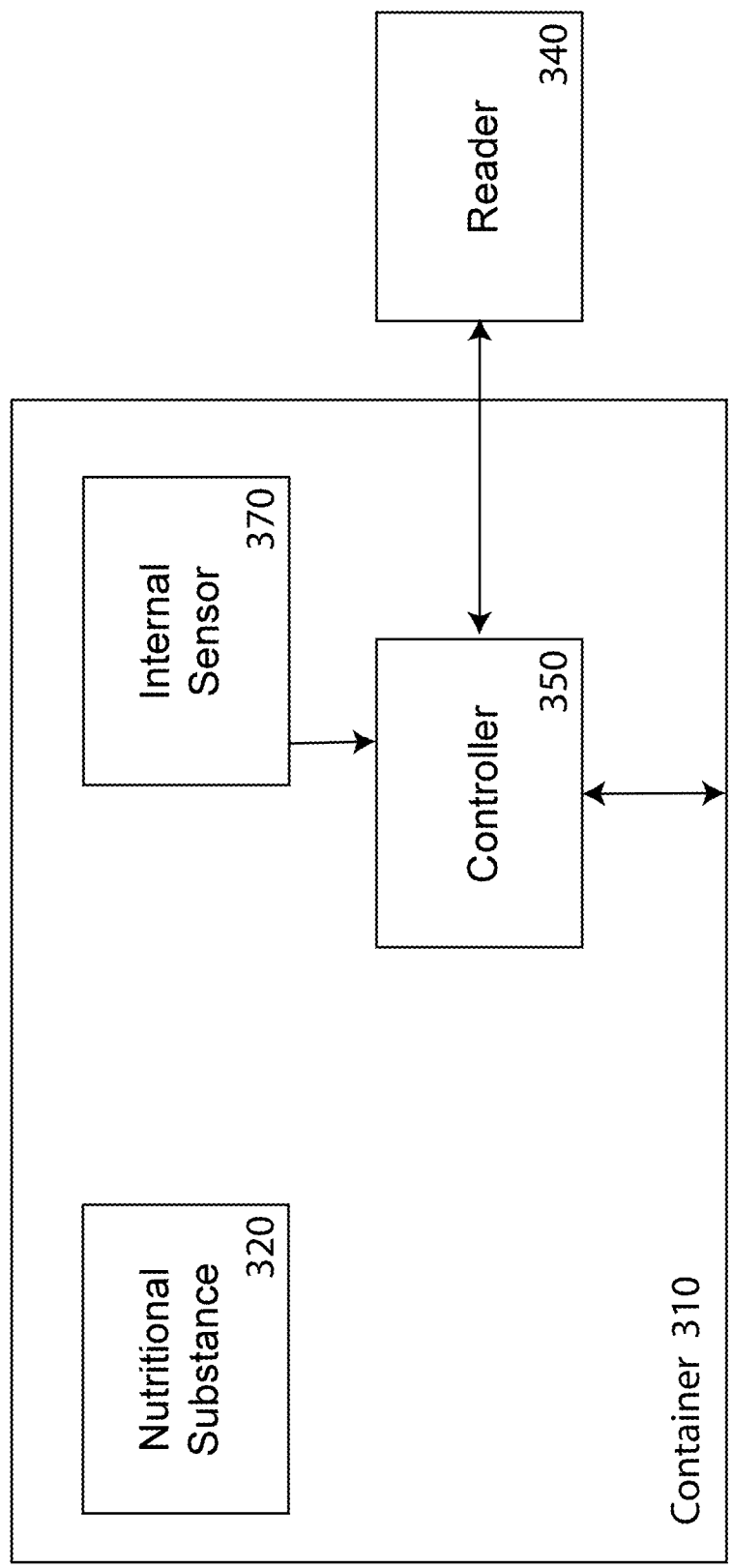
FIG. 7 shows a schematic functional block diagram of the preservation module 300 according to an alternate embodiment of the present invention.

FIG. 7 shows embodiment of preservation system 300 wherein container 310 contains nutritional substance 320 as well as controller 350. Controller 350 is connected to internal sensor 370 located either inside, or on an inner surface of, container 310, such that internal sensor 370 can obtain information regarding the environment internal to container 310. Controller 350 and internal sensor 370 can take any known form, which include but are not limited to electronic components such as a micro-controller and an electronic sensor, or chemical or organic materials which perform the same function, such as a liquid crystal sensor/display.

When the shipper or user of container 310 desires information from internal sensor 370, it can be retrieved by connecting reader 340 to container 310, so as to obtain the information via controller 350 as to the state of internal sensor 370. It is understood that connecting reader 340 to container 310 includes any known contact or non-contact formats that facilitate data transfer. A unique nutritional substance identifier, such as a dynamic information identifier referenced to the nutritional substance 320, may be associated with at least one of the internal sensor 370, the controller 350, or the container 310, such that when reader 340 queries as to the state of internal sensor 370, the information obtained is associated with the unique nutritional substance identifier. It is understood that reader 340 may additionally transmit information obtained from internal sensor 370, including the associated unique nutritional substance identifier, to information module 100, wherein such information is referenced to the unique nutritional substance identifier. In an example of an electronic component embodiment, reader 340 could be a user interface device such as a computer which can be electronically connected to internal sensor 370 via controller 350.

In an additional embodiment, controller 350 can modify the operation of container 310 so as modify the preservation capabilities of container 310, so as to favorably influence a ΔN of the nutritional substance. For example, if the interior environment of container 310 would adversely affect the nutritional substance 320, controller 350 could adjust the internal environment of container 310 to better preserve the nutritional substance. If nutritional substance needs to be kept within a desired temperature range to preserve its nutritional, organoleptic, and/or aesthetic properties, and the internal sensor 370 provides internal temperature information to controller 350 indicating that it is outside the desired range or may potentially go outside the desired range, controller 350 could modify container 310 so as to maintain nutritional substance 320 within the desired temperature range.

Figure 8:
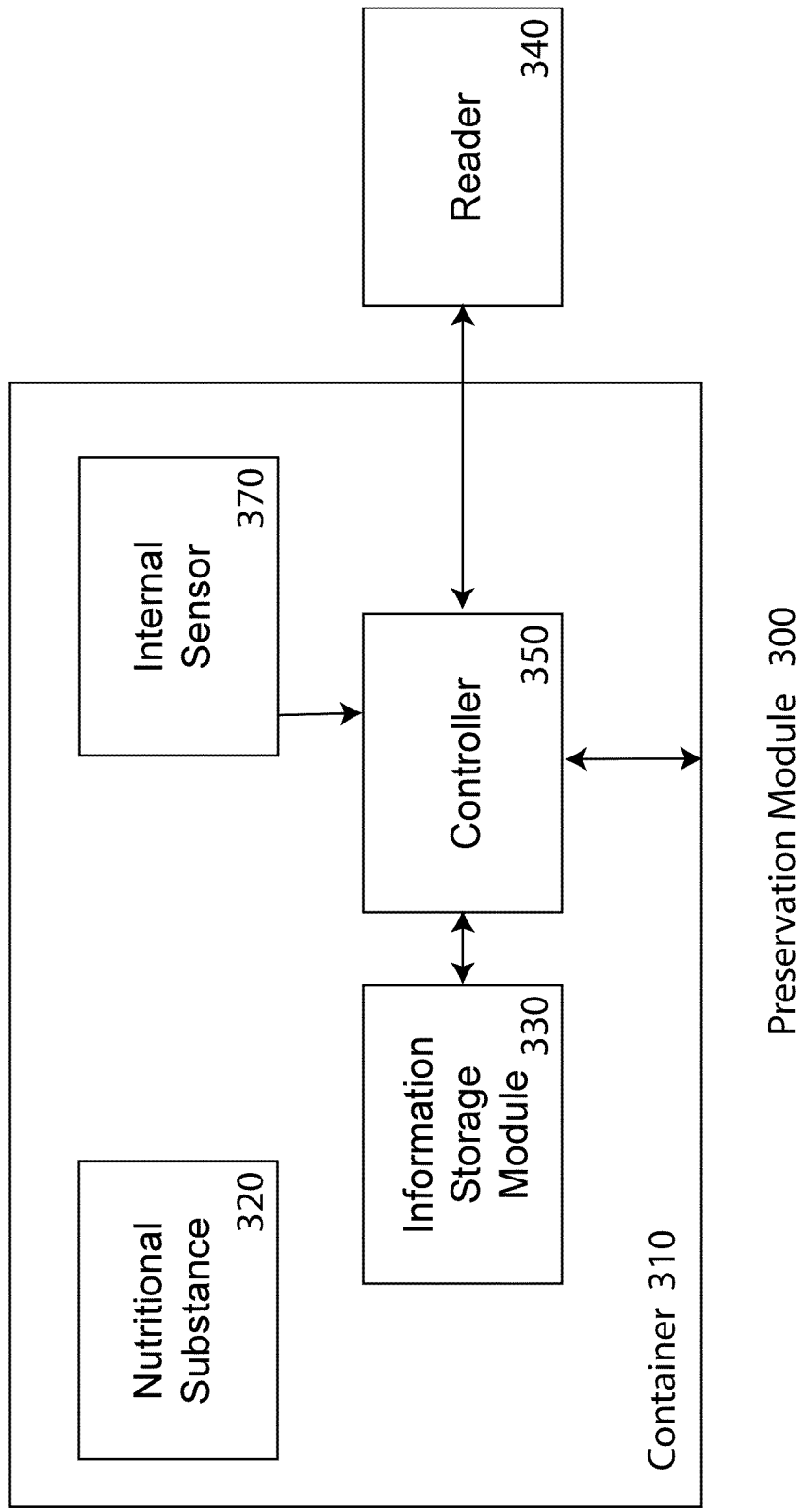
FIG. 8 shows a schematic functional block diagram of the preservation module 300 according to an alternate embodiment of the present invention.

In FIG. 8, preservation system 300 includes container 310 which contains nutritional substance 320, controller 350, and information storage module 330. Internal sensor 370 is positioned such that it can provide information on the internal environment to container 310. Information from the internal sensor 370 and information storage module 330 can be retrieved by connecting reader 340 to container 310, so as to obtain the information via the controller 350. It is understood that connecting reader 340 to container 310 includes any known contact or non-contact formats that facilitate data transfer.

In this embodiment, information regarding the internal environment sensed by internal sensor 370 and provided to controller 350 can be stored in information storage module 330. This storage of internal environment can be used to record a history the internal environment container 310 has been subjected to. This would allow the shipper or user of container 310 to understand the internal environment the container has been subjected to during the time it has preserved the nutritional substance. Such information can be used to determine any number of ΔN values of the nutritional substance, such as if the nutritional substance has been degraded such that it is no longer in an optimal nutritional, organoleptic, or aesthetic state, or if it is no longer safe for consumption. Additionally, the user of the nutritional substance could modify its transformation, conditioning, or consumption according to any changes, or ΔNs, that may have occurred because of the internal conditions of the container.

Additionally, in this embodiment, information storage module 330 could contain other information regarding the nutritional substance 320, including, but not limited to, creation information, and prior transformation or preservation information. Additionally, information in the information storage module 330 might include unique nutritional substance identification information, including but not limited to a dynamic information identifier. In this way, the information obtained by reader 340 is associated with the unique nutritional substance identifier. It is understood that reader 340 may additionally transmit information retrieved from information storage module 330, including the associated unique nutritional substance identifier, to information module 100, wherein such information is referenced to the unique nutritional substance identifier.

In an additional embodiment, controller 350 can modify the operation of container 310 so as modify the preservation capabilities of container 310. For example, if the internal environment of container 310 would adversely affect the nutritional substance 320, controller 350 could adjust the internal environment of container 310, so as to favorably influence a ΔN of the nutritional substance. Controller 350 can analyze the historic information from internal sensor 370, stored in information storage module 330, to determine any long-term internal environmental conditions. If the nutritional substance needs to be kept within a desired temperature range to preserve its organoleptic and/or nutritional properties, and the internal sensor 370 provides internal temperature information to controller 350 indicating that it is currently or potentially outside the desired range, controller 350 could modify container 310 so as to maintain nutritional substance 320 within the desired temperature range.

In another embodiment, reader 340 can also write to information storage module 330 via controller 350. In this embodiment, information regarding the container 310 and/or nutritional substance 320 can be modified or added to information storage module 330 by the user or shipper, such as a storage facility or logistic transporter. In a further embodiment, such information is sensed or detected by the reader 340.

Figure 9:
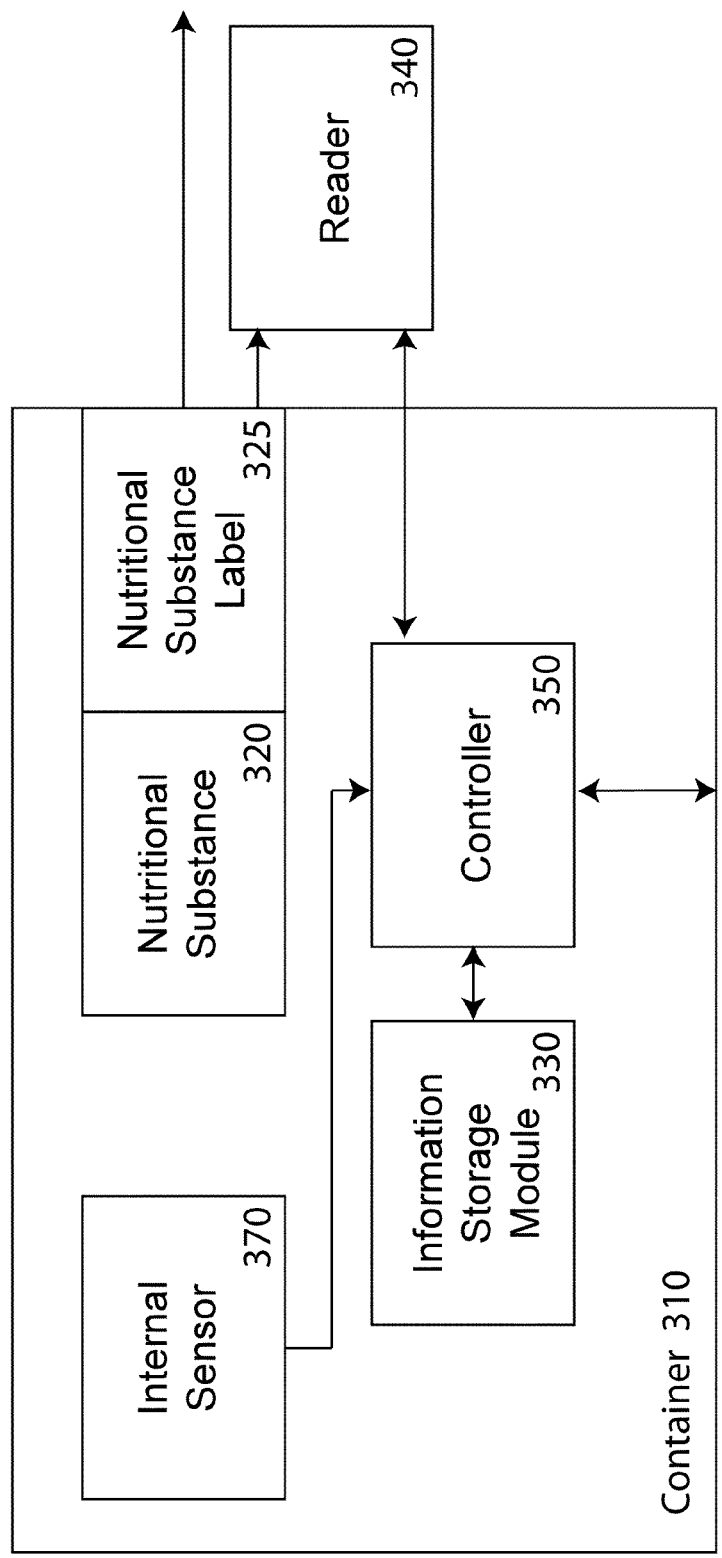
FIG. 9 shows a schematic functional block diagram of the preservation module 300 according to an alternate embodiment of the present invention.

FIG. 9 shows an alternate embodiment of the present invention. Preservation system 300 includes container 310 which contains nutritional substance 320, nutritional substance label 325, controller 350, and information storage module 330. Internal sensor 370 is positioned such that it can provide information on the internal environment to container 310. Information from the internal sensor 370 and information storage module 330 can be retrieved by connecting reader 340 to container 310, so as to obtain the information via the controller 350. It is understood that connecting reader 340 to container 310 includes any known contact or non-contact formats that facilitate data transfer. Nutritional substance label 325 is attached to nutritional substance 320 so as to sense, measure, and/or indicate a current state of nutritional substance 320. Nutritional substance label 325 can be read by reader 340. Nutritional substance label 325 could be any known type of biosensor, including but not limited to a material/chemical tag that, through a physical reaction with the surface of nutritional substance 320, provides information regarding the nutritional, organoleptic, and/or aesthetic state of the nutritional substance, or information regarding changes in the nutritional, organoleptic, and aesthetic values of the nutritional substance, including where nutritional substance 320 is in its life cycle. As an example, this label/tag could change color as a fruit, cheese or wine matures across time. It could also indicate if it detects traces of pesticides, hormones, allergens, harmful or dangerous bacteria, or any other substances.

In this embodiment, information regarding the internal environment sensed by internal sensor 370 and provided to controller 350 can be stored in information storage module 330. This storage of internal environment can be used to record a history the internal environment container 310 has been subjected to. This would allow the shipper or user of container 310 to understand the internal environment the container has been subjected to during the time it has preserved the nutritional substance. Such information can be used to determine any number of ΔN values for the nutritional substance, including if the nutritional substance has been degraded such that it is no longer in an optimal state, or if it is no longer safe for consumption. Additionally, the user of the nutritional substance could modify its transformation, conditioning, or consumption according to any changes, or ΔNs, that may have occurred because of the internal conditions of the container.

Additionally, in this embodiment, information storage module 330 could contain other information regarding the nutritional substance 320, including, but not limited to, creation information, and prior transformation or preservation information. Additionally, information in the information storage module 330 might include unique nutritional substance identification information, including but not limited to a dynamic information identifier. In this way, the information obtained by reader 340 is associated with the unique nutritional substance identifier. It is understood that reader 340 may additionally transmit information retrieved from information storage module 330, including the associated unique nutritional substance identifier, as well as information retrieved from nutritional substance label 325, to information module 100, wherein such information is referenced to the unique nutritional substance identifier.

In an additional embodiment, controller 350 can modify the operation of container 310 so as modify the preservation capabilities of container 310, so as to favorably influence a ΔN of the nutritional substance. For example, if the internal environment of container 310 would adversely affect the nutritional substance 320, container 310 could adjust the internal environment of container 310 to better preserve the nutritional substance. Controller 350 can analyze the historic information from internal sensor 370, stored in information storage module 330 to determine any long-term internal environmental conditions. If nutritional substance needs to be kept within a desired temperature range to preserve its nutritional, organoleptic and/or aesthetic properties, and the internal sensor 370 provides internal temperature information to controller 350 indicating that it is currently or potentially outside the desired range, controller 350 could modify container 310 so as to maintain nutritional substance 320 within the desired temperature range.

In another embodiment, reader 340 can also write to information storage module 330 via controller 350. In this embodiment, information regarding the container 310 and/or nutritional substance 320 can be modified or added to information storage module 330 by the user or shipper, such as a storage facility or logistic transporter. In a further embodiment, such information is sensed or detected by the reader 340, and may include information obtained from nutritional substance label 325 by reader 340. It is understood that controller 350 may modify the container 310 in response to information that reader 340 writes to information storage module 330, including, but not limited to, information read from nutritional substance label 325.

Figure 10:
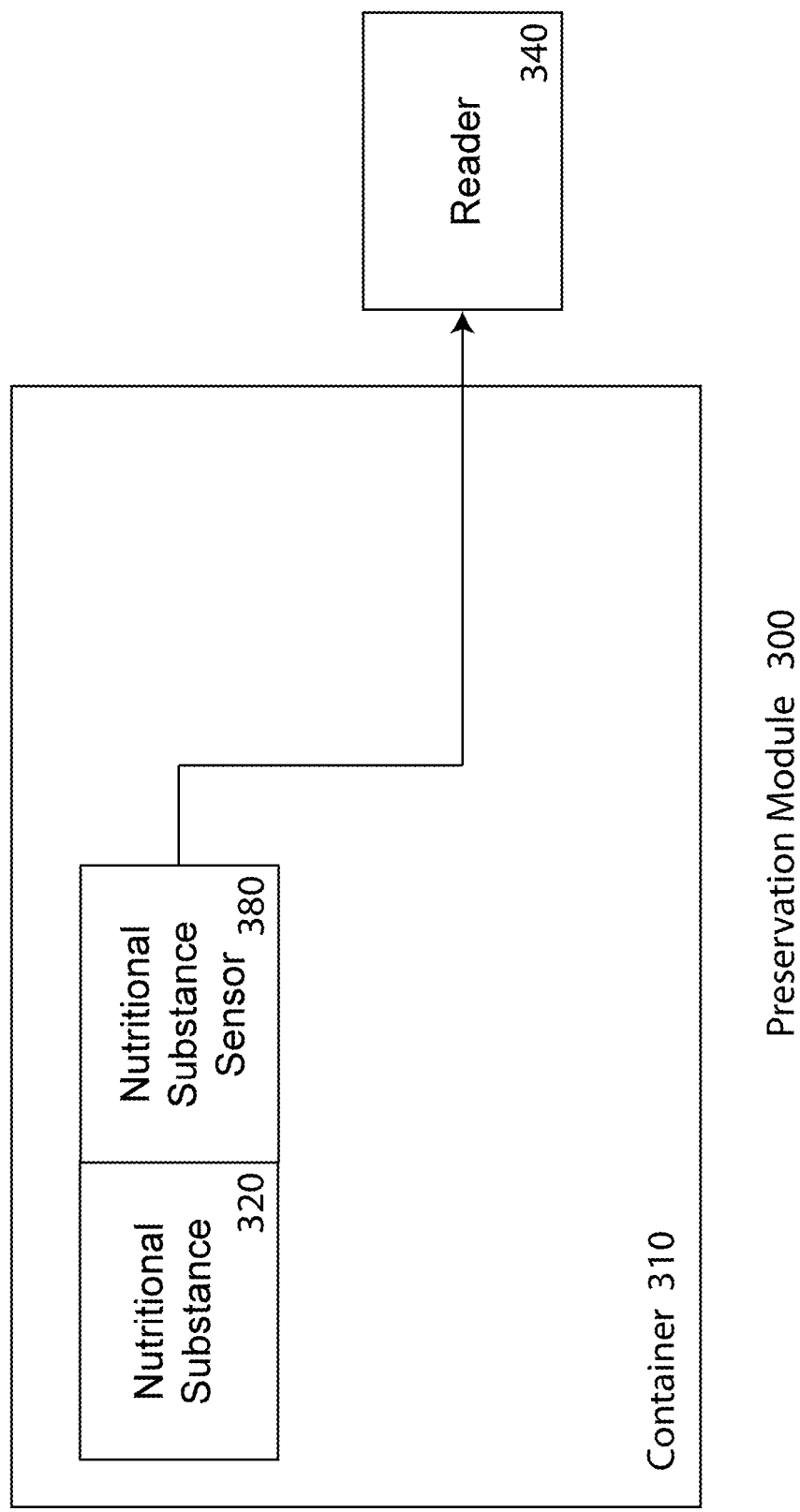
FIG. 10 shows a schematic functional block diagram of the preservation module 300 according to an alternate embodiment of the present invention.

FIG. 10 shows embodiment of preservation system 300 wherein container 310 contains nutritional substance 320 as well as nutritional substance sensor 380 in contact with nutritional substance 320, such that nutritional substance sensor 380 can obtain information regarding the nutritional substance 320 in container 310. Nutritional substance sensor 380 and reader 340 can take any known forms, including but not limited to, biosensors and associated handheld scanners, electronic components such as an electronic sensors and electronic display, or chemical or organic materials which perform the same function, such as a liquid crystal sensor/display.

When the shipper or user of container 310 desires information from nutritional substance sensor 380, it can be retrieved by connecting reader 340 to container 310, so as to obtain the information from the nutritional substance sensor 380 as to the state of nutritional substance 320. It is understood that connecting reader 340 to container 310 includes any known contact or non-contact formats that facilitate data transfer. A unique nutritional substance identifier, such as a dynamic information identifier referenced to the nutritional substance 320, may be associated with at least one of the nutritional substance sensor 380 or the container 310, such that when reader 340 queries as to the state of nutritional substance sensor 380, the information obtained is associated with the unique nutritional substance identifier. It is understood that reader 340 may additionally transmit information retrieved from nutritional substance sensor 380, including the associated unique nutritional substance identifier, to information module 100, wherein such information is referenced to the unique nutritional substance identifier.

Figure 11:
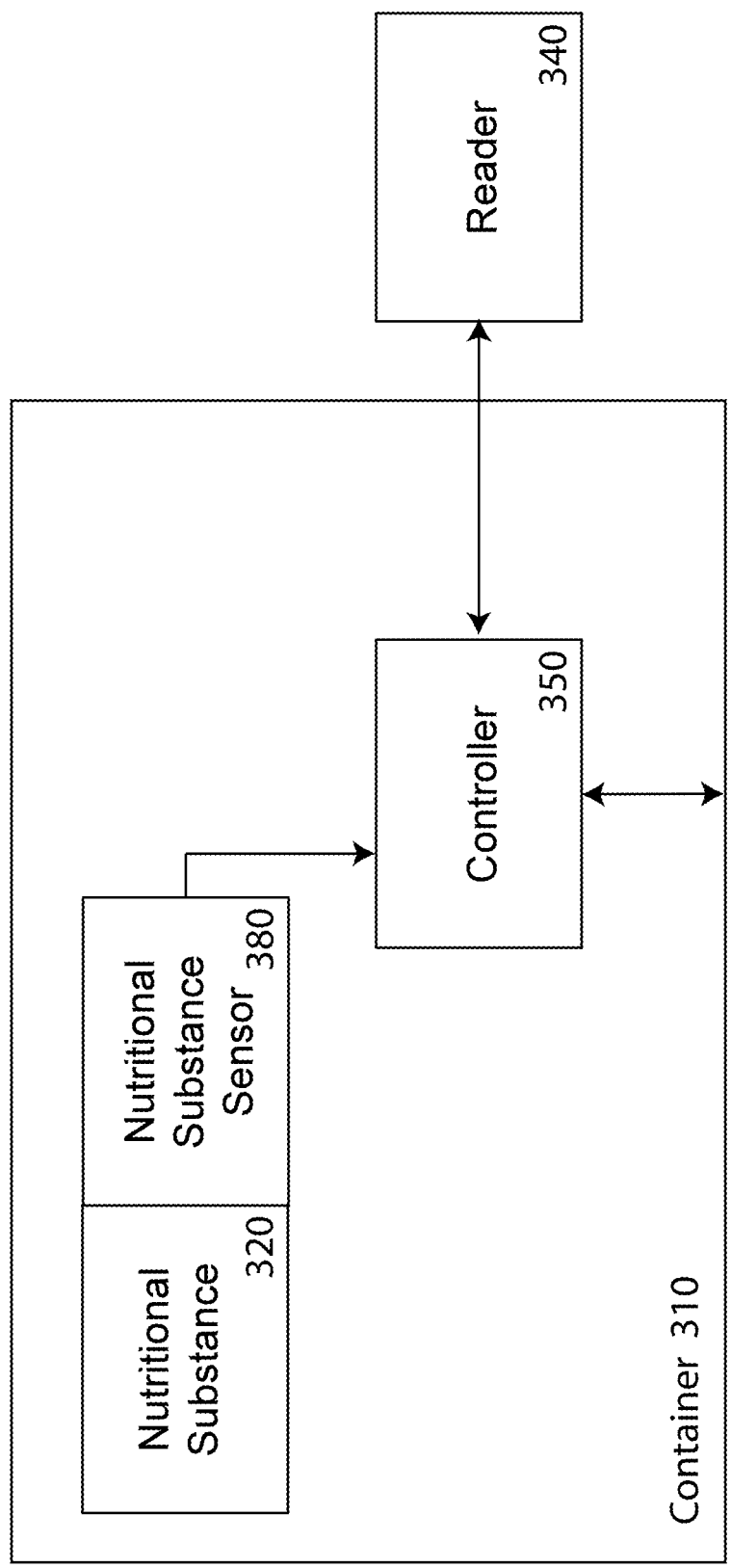
FIG. 11 shows a schematic functional block diagram of the preservation module 300 according to an alternate embodiment of the present invention.

FIG. 11 shows an embodiment of preservation system 300 wherein container 310 contains nutritional substance 320 as well as nutritional substance sensor 380 in contact with nutritional substance 320, such that nutritional substance sensor 380 can obtain information regarding the nutritional substance 320 in container 310, as well as controller 350. Controller 350 is connected to nutritional substance sensor 380. Controller 350 can take any known form, including but not limited to an electronic micro-controller. Nutritional substance sensor 380 and reader 340 can take any known forms, including but not limited to, biosensors and associated handheld scanners, electronic components such as an electronic sensor and display, or chemical or organic materials which perform the same function, such as a liquid crystal sensor/display.

When the shipper or user of container 310 desires information from nutritional substance sensor 380, it can be retrieved by connecting reader 340 to container 310, so as to obtain the information from the nutritional substance sensor 380 via controller 350, as to the state of nutritional substance 320. It is understood that connecting reader 340 to container 310 includes any known contact or non-contact formats that facilitate data transfer. A unique nutritional substance identifier, such as a dynamic information identifier referenced to the nutritional substance 320, may be associated with at least one of the nutritional substance sensor 380, the controller 350, or the container 310, such that when reader 340 queries as to the state of nutritional substance sensor 380, the information obtained is associated with the unique nutritional substance identifier. It is understood that reader 340 may additionally transmit information retrieved from nutritional substance sensor 380, including the associated unique nutritional substance identifier, to information module 100, wherein such information is referenced to the unique nutritional substance identifier.

In an additional embodiment, controller 350 can modify the operation of container 310 so as modify the preservation capabilities of container 310, so as to favorably influence a ΔN of the nutritional substance. For example, if the interior environment of container 310 is adversely affecting the nutritional substance 320, as indicated by information provided by nutritional substance sensor 380, controller 350 could adjust the nutritional substance environment of container 310 to better preserve the nutritional substance. For example, if nutritional substance 320 needs to be kept within a desired temperature range to best preserve its nutritional, organoleptic, and/or aesthetic properties, and the nutritional substance sensor 380 provides nutritional substance information to controller 350 indicating its nutritional, organoleptic, and/or aesthetic properties are degrading too rapidly and likely to be outside the desired range soon, controller 350 could modify container 310 so as to maintain the nutritional, organoleptic, and/or aesthetic properties of nutritional substance 320 within the desired range.

Figure 12:
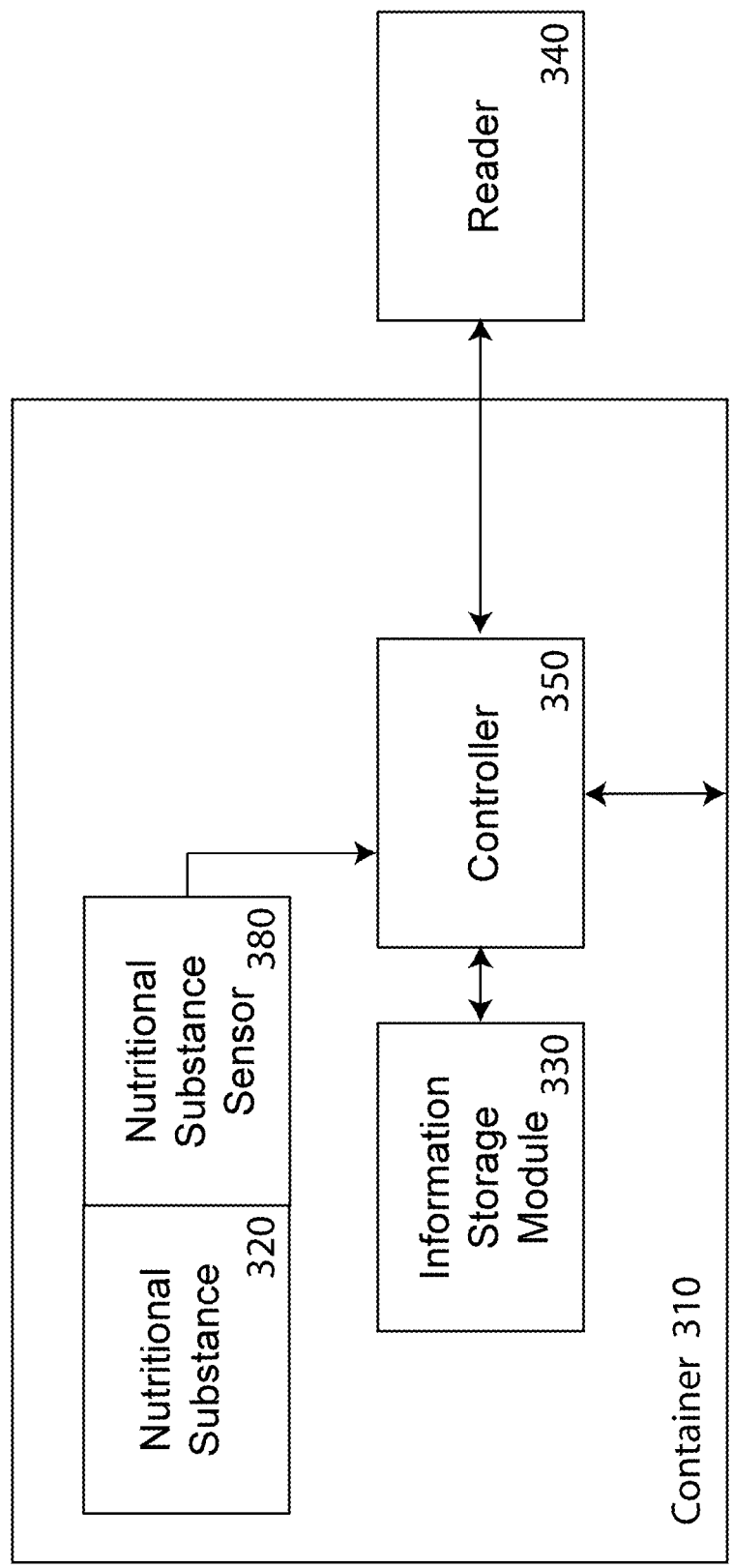
FIG. 12 shows a schematic functional block diagram of the preservation module 300 according to an alternate embodiment of the present invention.

In FIG. 12, preservation system 300 includes container 310 which contains nutritional substance 320, as well as nutritional substance sensor 380 in contact with nutritional substance 320 such that nutritional substance sensor 380 can obtain information regarding the nutritional substance 320, controller 350, and information storage module 330. Information from the nutritional substance sensor 380 and information storage module 330 can be retrieved by connecting reader 340 to container 310, so as to obtain the information via controller 350, as to the state of nutritional substance 320. It is understood that connecting reader 340 to container 310 includes any known contact or non-contact formats that facilitate data transfer.

In this embodiment, information regarding the nutritional substance sensed by nutritional substance sensor 380, and provided to controller 350, can be stored in information storage module 330. This storage of nutritional substance information can be used to record a history the nutritional substance. This would allow the shipper or user of container 310 to understand the nutritional substance during the time it has been preserved. Such information can be used to determine any number of ΔN values of the nutritional substance and if the nutritional substance has been degraded such that it is no longer in an optimal state, or if it is no longer safe for consumption. Additionally, the user of the nutritional substance could modify its transformation, conditioning, or consumption according to any changes, or ΔNs, that may have occurred as evidenced by the information from nutritional substance sensor 380 stored in information storage module 330.

Additionally, in this embodiment, information storage module 330 could contain other information regarding the nutritional substance 320, including, but not limited to, creation information, and prior transformation or preservation information. Additionally, information in the information storage module 330 might include unique nutritional substance identification information, including but not limited to a dynamic information identifier. In this way, the information obtained by reader 340 is associated with the unique nutritional substance identifier. It is understood that reader 340 may additionally transmit information retrieved from information storage module 330, including the associated unique nutritional substance identifier, to information module 100, wherein such information is referenced to the unique nutritional substance identifier.

In an additional embodiment, controller 350 can modify the operation of container 310 so as modify the preservation capabilities of container 310. For example, if the nutritional substance 320 is being adversely affected, as indicated by data provided by nutritional substance sensor 380, controller 350 could adjust the container 310 to better preserve the nutritional substance. Controller 350 can analyze the historic information from nutritional substance sensor 380 stored in information storage module 330 to determine any long-term nutritional substance conditions that need to be changed. For example, if nutritional substance 320 needs to be kept within a desired temperature range to best preserve its nutritional, organoleptic, and/or aesthetic properties, and the nutritional substance sensor 380 provides nutritional substance information to controller 350 indicating its nutritional, organoleptic, and/or aesthetic properties are degrading too rapidly and likely to be outside the desired range soon, controller 350 could modify container 310 so as to maintain the nutritional, organoleptic, and/or aesthetic properties of nutritional substance 320 within the desired range.

In another embodiment, reader 340 can also write to information storage module 330 via controller 350. In this embodiment, information regarding the container 310 and/or nutritional substance 320 can be modified or added to information storage module 330 by the user or shipper, such as a storage facility or logistic transporter. In a further embodiment, such information is sensed or detected by the reader 340.

Figure 13:
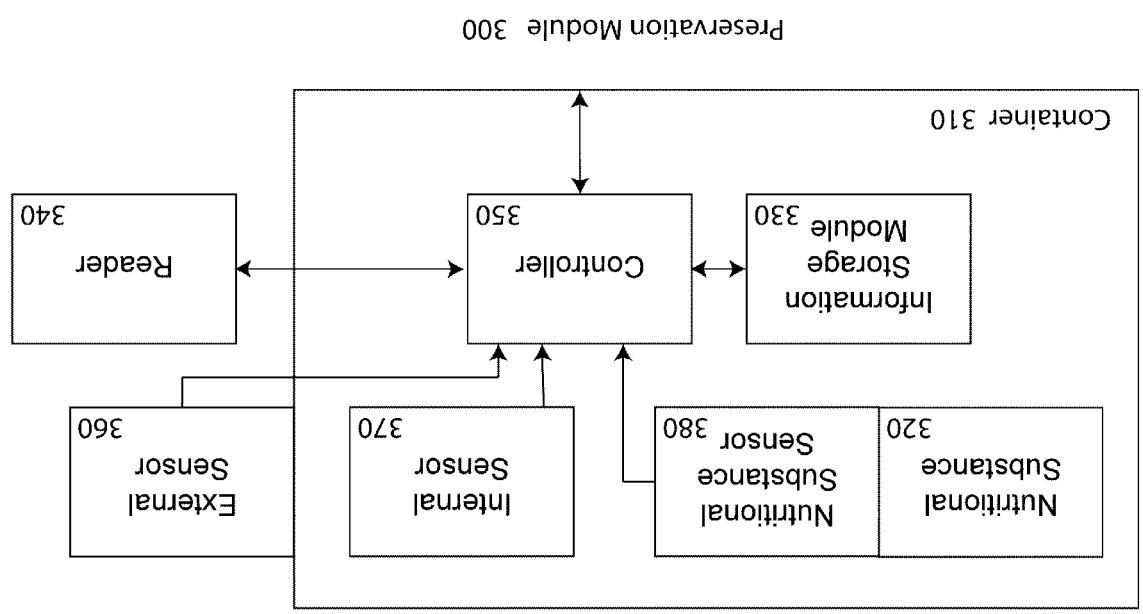
FIG. 13 shows a schematic functional block diagram of the preservation module 300 according to an alternate embodiment of the present invention.

FIG. 13 shows the preferred embodiment of preservation module 300. Within container 310 is nutritional substance 320, as well as nutritional substance sensor 380 in contact with nutritional substance 320 such that nutritional substance sensor 380 can obtain information regarding the nutritional substance 320, internal sensor 370, information storage module 330, and controller 350. External sensor 360 is located outside or on the surface of container 310. In operation, controller 350 receives information from nutritional substance sensor 380, internal sensor 370, and external sensor 360. Additionally, controller 350 can store the information received from the three sensors in information storage module 330. Controller 350 can retrieve such stored information and transmit it to reader 340. Reader 340 can also transmit instructions to controller 350, or write information to information storage module 330.

Controller 350 is operably connected to container 310 so as to use the information obtained from the sensors 360, 370, and 380 and/or information stored in the information storage module 330 to modify the operation of container 310 to affect the state of nutritional substance 320, that is, to favorably influence a ΔN for the nutritional substance. In addition to the stored information from sensors 360, 370, and 380, information storage module 330 could contain other information regarding the nutritional substance 320, including, but not limited to, creation information, and prior transformation or preservation information. Additionally, information in the information storage module 330 might include unique nutritional substance identification information, including but not limited to a dynamic information identifier. In this way, the information obtained by reader 340 is associated with the unique nutritional substance identifier. It is understood that reader 340 may additionally transmit information retrieved from information storage module 330, including the associated unique nutritional substance identifier, to information module 100, wherein such information is referenced to the unique nutritional substance identifier.

As an example, nutritional substance 320 could be bananas being shipped to a distribution warehouse. Bananas are in container 310 which is capable of controlling its internal temperature, humidity, and the level of certain gasses within the container. Creation information as to the bananas is placed in information storage module 330 prior to shipment, as well as a dynamic information identifier. During shipment, external sensor 360 measures the temperature and humidity outside container 310. This information is stored by controller 350 in information storage module 330. Controller 350 also receives information on the internal environment within container 310 from internal sensor 370 and stores this information in information storage module 330. This information includes the internal temperature, humidity, and certain gas levels within container 310. Finally, nutritional substance sensor 380, which is attached to the surface of the bananas, provides information as to the state of the bananas to controller 350. This information could include, but is not limited to, surface temperature, surface humidity, gasses being emitted, color, and surface chemicals. At any time during its shipment and delivery to the distribution warehouse, reader 340 can be used to retrieve both current information and historic information stored within information storage module 330 and may additionally transmit the information retrieved, including the associated unique nutritional substance identifier, to information module 100, wherein such information is referenced to the unique nutritional substance identifier.

During shipment, container 310 modifies its internal conditions according to instructions provided by controller 350. Controller 350 contains instructions as to how to preserve, and possibly ripen, the bananas using information stored in information storage module 330 about the creation of the bananas, as well as historical information received from the three sensors, as well as current information being received from the three sensors, as well as information that may have been written to information storage module 330 from reader 340. In this manner, preservation module 300 can preserve and optimize and minimize degradation of the bananas. In other words, preservation module 300 can operate in a way to variably adapt conditions in the container to favorably influence changes in nutritional, organoleptic, and aesthetic values/attributes, ΔNs, of the bananas, by variably altering the rate of change of the corresponding ΔNs while they are being shipped and stored.

In one embodiment, a means for variably adapting conditions in the container to variably alter the rate of change of a monitored ΔN, includes at least one of a chemical, photochemical, mechanical, hydraulic, pneumatic, dissolution, absorption, swelling, shrinkage, component addition, component binding, component subtraction, component conversion, electrolytic, ionic, osmotic, reverse osmotic, or thermal means to variably control the gaseous environment in the container in response to information regarding the gaseous environment in the container provided by internal sensor 370, external sensor 360, or nutritional substance sensor 380.

It will be understood that subsets of the embodiment described herein can operate to achieve the goals stated herein. In one embodiment, nutritional substance sensor 380, internal sensor 370, external sensor 360, information storage module 330, controller 350, reader 340, and parts of container 310 are each electrical or electromechanical devices which perform each of the indicated functions. However, it is possible for some or all of these functions to be done using chemical and/or organic compounds. For example, a specifically designed plastic wrap for bananas can sense the exterior conditions of the package, the interior conditions of the package, and adapt the conditions of the package to control gas flow through its surface so as to preserve and ripen the bananas. In one embodiment of such a package, a means for adapting gaseous conditions in the package to variably alter the rate of change of a monitored ΔN, includes at least one of a chemical, photochemical, mechanical, hydraulic, absorption, shrinkage, swelling, pneumatic, dissolution, component addition, component binding, component subtraction, component conversion, electrolytic, ionic, osmotic, reverse osmotic, or thermal means.

Sensors capable of measuring and collecting data related to visual appearance, optical properties, electrical properties, mechanical properties, taste, smell, volatiles, texture, touch, sound, chemical composition, temperature, weight, volume, density, hardness, viscosity, surface tension, and any other detectable attributes of nutritional substances, may be utilized. Nutritional substance attribute sensors may include, but are not limited to, optical sensors, laser sensors, cameras, electric noses, microphones, olfactory sensors, surface topography measurement equipment, three dimensional measuring equipment, chemical assays, hardness measuring equipment, non-invasive imaging equipment including ultrasound, x-ray, millimeter wave, and other known non-invasive imaging techniques, impedance detectors, temperature measuring equipment, weight measurement equipment, and any known sensor capable of providing data regarding a detectable attribute of a nutritional substance.

At this juncture it can be understood that a nutritional, organoleptic or aesthetic value of a nutritional substance can be indicated by its olfactory values or its taste values. Typically, but not necessarily, olfactory values and taste values are detectable by the human sense of smell. However, nutritional substances may emit or produce gaseous components that are not detectable or discernible by the human sense of smell, or components not detectable or discernible by human sense of taste, but, nevertheless, may be indicative of a particular nutritional, organoleptic, and aesthetic state of the nutritional substance. In addition, olfactory values and taste values can be indicative of adulteration of nutritional substances, such as by spoilage, contamination, or substitution of other nutritional substances.

Sensors for detecting gasses and smells may be used to provide ΔN information regarding nutritional substances during their logistic transport. Such sensors include, but are not limited to, nutritional substance sensors discussed in Journal of Food Engineering 100 (2010) 377-387 "Biomimetric-based odor and taste sensing systems to food quality and safety characterization: An overview on basic principles and recent achievements"; sensing described in Chem. Sci., 2012, 3, 2542 "Fluorescent DNAs printed on paper: sensing food spoilage and ripening in the vapor phase"; the use of a Silicon Integrated Spectrometer to sense food for ripeness and other qualities is described in IEEE Photonics Journal, 1 (4), p. 225-235 (2009); a review on nano-biosensors to measure tastes and odors discussed in Bio-Nanotechnology: A revolution in food biomedical and health sciences, first edition, 2013, John Wiley & Sons, Ltd. "Nano-Biosensors for mimicking gustatory and olfactory senses"; ethylene sensors discussed in Anal. Chem., 2011, 83 (16), pp 6300-6307, doi: 10.1021/ac2009756 "Electrochemical sensing of ethylene employing a thin ionic-liquid layer"; commercially available Ethylene Analyser sensor from Absorger Company, for sensing ethylene, O2, and CO2 levels, www.absoger.fr; a single-chip electrochemical sensor for ethylene monitoring demonstrated by Imec and Holst Centre with a detection limit of 200-300 ppb and potentially, May 15, 2012, http://www2.imec.be/be_en/press/imec-news/ethylenesensor.html.

In an example, and not intended to be limiting in any way, the ripening of fruit during logistic transport can be monitored by sensed values provided by such gas and smell sensors inside a logistic transport container, and can further be controlled responsive to the sensed values. It is understood that the logistic transport container may take any known form, including, but not limited to, transport containers on a ship, rail car, airplane, trailer, or truck. Such containers may comprise one compartment, or may comprise multiple segregated compartments, wherein each compartment may independently provide the benefits of the inventions disclosed herein. Alternatively, the logistic transport container may take the form of a cardboard box shipped via ship, rail car, airplane, trailer, or truck. In yet another alternative, the logistic transport container may take the form of a ship's hold, rail box-car, airplane hold, closed trailer, or closed box-truck.

In this example, ethylene levels are monitored by ethylene sensors inside of a logistic transport container containing fruit. Ethylene is a gaseous plant hormone, produced by fruit, crops, flowers, and plants. In the case of fruit, ethylene is a gaseous hormone responsible for ripening, and the ripening process can not only be monitored by sensing ethylene levels, the ripening rate can be optimized by controlling the ethylene levels responsive to the sensed ethylene levels. For instance, if sensed ethylene levels are determined to be too low, the controller of the logistic transport container may seal the container to allow ethylene concentrations to increase, or may add ethylene gas to achieve desired levels. Alternatively, if sensed ethylene levels are determined to be too high, the controller of the logistic transport container may ventilate the container, allowing ethylene concentrations to decrease by dilution, or may add specific gasses to achieve desired ethylene levels.

In another alternative, such gas and smell sensors may be used to monitor ripeness of a single fruit, wherein the single fruit serves as an indicator for a batch of fruit subjected to the same logistic transport environment. For instance, a jar containing a single piece of fruit chosen as a representative of a corresponding batch of fruit can be continuously sampled to measure the rate of ethylene production. In this way, the ethylene production rate of fruit during logistic transport may be determined, and accordingly, their current state of ripeness.

Figure 14:
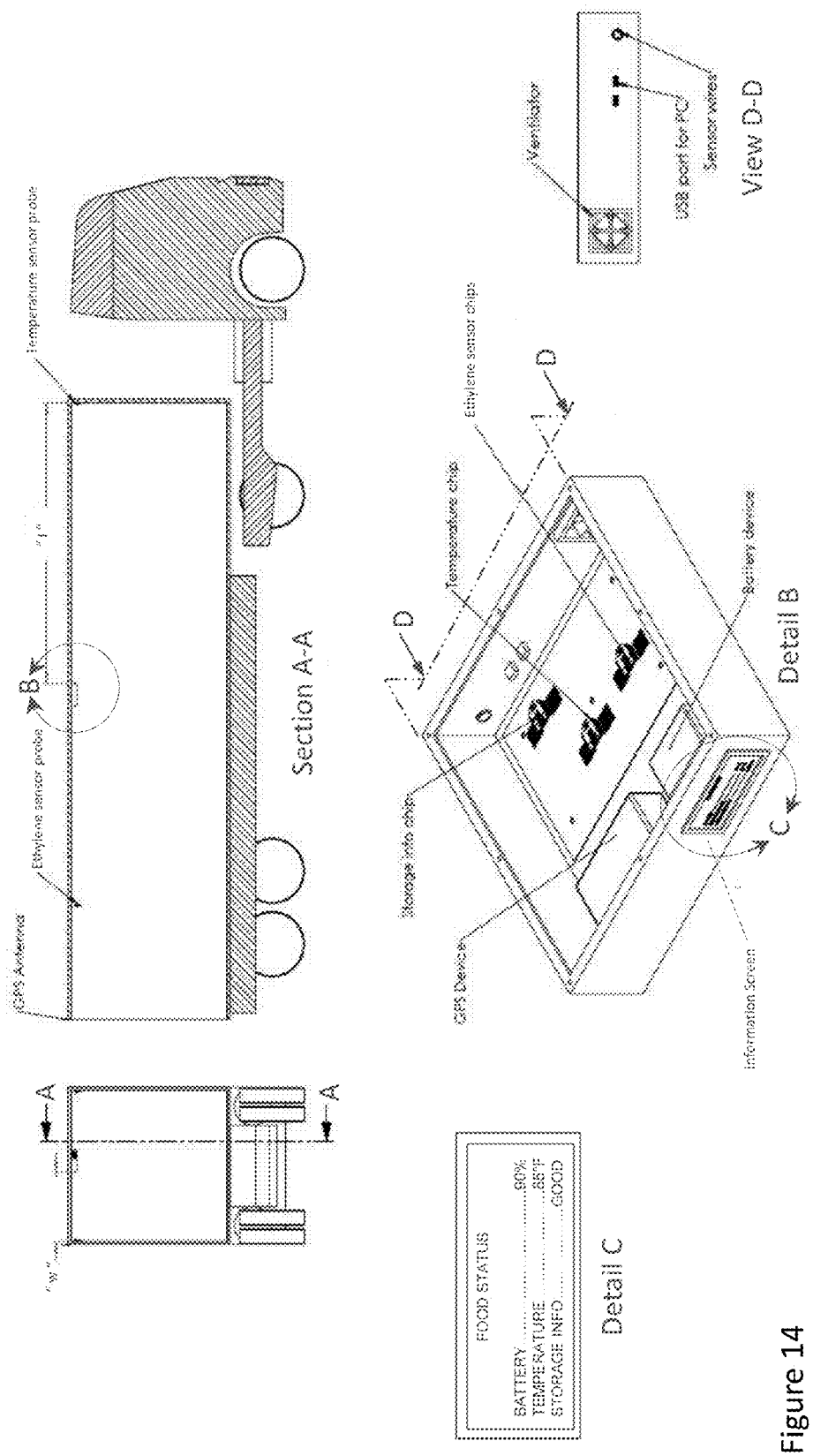
FIG. 14 shows a logistic transport system according to embodiments of the present invention.

FIG. 14 shows embodiments wherein the logistic transport container comprises a container being transported by tractor-trailer. The container has four side walls, a bottom wall, and a top wall, defining an interior space. In an example, the container's contents is a bulk shipment of produce, for instance, fruit (not shown). The container is provided with a sensing module, as shown in Detail B of FIG. 14. The sensing module is placed in any suitable fashion inside the container, for instance, as indicated by "B" in Section A-A of FIG. 14, fixed to an interior surface of the container's top wall at a distance "l" relative to a first side wall of the container, and a distance "w" from a second side wall of the container. The sensing module may comprise: a gas or smell sensor, in this example, an ethylene sensor, as indicated by "Ethylene sensor chips" (it is understood that gas or smell sensors may be provided to sense any gas, such as, but not limited to $O_2$ and $CO_2$, any airborne volatiles, and any number or combination thereof); other sensors, in this example, a temperature sensor, as indicated by "Temperature chip" (it is understood that these other sensors may be provided to sense any environmental condition, or combination of environmental conditions, inside the container, including, but not limited to pressure, humidity, time, temperature and humidity, and so forth); optical sensors, not shown in FIG. 14 (it is understood that such optical sensors may include, but are not limited to, Raman, hyperspectral, and near infra-red spectrometers, and may sense a target attribute associated with a particular nutritional or organoleptic property of the contents of the logistic transport container, such as by scanning the contents to provide a corresponding scan-response); a GPS device, which may further comprise a time and date device to provide a time and date stamp corresponding to when GPS and sensor information is obtained, as indicated by "GPS Device", which may further be provided with a remote antenna, as indicated by "GPS Antenna"; an information storage device, indicated by "Storage info chip", wherein the information storage device may store, manage, and transmit information sensed by the various gas and smell sensors, optical sensors, and other sensors, the GPS device, and a unique identifier associated with the contents of the container; and a power source, indicated by "Battery device", which may comprise a battery, connection for external power, or both.

The sensing module may further be provided with an air exchange capability, indicated by "Ventilator", wherein the atmosphere within the container is passively or actively exposed to some or all of the various gas and smell sensors, optical sensors, and other sensors, having sensor probes in local proximity to the sensor. Additionally, or alternatively, some or all of the various gas and smell sensors, optical sensors, and other sensors of the sensing module may communicate with corresponding sensor probes placed remotely from the sensing module at locations within the container. Remotely placed gas and smell sensor probes are indicated by "Ethylene sensor probe", and other remotely placed sensor probes are indicated by "Temperature sensor probe". Optical sensor probes may be provided remotely as well, and may further be provided on a track allowing movement in one, two, or three axes relative to the contents. Communication with a remote sensor probe may be accomplished by hardwire connection of a corresponding sensor to connectors provided on an exterior of the sensing module, indicated by "Sensor wires", and further by plugging the wire of the sensor probe into the connector. It is understood that communication between a sensor and a remotely placed sensor probe may be accomplished in any known wired or wireless fashion, and the wired example provided herein is only provided for illustrative purposes.

The sensing module may further be provided with a user interface, indicated as "Information Screen", wherein various current or stored information may be displayed related to the container, its contents, and the sensing module. The information displayed may be related to: the unique identifier associated with the contents of the container; information provided by the various gas and smell sensors and optical sensors, as indicated by "Storage Info"; information provided by the other sensors, as indicated by "Temperature"; information regarding a ΔN or corresponding residual nutritional, organoleptic, or aesthetic value of the container's contents; a current state of the power source, as indicated by "Battery"; and a current location of the container, as determined by the GPS device. Additionally, or alternatively, the sensing module may be provided with the capability to communicate the various current or stored information with a computer or other external information system, such as by connection of the information storage device to a USB port available externally of the sensing module, as indicated by "USB port for PC". It is understood that such communication capability may be accomplished in any known wired or wireless fashion, and the example of a USB port provided herein is provided only for the purpose of illustration. Such communication capability may include, but is not limited to, any know type of active or passive transmitter for transmitting information stored in the information storage device. Transmission may occur at or upon one or more of: predetermined times; predetermined sensor limits; external query, and proximity to an information receiving system. Information receiving systems causing transmission to occur based on proximity of the container relative to the information receiving system may be located at any point of departure, transit (such as in close proximity to roadways), transfer, inspection, or receipt of the logistic transport container.

In a preferred embodiment, a logistic transport container is provided with a sensing module including: separate or combined ethylene and $CO_2$ sensors; separate or combined temperature and humidity sensors; one or more stationary optical sensors, including Raman or hyper-spectral spectrometers; device for information storage, management, and transmission, wherein such transmission may be accomplished by an RF antenna; and a GPS device to provide a location, time, and date stamp corresponding to when sensor information is obtained. It is understood that any part of the information stored by the sensing module may additionally be stored remotely. For example, the sensing modules device for information storage may have limited storage capacity, in which case it may be useful to periodically transmit the information contained therein to a remote database, such as the dynamic nutritional value database. Such periodic transmission might occur at specific locations, at specific times, upon data capacity thresholds, or in any other fashion known to one skilled in the art.

In an alternative embodiment, the sensing module includes one or more track mounted Raman or hyper-spectral spectrometers, such that the corresponding one or more spectrometers can move in one, two, or three axes with respect to the contents of the logistic transport container. It is understood that any other known type of sensor may be track mounted such that it may move in one, two, or three axes with respect to the contents of the container.

In another embodiment, the sensing module is not provided with a Raman or hyper-spectral spectrometer, rather, a separate Raman or hyper-spectral spectrometer is used to sense the contents of the logistic transport container when the contents are loaded into the container, and a separate Raman or hyper-spectral spectrometer is used to sense the contents of the logistic transport container when the contents arrive at a particular destination, such as a point of inspection or delivery. It is understood that any other known type of sensor, including Raman spectrometers, for example, may be used to sense the contents of the logistic transport container when the contents are loaded into the container and when the contents arrive at a particular destination. Information obtained by the various sensors, whether part of the sensing module or separate, including information obtained upon loading the logistic transport container, throughout its transit, and at particular interim or final destinations, can be used to understand the evolution of nutritional, organoleptic, or aesthetic values of the contents. If the information provided by any particular sensor provides a contradictory understanding of the evolution, it may indicate that the particular sensor is suspect, and may further result in a notification to verify the particular sensor or other sensors.

In further embodiments, the sensing module is provided as a removable unit. In this way, it may be placed into a container not equipped with a sensing module so as to enable the container to function according to the inventions described herein. The removable sensing module may subsequently be removed from the container, for example, for use in another container, for service, or for any other reason.

In further embodiments, the sensing module is provided with an information screen, wherein various current or stored information may be displayed related to the container, its contents, and the sensing module. The information displayed may be related to the unique identifier associated with the contents of the container, information provided by the various sensors of the container, a current state of the power source, a current location, time, or date, or information regarding a $\Delta N$ or corresponding residual nutritional, organoleptic, or aesthetic value of the container's contents. Information regarding a $\Delta N$ or corresponding residual nutritional, organoleptic, or aesthetic value may be communicated by a dynamic indicator.

Figure 15A:
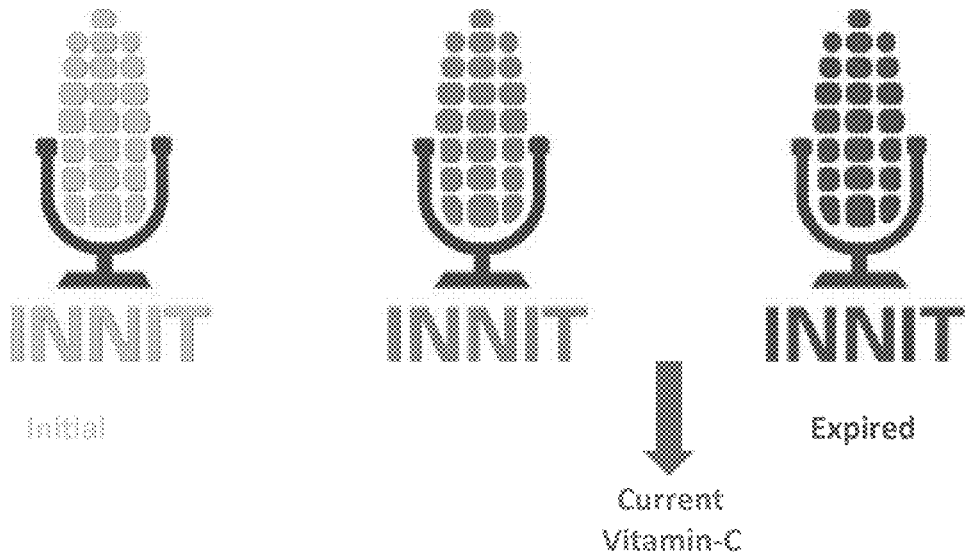
FIGS. 15*a* and 15*b* show formats of a dynamic indicator by which a $\Delta N$, and related residual and initial nutritional, organoleptic, and aesthetic values, may be expressed.
Figure 15B:
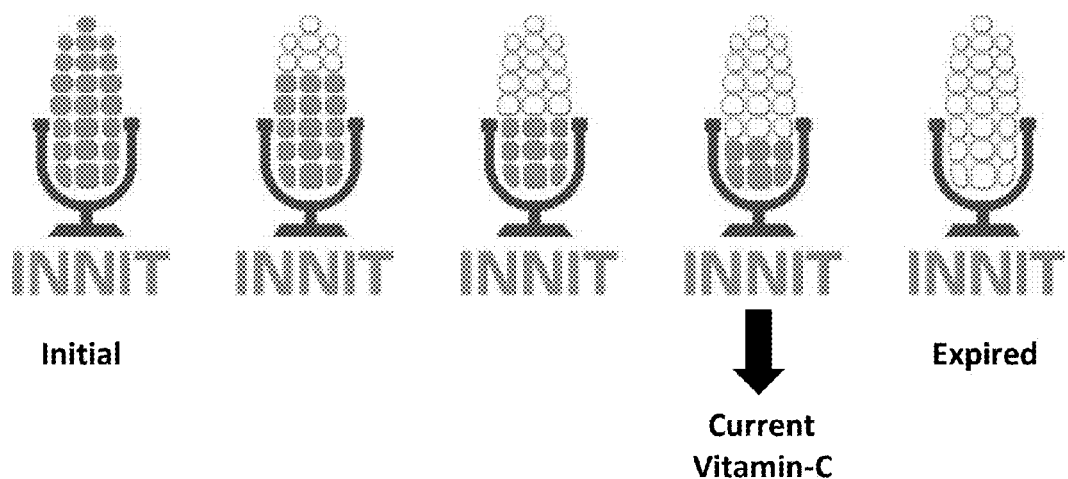

FIGS. 15a and 15b show formats of a dynamic indicator according to the present invention by which a $\Delta N$, and related residual and initial nutritional, organoleptic, and aesthetic values, may be expressed. The ear of corn shown on a microphone stand and labeled "INNIT" in FIGS. 15a and 15b represents a nutritional, organoleptic, or aesthetic value associated with a nutritional substance. While any object may be chosen to represent a nutritional, organoleptic, or aesthetic value, in a preferred embodiment, the chosen object corresponds to a logo, symbol, mascot, or other object associated with a Brand. Such a Brand might be associated with a nutritional substance information system according to the present inventions, a Measurement, Inspection, Engineering, Regulatory, Certification, or other Standard, or any other Brand associated with the nutritional substance and information industry. The object chosen to represent a nutritional, organoleptic, or aesthetic value is also referred to herein as a $\Delta N$ meter. In the following examples, the $\Delta N$ meter is the ear of corn shown on a microphone stand and labeled "INNIT" shown in FIGS. 15a and 15b, and corresponds to the logo of the provider of a nutritional substance information system according to the present inventions.

In FIG. 15a, a $\Delta N$ meter according to the present invention communicates various items regarding a nutritional value, for instance Vitamin-C value, in a corresponding nutritional substance, for instance, a carton of orange juice provided with a dynamic information identifier. A consumer desiring information regarding Vitamin-C values of the orange juice can use his smartphone to scan the dynamic information identifier and determine the desired information. In this example, the information is presented to the consumer on the screen of his smartphone in the form of the $\Delta N$ meter shown in FIG. 15a. The $\Delta N$ meter of this example communicates symbolically through color, and color changes, the initial Vitamin-C value, the current Vitamin-C value, and an expired Vitamin-C value. The values may be shown as relative values without units of measure, as shown, or may further be provided with actual units of measure. In this example, the consumer is provided with a conceptual indicator regarding how much the Vitamin-C value has degraded relative to its initial value and where its current Vitamin-C value is relative to the expiration value of the Vitamin-C.

In FIG. 15b, a $\Delta N$ meter according to the present invention communicates various items regarding a nutritional value, for instance Vitamin-C value, in a corresponding nutritional substance, for instance, a carton of orange juice provided with a dynamic information identifier. A consumer desiring information regarding Vitamin-C levels of the orange juice can use his smartphone to scan the dynamic information identifier and determine the desired information. In this example, the information is presented to the consumer on the screen of his smartphone in the form of the ΔN meter shown in FIG. 15b. The ΔN meter of this example communicates symbolically through percent fill-level, and percent fill-level changes, the initial Vitamin-C value, the current Vitamin-C value, and an expired Vitamin-C value. The values may be shown as relative values without units of measure, as shown, or may further be provided with actual units of measure. In this example, the consumer is provided with a conceptual indicator regarding how much the Vitamin-C value has degraded relative to its initial value and where its current Vitamin-C value is relative to the expiration value of the Vitamin-C.

It is understood that ΔN meters may take many forms and communicate various messages regarding a ΔN value or a residual nutritional, organoleptic, and/or aesthetic value of nutritional substances, and the examples provided above are for illustrative purposes and not intended to be limiting in any way. It is further understood that ΔN meters may be utilized to communicate ΔN values and residual nutritional, organoleptic, and/or aesthetic values determined or estimated in any fashion. Dynamic indicators such as ΔN meters may be communicated through the user interface of the readers of preservation modules of the present inventions, through the sensors or sensing modules of the present invention, through any user interface provided for the creation, transformation, conditioning, consumption, and information modules of the present inventions, and thought any other known format capable of communicating such information. In preferred embodiments, the ΔN value or the residual nutritional, organoleptic, and/or aesthetic value are determined utilizing the nutritional substance information systems disclosed herein, including systems utilizing dynamic information identifiers and corresponding nutritional substance database, systems utilizing nutritional attribute sensors and corresponding nutritional substance attribute library, or a combination of both.

In an embodiment, a method is provided for determining and communicating the evolution of a nutritional, organoleptic, or aesthetic value of a nutritional substance. In the method, a first value of a particular nutritional, organoleptic, or aesthetic property is determined at a first time. Determination is made by scanning a nutritional substance at a first time to obtain a first scan-response related to a target attribute, then analyzing the scan-response, by any methods known to those skilled in data processing and analysis, including the application of statistical methods and creation of analytical algorithms, and correlating the first scan-response to the first value of the particular nutritional, organoleptic, or aesthetic property of the nutritional substance and to a dynamic information identifier associated with the nutritional substance. At a second time, a second value of the particular nutritional, organoleptic, or aesthetic property is determined. Determination is made by scanning the nutritional substance at a second time to obtain a second scan-response related to the target attribute and analyzing the second scan-response, by any methods known to those skilled in data processing and analysis, including the application of statistical methods and creation of analytical algorithms, and correlating the second scan-response to the second value of the particular nutritional, organoleptic, or aesthetic property of the nutritional substance and to the dynamic information identifier associated with the nutritional substance. At a subsequent time, a subsequent value of the particular nutritional, organoleptic, or aesthetic property is determined. Determination is made by scanning the nutritional substance at a subsequent time to obtain a subsequent scan-response related to the target attribute and analyzing the subsequent scan-response, by any methods known to those skilled in data processing and analysis, including the application of statistical methods and creation of analytical algorithms, and correlating the subsequent scan-response to the subsequent value of the particular nutritional, organoleptic, or aesthetic property of the nutritional substance and to the dynamic information identifier associated with the nutritional substance. The difference between any two of the first, second, and subsequent values of the particular nutritional, organoleptic, or aesthetic property of the nutritional substance describes a ΔN occurring between the corresponding times and can be referenced to the dynamic information identifier associated with the nutritional substance. Further, any two of the first, second, and subsequent values of the particular nutritional, organoleptic, or aesthetic property of the nutritional substance can be used to create a table, graph, or curve showing the change in the particular nutritional, organoleptic, or aesthetic property occurring over the corresponding times, and can be referenced to the dynamic information identifier associated with the nutritional substance. In a further embodiment, the first, second, and subsequent scan-responses may each be referenced to the dynamic information identifier of the nutritional substance and transmitted when first obtained.

Communicating the evolution of the particular nutritional, organoleptic, or aesthetic value of the nutritional substance can be accomplished in any fashion known to one skilled in the art. Examples include, but are not limited to: simply providing the first value, the second or subsequent value, and the change between the first value and the second or subsequent value, expressed in the corresponding unit of measure; providing the first value, the second or subsequent value, and the change between the first value and the second or subsequent value, expressed as a percentage; providing the first value, the second or subsequent value, and the change between the first value and the second or subsequent value, expressed as a percentage of a recommended daily requirement (for instance, % RDA could express such values as a percentage of the FDA's Recommended Daily Allowance); providing a table, graph, or curve showing the first and second values, wherein the values may be expressed in a corresponding unit of measure, as a percentage, as a percentage of a recommended daily requirement, or in any known graphical fashion; and providing a ΔN meter.

There are many examples of sensor technology that might be utilized as a nutritional substance attribute sensor, including, but not limited to: Surface plasmon resonance sensors (SPR) such as a cell phone based sensor platform disclosed by Preechaburana et at, Angew. Chem. Int. Ed. 2012, 51, 11585-11588, "Surface plasmon resonance chemical sensing on cell phones"; SPR sensors such as those disclosed by Zhang, et al, Zhejiang University, Hangzhou 310058, P.R. China "Detection of penicillin via surface plasmon resonance biosensor"; the combination of microfluidics with Lab-on-a-Chip and Lab-on-a-Foil solutions disclosed by Focke, et al, www.r-sc.org/loc, 19 Mar. 2010, "Lab-on-a-Foil: microfluidics on thin and flexible films"; Localized surface plasmon response sensors (LSPR) such as those disclosed by Roche, et al, Journal of Sensors, volume 2011, article ID 406425, doi: 10.1155/2011/406425, "A camera phone localized surface plasmon biosensing platform towards low-cost label-free diagnostic testing"; printed sensors such as those available from Thin Film Electronics ASA, for example the Thinfilm Time-Temperature Sensor; wireless pH sensors such as those discussed in IEE Sensors Journal, Vol 12, No. 3, March 2012 487 "A passive radio-frequency pH sensing tag for wireless food quality monitoring"; sensing of biological quantities such as that discussed in Appl Microbiol Biotechnol (2013) 97:1829-1840 "An overview of transducers as platform for the rapid detection of foodborne pathogens"; cell phone based *E. Coli* sensor using florescent imaging to detect bacteria in food and water, developed at UCLA Henry Samueli School of Engineering and Applied Science; sensors discussed in Journal of Food Engineering 100 (2010) 377-387 "Biomimetric-based odor and taste sensing systems to food quality and safety characterization: An overview on basic principals and recent achievements"; sensors discussed in Sensors 2010, 10, 3411-3443, doi 10.3390/s100403411 "Advanced Taste Sensors Based on Artificial Lipids with Global Selectivity to Basic Taste Qualities and High Correlation to Sensory Scores"; sensing described in Chem. Sci., 2012, 3, 2542 "Fluorescent DNAs printed on paper: sensing food spoilage and ripening in the vapor phase"; the use of a Silicon Integrated Spectrometer to sense food for ripeness and other qualities is described in IEEE Photonics Journal, 1 (4), p. 225-235 (2009); numerous sensing techniques described in analytica chima acta 605 (2007) 111-129 "A review on novel developments and applications of immunosensors in food analysis"; numerous sensing techniques described in J. Biophotonics 5, No. 7, 483-501 (2012)/doi 10.1002/jbio.201200015 "Surface plasmon resonance based biosensor technique: A review"; LSPR techniques to sense bitterness of tea described in Agric. Food Chem., 2010, 58 (14), pp 8351-8356 "B-Cyclodextrin/Surface plasmon response detection system for sensing bitter astringent taste intensity of green tea catechins"; a review on nano-biosensors to measure tastes and odors discussed in Bio-Nanotechnology: A revolution in food biomedical and health sciences, first edition, 2013, John Wiley & Sons, Ltd. "Nano-Biosensors for mimicking gustatory and olfactory senses"; techniques described in Science Daily, http://www.sciencedaily.com/releases/2013/02/130214111612.htm, 14 Feb. 2013 "World's most sensitive plasmon resonance sensor inspired by the ancient roman cup"; ethylene sensors discussed in Anal. Chem., 2011, 83 (16), pp 6300-6307, doi: 10.1021/ac2009756 "Electrochemical sensing of ethylene employing a thin ionic-liquid layer"; multiplex SPR techniques described in Anal Bioanl Chem (2011) 400: 3005-3011, doi 10.1007/s00216-011-4973-8 "Imaging surface plasmon resonance for multiplex microassay sensing of mycotoxins"; a review of noble metal nono-optical sensors based on LSPR by Zhao, et al, "Localized surface plasmon resonance biosensors"; colorimetric plasmon resonance imaging described by Garda, et al, Advanced Optical Materials 2013, 1, 68-76, doi: 10.1002/adom.201200040 "Colorimetric plasmon resonance imaging using nano Lycurgus cup arrays"; sensor using multiplex fiber-optic biosensor implemented by integrating multiple particle plasmon resonances (PPRs), molecular bioassays, and microfluidics is disclosed by Lin, et al, Proc. SPIE 8351, Third Asia Pacific Optical Sensors Conference, 83512S (Jan. 31, 2012), doi: 10.117/12.914383 "Multiplex fiber-optic biosensor using multiple particle plasmon resonances"; sensor based on multilayered graphene SPR-based transmission disclosed by Kim, et al, J. Nonosci. Nanotechnol, 2012 July 12(7):5381-5 "Evaluation of multi-layered graphene surface plasmon resonance-based transmission type fiber optic sensor"; sensors to detect Mercury values such as the biosensors, chemical sensors, conductometric sensors, microcantilevel sensors, SAW sensors, piezoelectric sensors, and nanosensors similar to those described by: Selid et al, Sensors 2009, 9, 5446-5459; doi: 10.3390/s90705446; and Katherine Davies, Royal Society of Chemistry, Chemistry World, New chemosensor for mercury detection (http://www.rsc.org/chemistryworld/Issues/2005/July/mercury_detection.asp); sensors to detect caffeine values may be similar to those described by: Chung I C, et al, J Nanosci Nanotechnol. 2011 December; 11(12):10633-8, A portable electrochemical sensor for caffeine and (−)epigallocatechin gallate based on molecularly imprinted poly(ethylene-co-vinyl alcohol) recognition element.; or Ebarvia, et al, Analytical and Bioanalytical Chemistry, March 2004, Volume 378, Issue 5, pp 1331-1337, Biomimetic piezoelectric quartz sensor for caffeine based on a molecularly imprinted polymer.; or Zhao, et al, http://www.researchgate.net/publication/225410860, Department of Material and Chemistry Engineering, Henan Institute of Engineering, Zhengzhou, 450007 China, Article-Voltammetric sensor for caffeine based on a glassy carbon electrode modified with Nafion and graphene oxide; sensors to detect sugar values may be similar to those described by: Kumar, et al, http://www.researchgate.net/publication/225803614, Study of fiber optic sugar sensor; or Scampicchio, et al, Nanotechnology 20 135501 doi:10.1088/0957-4484/20/13/135501, Issue 13, 1 Apr. 2009, Optical nanoprobes based on gold nanoparticles for sugar sensing; sensors to detect temperature values may be similar to those manufactured by MICRO-EPSILON, and described at www.micro-epsilon as miniature non-contact IR sensors thermoMETER CSmicro and non-contact IR sensors with laser aiming thermoMETER CSlaser; sensors for detecting temperature values may also include any thermocouple type sensor suitable for contact sensing of temperature. It is understood that sensors may be configured to perform multiple test assays in a single use to develop a multidimensional dataset from each use.

Other examples of sensor technology that might be utilized includes sensors similar to those manufactured by MICRO-EPSILON and described at www.micro-epsilon as fixed lens color sensors color SENSOR OT-3-GL and OT-3-LU. These sensors illuminate a surface with white light and sense the reflected color values, and are particularly useful for color recognition of non-homogeneous targets and glossy targets, for instance, a piece of beef or other animal tissue packaged in clear cellophane, packaged in shrink-wrap, or not currently packaged. These sensors can also provide useful information regarding the turbidity of liquids. Alternatively, sensors may be similar to those manufactured by MICRO-EPSILON and described at www.micro-epsilon as fiber color sensors, color SENSOR LT-1-LC-20, WLCS-M-41, and LT-2. These sensors use a modulated white light LED to project a spot onto or through a target, and focusing part of the reflected or transmitted light with fiber optic onto a color detector element. Common sensing techniques include, but are not limited to: projecting a spot directly on and normal to an inspection target and focusing part of the back-scattered light with fiber optic onto a color detector; projecting a spot indirectly, that is at an angle to, an inspection target and focusing part of the reflected light with fiber optic onto a color detector; and projecting a spot directly through an inspection target and focusing part of the transmitted light with fiber optic onto a color detector. Such a nutritional substance attribute sensor may be configured to include a white light source and color detector as a permanent part of a detector, and a coupler that enables attachment of the detector to the mating coupler of various fiber optic probe configurations to project light from the light source onto or through a target and to focus reflected or transmitted light from the target onto the color detector.

Such fiber optic probes may be provided as a permanent part of a sealed nutritional substance package, wherein the portions of the probe required to interface with the nutritional substance are in direct contact with the nutritional substance, and the mating coupler that allows removable attachment to the sensor coupler provided with the detector is available externally of the package. Permanently incorporating the sensor probe into the package has many benefits. The portion of the sensor probes in contact with the nutritional substance can be tailored to the specific product and package, while the mating coupler on the outside of the package is always provided in the configuration compatible with the sensor coupler on the detector. This enables sensing of a wide array of packaged nutritional substances without disrupting package integrity. It also simplifies the task greatly for a user, and ensures consistent and accurate sensing technique.

Sensing technologies utilizing hyper-spectral imaging are potentially useful as nutritional substance attribute sensors, and because of their speed and ability to provide high volume, in-line/in-process detection, may be particularly useful for applications during logistic transport. Hyper-spectral imaging has been utilized, for example, for in-line inspection of produce such as apples and strawberries, and has also been utilized for rapid inspection of meat products such as poultry and seafood. This technology is particularly useful for identifying anomalies in nutritional substances without disrupting the nutritional substance. All substances have unique spectral signatures, which can be saved in a library. Libraries including the spectral responses of known nutritional substances in known nutritional, organoleptic, or aesthetic conditions, and further including known sources of adulteration, such as fecal matter, chemical contamination, micro-organisms and other pathogens or disease conditions, can be used for comparison to spectral responses of nutritional substances currently being sensed, and in this way the currently sensed nutritional substance can be quickly characterized according to desired characterization criteria. Hyper-spectral sensing may further be utilized for plant and crop phenotyping, whereby a composite of a nutritional substance's observable characteristics provides a unique fingerprint. This can be particularly beneficial to rule out adulteration such as by partial or total ingredient substitution.

Still other examples of optical sensor technology that might be utilized include, but are not limited to: handheld Raman spectrometers available from Serstech, www.serstech.com; PinPointer™ handheld Raman spectrometer available from Ocean Optics, www.oceanoptics.com; TruScan RM handheld Raman spectrometer available from Thermo Fisher Scientific; near infra-red sensor available from Thermo Fisher Scientific; Xantus Mini™ remote controlled, smartphone compatible Raman spectrometer available from Rigaku, www.rigaku.com; Lighting Passport handheld or remote smartphone compatible spectrometer from Asensetek, www.alliedscientificpro.com.

In preferred embodiments, packaged nutritional substances are sensed by nutritional substance attribute sensors without disrupting the integrity of the package. As used herein, a nutritional substance package is any type of nutritional substance container, storage device or recipient, including, but not limited to, cups, bottles, glasses, bags, boxes, wrappers, caps, lids, covers, logistic transport containers, and so forth. In some embodiments this is accomplished with existing packaging. In other embodiments, nutritional substance packaging is provided to enable sensing of nutritional substance attribute values without opening the package. Such packaging may incorporate non-contact interface ports, such as a glass or plastic window of known refractive index, into the nutritional substance packaging, wherein such ports allow interaction between a nutritional substance attribute sensor and the nutritional substance without disrupting the package integrity. This may also be accomplished by incorporating product contact portions of a nutritional substance attribute sensor into the nutritional substance packaging, and providing ports allowing interaction between the product content portion and the nutritional substance attribute sensor without disrupting the package integrity. Alternatively, this may be accomplished by further providing the product contact portion with the ability to transmit sensed values to a device equipped to receive such transmission, such as a detector. Alternatively, such transmission of sensed values may be provided by a signal generated by a passive RFID tag when it is in proximity to a corresponding RF scanner, by the signal generated by an active RFID tag and received by a corresponding RF scanner, or by any known formats for transmitting data. In an example, and not to be limiting in any way, thin film chips such as the tagging system manufactured by Kovio of San Jose, Calif., USA, can be used not only for tracking nutritional substances, but can include components to measure attributes of nutritional substances, and record and transmit such information. Such information may be readable by a reader including a satellite-based system. Such a satellite-based nutritional substance information tracking system could comprise a network of satellites with coverage of some or all the surface of the earth, so as to allow the dynamic nutritional value database of information module 100 real time, or near real time updates about a $\Delta N$ of a particular nutritional substance.

The ability to determine corroborating evidence of the authenticity of nutritional substances packaged with known packaging, and the residual nutritional, organoleptic, and aesthetic values, such as by sensing nutritional substance attribute values without disrupting the integrity of the package and providing packages that widely expand the ability to do so, provides great utility and benefit for the nutritional substance supply system.

It is understood that the present inventions are not limited in scope by the examples of sensors and sensor probes disclosed herein. Nutritional substance packages may be provided with sensor probe portions of any known sensing technology in contact with the nutritional substance contained therein, and further provided with the ability to communicate sensed values by any known mechanism, including, but not limited to, optic coupling, electronic coupling, acoustic coupling, mechanical coupling, non-contact coupling such as RF, Bluetooth, inductive field, or any other non-contact coupling, and so forth.

Further, it is understood that many other sensing capabilities and sampling formats may be employed. It is also understood that the current inventions enable users of packaged nutritional substances to determine corroborating evidence of the authenticity of the nutritional substances and current values for dynamically changing and evolving nutritional, organoleptic, and aesthetic values of the nutritional substances. Such changes and evolution may be through expected degradation, such as orange juice loosing vitamin-C or yogurt loosing active *Lactobacillus*, may be through unexpected degradation, such as oxidation resulting from a broken package seal, or may be through maturation, such as evolving sugar, alcohol, and tannin content of wine, or the maturation of cheese. Determination of a current nutritional, organoleptic, and aesthetic value of a nutritional substance provides information regarding changes that have occurred in corresponding nutritional, organoleptic, and aesthetic values, as well as the corresponding residual nutritional, organoleptic, and aesthetic values. Further, this provides useful information regarding best-use, maturation, stabilization, or expiration of the corresponding nutritional, organoleptic, and aesthetic value, and can even be utilized to indicate adulteration of the nutritional substance.

Systems with the ability to periodically or continuously sense and communicate residual nutritional, organoleptic, or aesthetic values of packaged nutritional substances, the ability to rule out adulteration of the packaged nutritional substances, and the ability to provide corroborating evidence of the authenticity of the packaged nutritional substances, without disrupting the integrity of the package (which includes any form of preservation, storage, or logistic transport) is particularly beneficial during logistic transport. For example, the time, labor, and expense associated with logistic transport of produce and other nutritional substances through agricultural check points could be dramatically reduced by such systems. As an example, and not to be limiting in any way, such a system could be utilized by a highway, rail, or maritime produce shipper, wherein the residual nutritional, organoleptic, or aesthetic values of packaged nutritional substances, the ruling out of adulteration, and corroborating evidence of the authenticity of the packaged nutritional substances is provided at an agricultural check point instantly, without disrupting the integrity of the package, and without the manual verification, delay, and product holds currently experienced. For instance, RFID tags associated with the packaged nutritional substance, in this case the logistic transport system of the highway, rail, or maritime produce shipper, automatically transmit the residual nutritional, organoleptic, or aesthetic values of packaged nutritional substances, the ruling out of adulteration, and corroborating evidence of the authenticity, when in proximity to RFID sensors positioned next to a fast-track lane provided at the check point.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. As used herein, the terms "connected," "coupled," or any variant thereof means any connection or coupling, either direct or indirect, between two or more elements. Such a coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. While processes or blocks are presented in a given order in this application, alternative implementations may perform routines having steps performed in a different order, or employ systems having blocks in a different order. Some processes or blocks may be deleted, moved, added, subdivided, combined, and/or modified to provide alternative or sub-combinations. Also, while processes or blocks are at times shown as being performed in series, these processes or blocks may instead be performed or implemented in parallel, or may be performed at different times. Further any specific numbers noted herein are only examples. It is understood that alternative implementations may employ differing values or ranges.

The various illustrations and teachings provided herein can also be applied to systems other than the system described above. The elements and acts of the various examples described above can be combined to provide further implementations of the invention.

Any patents and applications and other references noted above, including any that may be listed in accompanying filing papers, are incorporated herein by reference. Aspects of the invention can be modified, if necessary, to employ the systems, functions, and concepts included in such references to provide further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

While certain aspects of the invention are presented below in certain claim forms, the applicant contemplates the various aspects of the invention in any number of claim forms. For example, while only one aspect of the invention is recited as a means-plus-function claim under 35 U.S.C. §112, sixth paragraph, other aspects may likewise be embodied as a means-plus-function claim, or in other forms, such as being embodied in a computer-readable medium. Any claims intended to be treated under 35 U.S.C. §112, ¶6 will begin with the words "means for." Accordingly, the applicant reserves the right to add additional claims after filing the application to pursue such additional claim forms for other aspects of the invention.

The invention claimed is:

1. The logistic transport system for preservation of nutritional substances comprising:
   a mobile container for preserving a perishable nutritional substance during transport, the perishable nutritional substance being associated with a unique identifier;
   a gas sensor and an optical sensor for directly sensing attribute information of the perishable nutritional substance itself during transport and indicating a change in value of a specific nutritional or organoleptic property of the perishable nutritional substance during transport;
   a temperature and humidity sensor for sensing environmental information inside the container during transport and indicating a change in value of the specific nutritional or organoleptic property;
   a device to dynamically provide location, date, and time information of the mobile container;

information storage for storing the sensed attribute information, the environmental information, the location, date and time information, and the unique identifier; and a controller for adapting conditions inside the mobile container during transport of nutritional substances responsive to at least one of the sensed attribute information of the perishable nutritional substance and the sensed environmental information inside the container, to alter a rate of change in the value of the specific nutritional or organoleptic property of the perishable nutritional substance during transport.

2. The logistic transport system for preservation of nutritional substances according to claim 1 further comprising:

a transmitter to transmit to a dynamic nutritional value database the sensed attribute information, the sensed environmental information, and the dynamically provided location, date and time information, wherein said information is referenced to the unique identifier.

3. The logistic transport system for preservation of nutritional substances according to claim 2 wherein:

the change in value of the specific nutritional or organoleptic property of the perishable nutritional substance is accessed in the dynamic nutritional value database by reference to the unique identifier.

4. The logistic transport system for preservation of nutritional substances according to claim 2 wherein:

the dynamic nutritional value database is available to at least one of a creation, preservation, transformation, conditioning, and consumer module.

5. The logistic transport system for preservation of nutritional substances according to claim 2 wherein:

referencing the unique identifier in the dynamic nutritional value database enables at least one of an adaptive transformation, adaptive conditioning, and adaptive consumption of the nutritional substance.

6. The logistic transport system for preservation of nutritional substances according to claim 1 wherein:

the gas sensor comprises at least one of an ethylene sensor, $CO_2$ sensor, and $O_2$ sensor.

7. The logistic transport system for preservation of nutritional substances according to claim 1 wherein:

the optical sensor comprises at least one of a Raman, hyperspectral, and near infra-red spectrometer.

8. The logistic transport system for preservation of nutritional substances according to claim 1 further comprising:

a user interface for communicating a current value of the changing nutritional or organoleptic property of the perishable nutritional substance.

\* \* \* \* \*